(12) United States Patent
Bright et al.

(10) Patent No.: US 11,154,547 B2
(45) Date of Patent: Oct. 26, 2021

(54) TREATMENT OF SEPSIS AND RELATED INFLAMMATORY CONDITIONS BY LOCAL NEUROMODULATION OF THE AUTONOMIC NERVOUS SYSTEM

(71) Applicant: Tulavi Therapeutics, Inc., Los Altos Hills, CA (US)

(72) Inventors: Corinne Bright, Los Altos Hills, CA (US); Kondapavulur T. Venkateswara-Rao, San Jose, CA (US); Emily Stein, San Jose, CA (US)

(73) Assignee: Tulavi Therapeutics, Inc., Los Altos Hills, CA (US)

( * ) Notice: Subject to any disclaimer, the term of this patent is extended or adjusted under 35 U.S.C. 154(b) by 0 days.

(21) Appl. No.: 16/313,856

(22) PCT Filed: Jun. 29, 2017

(86) PCT No.: PCT/US2017/040074
§ 371 (c)(1),
(2) Date: Dec. 27, 2018

(87) PCT Pub. No.: WO2018/005848
PCT Pub. Date: Jan. 4, 2018

(65) Prior Publication Data
US 2020/0085809 A1    Mar. 19, 2020

Related U.S. Application Data

(60) Provisional application No. 62/355,889, filed on Jun. 29, 2016.

(51) Int. Cl.
| | | |
|---|---|---|
| *A61K 31/455* | (2006.01) | |
| *A61P 29/00* | (2006.01) | |
| *A61K 9/00* | (2006.01) | |
| *A61L 27/52* | (2006.01) | |

(52) U.S. Cl.
CPC .......... *A61K 31/455* (2013.01); *A61K 9/0024* (2013.01); *A61L 27/52* (2013.01); *A61P 29/00* (2018.01); *A61L 2400/06* (2013.01)

(58) Field of Classification Search
CPC ..... A61P 29/00; A61K 31/221; A61K 31/455; A61K 31/465; A61K 39/395; A61K 47/34; A61K 9/0024; A61K 9/06; A61L 2400/06; A61L 27/52
See application file for complete search history.

(56) References Cited

U.S. PATENT DOCUMENTS

| | | | |
|---|---|---|---|
| 2,339,482 A | 1/1944 | Huttkay | |
| 2,339,846 A | 1/1944 | Du Bois et al. | |
| 4,029,793 A | 6/1977 | Adams et al. | |
| 4,582,865 A | 4/1986 | Balazs et al. | |
| 4,601,169 A | 7/1986 | Hesse et al. | |
| 5,279,825 A | 1/1994 | Wehling | |
| 6,152,943 A | 11/2000 | Sawhney | |
| 6,165,201 A | 12/2000 | Sawhney et al. | |
| 6,179,862 B1 | 1/2001 | Sawhney | |
| 6,379,373 B1 | 4/2002 | Sawhney et al. | |
| 6,514,534 B1 | 2/2003 | Sawhney | |
| 6,545,067 B1 | 4/2003 | Büchner et al. | |
| 6,566,406 B1 | 5/2003 | Pathak et al. | |
| 6,605,294 B2 | 8/2003 | Sawhney | |
| 6,610,713 B2 * | 8/2003 | Tracey ................. | A61K 31/44 514/343 |
| 6,629,969 B2 * | 10/2003 | Chan ..................... | A61L 29/16 604/500 |
| 6,632,457 B1 | 10/2003 | Sawhney | |
| 6,673,093 B1 | 1/2004 | Sawhney | |
| 6,676,675 B2 | 1/2004 | Mallapragada et al. | |
| 6,689,148 B2 | 2/2004 | Sawhney et al. | |
| 6,703,047 B2 | 3/2004 | Sawhney et al. | |
| 6,746,464 B1 | 6/2004 | Makower | |
| 6,818,018 B1 | 11/2004 | Sawhney | |
| 6,887,974 B2 | 5/2005 | Pathak | |
| 6,932,971 B2 | 8/2005 | Bachmann et al. | |
| 6,937,896 B1 | 8/2005 | Kroll | |
| 7,009,034 B2 | 3/2006 | Pathak et al. | |
| 7,025,990 B2 | 4/2006 | Sawhney | |
| 7,057,019 B2 | 6/2006 | Pathak | |
| 7,211,651 B2 | 5/2007 | Pathak | |

(Continued)

FOREIGN PATENT DOCUMENTS

| | | |
|---|---|---|
| CA | 2 351 787 A1 | 12/2001 |
| CN | 1682693 A | 10/2005 |

(Continued)

OTHER PUBLICATIONS

Van Maanen (Nature Reviews, Rheumatology, Apr. 5, 2009, 229-232) (Year: 2009).*
Pai (Medscape, 2014, p. 1-6). (Year: 2014).*
U.S. Appl. No. 15/140,254 (U.S. Pat. No. 9,855,317), filed Apr. 27, 2016 (Jan. 2, 2018), Systems and Methods for Sympathetic Cardiopulmonary Neuromodulation.
U.S. Appl. No. 15/848,518, filed Dec. 20, 2017, Systems and Methods for Sympathetic Cardiopulmonary Neuromodulation.
U.S. Appl. No. 16/275,120, filed Feb. 13, 2019, Systems and Methods for Cardiac Plexus Neuromodulation.
U.S. Appl. No. 16/313,856, filed Dec. 27, 2018, Treatment of Sepsis and Related Inflammatory Conditions by Local Neuromodulation of the Autonomic Nervous System.

(Continued)

*Primary Examiner* — Umamaheswari Ramachandran
(74) *Attorney, Agent, or Firm* — Knobbe Martens Olson & Bear, LLP

(57) ABSTRACT

Methods of use, formulations, and devices for delivering therapeutic drugs locally to the region of the spleen are described herein. A method for treating sepsis and other inflammatory disease conditions can include inserting a drug delivery system inside the body, advancing the device to the spleen through the splenic artery, splenic vein or other blood vessel adjacent to the splenic nerves, or within a ligament associated with the spleen, such as the splenorenal or gastrosplenic ligaments.

17 Claims, 21 Drawing Sheets

(56) References Cited

U.S. PATENT DOCUMENTS

| | | |
|---|---|---|
| 7,220,270 B2 | 5/2007 | Sawhney et al. |
| 7,332,566 B2 | 2/2008 | Pathak et al. |
| 7,347,850 B2 | 3/2008 | Sawhney |
| 7,413,752 B2 | 8/2008 | Sawhney |
| 7,592,418 B2 | 9/2009 | Pathak et al. |
| 7,597,882 B2 | 10/2009 | Pathak et al. |
| 7,605,232 B2 | 10/2009 | Pathak |
| 7,648,713 B2 | 1/2010 | Sawhney |
| 7,708,979 B2 | 5/2010 | Lowman et al. |
| 7,744,913 B2 | 6/2010 | Noyes |
| 7,772,359 B2 | 8/2010 | Pacetti |
| 7,776,063 B2 | 8/2010 | Sawhney et al. |
| 7,780,980 B2 | 8/2010 | Sawhney |
| 7,790,192 B2 | 9/2010 | Sawhney et al. |
| 7,862,538 B2 | 1/2011 | Sawhney et al. |
| 7,872,068 B2 | 1/2011 | Khosravi et al. |
| 7,914,541 B2 | 3/2011 | Sawhney et al. |
| 7,928,141 B2 | 4/2011 | Li |
| 8,003,705 B2 | 8/2011 | Sawhney et al. |
| 8,044,137 B2 | 10/2011 | Khosravi et al. |
| 8,105,622 B2 | 1/2012 | Sawhney |
| 8,175,711 B2 | 5/2012 | Demarais et al. |
| 8,206,299 B2 | 6/2012 | Foley et al. |
| 8,211,017 B2 | 7/2012 | Foley et al. |
| 8,257,723 B2 | 9/2012 | Noyes |
| 8,383,161 B2 | 2/2013 | Campbell et al. |
| 8,399,443 B2 | 3/2013 | Seward |
| 8,409,606 B2 | 4/2013 | Sawhney et al. |
| 8,465,752 B2 | 6/2013 | Seward |
| 8,470,362 B2 | 6/2013 | Sawhney et al. |
| 8,480,651 B2 | 7/2013 | Abuzaina et al. |
| 8,512,749 B2 | 8/2013 | Sawhney et al. |
| 8,535,705 B2 | 9/2013 | Pathak et al. |
| 8,557,535 B2 | 10/2013 | Pathak |
| 8,563,027 B2 | 10/2013 | Jarrett et al. |
| 8,708,995 B2 | 4/2014 | Seward et al. |
| 8,741,328 B2 | 6/2014 | Suzuki et al. |
| 8,795,709 B2 | 8/2014 | Sawhney et al. |
| 8,852,230 B2 | 10/2014 | Sawhney et al. |
| 8,852,646 B2 | 10/2014 | Campbell et al. |
| 8,916,611 B2 | 12/2014 | Roy et al. |
| 8,961,501 B2 | 2/2015 | Jarrett et al. |
| 8,986,730 B2 | 3/2015 | Sawhney et al. |
| 9,011,879 B2 | 4/2015 | Seward |
| 9,023,023 B2 | 5/2015 | McKay et al. |
| 9,125,807 B2 | 9/2015 | Sawhney et al. |
| 9,131,975 B2 | 9/2015 | McKay |
| 9,186,197 B2 | 11/2015 | McKay |
| 9,199,065 B2 | 12/2015 | Seward |
| 9,205,150 B2 | 12/2015 | Jarrett et al. |
| 9,254,267 B2 | 2/2016 | Sawhney |
| 9,308,283 B2 | 4/2016 | Campbell et al. |
| 9,358,374 B2 | 6/2016 | Dacey et al. |
| 9,370,485 B2 | 6/2016 | Sawhney et al. |
| 9,386,969 B2 | 7/2016 | Sawhney et al. |
| 9,386,990 B2 | 7/2016 | Muir et al. |
| 9,463,004 B2 | 10/2016 | Campbell et al. |
| 9,498,557 B2 | 11/2016 | Pathak et al. |
| 9,669,117 B2 | 6/2017 | Campbell et al. |
| 9,687,216 B2 | 6/2017 | Sawhney et al. |
| 9,707,000 B2 | 7/2017 | Hoke et al. |
| 9,730,986 B2 | 8/2017 | Roy et al. |
| 9,775,906 B2 | 10/2017 | Sawhney et al. |
| 9,789,161 B2 | 10/2017 | Roy et al. |
| 9,855,317 B2 | 1/2018 | Bright |
| 10,420,724 B2 | 9/2019 | Jarrett et al. |
| 10,842,494 B2 | 1/2020 | Agarwal et al. |
| 10,550,187 B2 | 2/2020 | Sawhney et al. |
| 10,675,085 B2 | 6/2020 | Clark et al. |
| 10,786,462 B2 | 9/2020 | Jarrett et al. |
| 2002/0037919 A1 | 3/2002 | Hunter |
| 2003/0152637 A1 | 8/2003 | Chasin et al. |
| 2004/0096507 A1 | 5/2004 | Kwang et al. |
| 2004/0166088 A1 | 8/2004 | Shalaby |
| 2004/0186488 A1 | 9/2004 | Droese |
| 2004/0220296 A1 | 11/2004 | Lowman et al. |
| 2005/0203206 A1 | 9/2005 | Trieu |
| 2005/0228460 A1 | 10/2005 | Levin et al. |
| 2005/0261672 A1 | 11/2005 | Deem et al. |
| 2006/0177481 A1 | 8/2006 | Sawhney |
| 2006/0184185 A1 | 8/2006 | Olausson et al. |
| 2006/0280797 A1 | 12/2006 | Shoichet et al. |
| 2006/0287678 A1 | 12/2006 | Shafer |
| 2007/0016274 A1 | 1/2007 | Boveja et al. |
| 2007/0253960 A1 | 11/2007 | Roy et al. |
| 2007/0255379 A1* | 11/2007 | Williams ............... A61N 1/05 607/120 |
| 2008/0114092 A1 | 5/2008 | Sawhney |
| 2008/0147137 A1 | 6/2008 | Cohen et al. |
| 2010/0119451 A1 | 5/2010 | Sawhney |
| 2010/0168625 A1 | 7/2010 | Swain et al. |
| 2010/0255060 A1 | 10/2010 | Kajii et al. |
| 2011/0104061 A1 | 5/2011 | Seward |
| 2012/0039862 A1 | 2/2012 | Borodic |
| 2012/0049689 A1 | 3/2012 | Bennett et al. |
| 2013/0035682 A1 | 2/2013 | Weil |
| 2013/0071462 A1 | 3/2013 | Jarrett et al. |
| 2013/0204068 A1 | 8/2013 | Gnanashanmugam et al. |
| 2013/0225664 A1 | 8/2013 | Horsager et al. |
| 2013/0274674 A1 | 10/2013 | Fischell et al. |
| 2013/0287698 A1 | 10/2013 | Seward |
| 2013/0296646 A1 | 11/2013 | Barbut et al. |
| 2013/0304174 A1 | 11/2013 | Langhals et al. |
| 2014/0052168 A1 | 2/2014 | Sawhney |
| 2014/0094932 A1 | 4/2014 | Deister et al. |
| 2014/0221975 A1 | 8/2014 | Gnanashanmugam et al. |
| 2014/0271717 A1 | 9/2014 | Goshayeshgar et al. |
| 2014/0276590 A1 | 9/2014 | Hiller et al. |
| 2014/0341836 A1 | 11/2014 | Sawhney et al. |
| 2014/0350327 A1 | 11/2014 | Poon et al. |
| 2014/0363382 A1* | 12/2014 | Campbell ............... A61L 31/18 424/9.454 |
| 2014/0363498 A1 | 12/2014 | Sawhney et al. |
| 2015/0065945 A1 | 3/2015 | Zarins et al. |
| 2015/0132409 A1* | 5/2015 | Stein ............... A61K 45/06 424/665 |
| 2015/0305799 A1 | 10/2015 | Trieu |
| 2015/0374887 A1 | 12/2015 | Romero-Ortega et al. |
| 2016/0045602 A1 | 2/2016 | Jarrett et al. |
| 2016/0106587 A1 | 4/2016 | Jarrett et al. |
| 2016/0166504 A1 | 6/2016 | Jarrett et al. |
| 2016/0296623 A1 | 10/2016 | Sawhney et al. |
| 2016/0331738 A1 | 11/2016 | Jarrett et al. |
| 2016/0367235 A1 | 12/2016 | Campbell et al. |
| 2017/0020729 A1 | 1/2017 | Jarrett et al. |
| 2017/0143409 A1 | 5/2017 | Clark et al. |
| 2017/0266324 A1 | 9/2017 | Campbell et al. |
| 2018/0147260 A1 | 5/2018 | Bright |
| 2018/0185390 A1 | 7/2018 | Eviston et al. |
| 2019/0038646 A1 | 2/2019 | Bright et al. |
| 2019/0216899 A1 | 7/2019 | Bright |
| 2020/0206365 A1 | 7/2020 | Campbell et al. |
| 2020/0206366 A1 | 7/2020 | Campbell et al. |
| 2020/0206367 A1 | 7/2020 | Campbell et al. |
| 2020/0207860 A1 | 7/2020 | Sawhney et al. |
| 2021/0046221 A1 | 2/2021 | Deister |

FOREIGN PATENT DOCUMENTS

| | | |
|---|---|---|
| CN | 102125516 A | 7/2011 |
| CN | 103385850 A | 11/2013 |
| CN | 103750919 A | 4/2014 |
| CN | 103816111 A | 5/2014 |
| CN | 104069485 A | 10/2014 |
| CN | 104288091 A | 1/2015 |
| CN | 104399131 A | 3/2015 |
| CN | 109395165 A | 3/2019 |
| JP | 2000-139976 | 5/2000 |
| JP | 5453776 B2 | 3/2014 |
| RU | 2582226 C1 | 4/2016 |
| WO | WO 2001/089526 | 11/2001 |
| WO | WO 2004/002449 | 1/2004 |
| WO | WO 2009/146030 | 12/2009 |
| WO | WO 2011/085166 | 7/2011 |

(56) References Cited

FOREIGN PATENT DOCUMENTS

| WO | WO 2012/075337 | | 6/2012 | | |
|---|---|---|---|---|---|
| WO | WO 2013/165714 | | 11/2013 | | |
| WO | WO 2014/130419 | | 8/2014 | | |
| WO | WO-2016019000 | A1 * | 2/2016 | ............ | A61K 45/06 |
| WO | WO 2016/144166 | | 9/2016 | | |
| WO | WO 2016/176333 | | 11/2016 | | |
| WO | WO 2017/139487 | | 8/2017 | | |
| WO | WO 2018/005848 | | 1/2018 | | |
| WO | WO 2018/125822 | | 7/2018 | | |
| WO | WO 2019/027272 | | 2/2019 | | |
| WO | WO 2019/178564 | | 9/2019 | | |
| WO | WO 2020/010123 | | 1/2020 | | |
| WO | WO 2020/010164 | | 1/2020 | | |

OTHER PUBLICATIONS

U.S. Appl. No. 16/076,308, filed Aug. 7, 2018, Methods, Agents, and Devices for Local Neuromodulation of Autonomic Nerves.

U.S. Appl. No. 16/981,199, filed Sep. 15, 2020, Systems and Methods for Gel-Based Neuromodulation.

U.S. Appl. No. 17/257,266, filed Dec. 30, 2020, Systems and Methods for Visceral Neuromodulation.

U.S. Appl. No. 17/138,703, filed Dec. 30, 2020, Methods and Devices for In Situ Formed Nerve Cap.

U.S. Appl. No. 17/148,427, filed Jan. 13, 2021, Methods and Devices for In Situ Formed Nerve Cap With Rapid Release.

Abbott, O. A., W. A. Hopkins, et al. (1950). "Therapeutic status of pulmonary autonomic nerve surgery." J Thorac Surg 20(4): 571-83; passim.

Abdi, Salahadin, et al. "A new and easy technique to block the stellate ganglion." Pain Physician 7.3 (2004): 327-332.

Adar, R., A. Kurchin, et al. (1977). "Palmar hyperhidrosis and its surgical treatment: a report of 100 cases." Ann Surg 186(1): 34-41.

Albers, James, et al. "Interventions for preventing neuropathy caused by cisplatin and related compounds." Cochrane Database Syst Rev 1.1 (2007).

Antila, H., and O. Kirvelä. "Neurolytic thoracic paravertebral block in cancer pain." Acta anaesthesiologica scandinavica 42.5 (1998): 581-585.

Antolak SJ, et al. "Therapeutic Pudendal Nerve Blocks Using Corticosteriods Cure Pelvic Pain after Failure of Sacral Neuromodulation" Pain Medicine 2009, vol. 10, No. 1, pp. 185-189.

B Braun Plexus Anaesthesia product guide (2014) in 10 pages.

Baumgartner, F. J. (2008). "Surgical approaches and techniques in the management of severe hyperhidrosis." Thorac Surg Clin 18(2): 167-81.

Baumgartner, Fritz J., et al. "Thoracoscopic sympathicotomy for disabling palmar hyperhidrosis: a prospective randomized comparison between two levels." The Annals of thoracic surgery 92.6 (2011): 2015-2019.

BD PuraMatrix Peptide Hydrogel Brochure (2004) in 4 pages.

Blades, B., E. J. Beattie, Jr., et al. (1950). "The surgical treatment of intractable asthma." J Thorac Surg 20(4): 584-91; passim.

Boezaart, André P. Atlas of peripheral nerve blocks and anatomy for orthopaedic anesthesia. Elsevier Health Sciences, p. 218, 2008.

Bolderman et al., International Journal of Cardiology, 2011, 149, p. 341-346 (Year: 2011).

Cai, "Injectable glycosaminoglycan hydrogels for controlled release of human basic fibroblast growth factor" Biomaterials 26 (2005) 6054-6067 (Year: 2005).

Carli, Mirjana, et al. "Tph2 gene deletion enhances amphetamine-induced hypermotility: effect of 5-HT restoration and role of striatal noradrenaline release." Journal of neurochemistry 135.4 (2015): 674-685.

Carr, D. and H. Chandler (1948). "Dorsal sympathetic ganglionectomy for intractable asthma." J Thorac Surg 17(1): 1-12.

Chaibundit, Chiraphon, et al. "Effect of ethanol on the gelation of aqueous solutions of Pluronic F127." Journal of colloid and interface science 351.1 (2010): 190-196.

Chaibundit, Chiraphon, et al. "Effect of Ethanol on the Micellization and Gelation of Pluronic P123." Langmuir 24.21 (2008): 12260-12266.

Chang, Jason Y., Kevin D. Phelan, and Janet A. Chavis. "Neurotoxicity of 25-OH-cholesterol on sympathetic neurons." Brain research bulletin 45.6 (1998): 615-622.

Cheema, S., J. Richardson, and P. McGurgan. "Factors affecting the spread of bupivacaine in the adult thoracic paravertebral space." Anaesthesia 58.7 (2003): 684-687.

Cressman, Erik NK, and David A. Jahangir. "Dual mode single agent thermochemical ablation by simultaneous release of heat energy and acid: hydrolysis of electrophiles." International Journal of Hyperthermia 29.1 (2013): 71-78.

Cunningham, D. J. (1913). Cunningham's Textbook of Anatomy, William Wood (648-734).

Da Rocha, R. P., A. Vengjer, et al. (2002). "Size of the collateral intercostal artery in adults: anatomical considerations in relation to thoracocentesis and thoracoscopy." Surg Radiol Anat 24(1): 23-6.

Denby, Christine, et al. "Temporary sympathectomy in chronic refractory angina: a randomised, double-blind, placebo-controlled trial." British journal of pain 9.3 (2015): 142-148.

Dimitrov-Szokodi, D., G. Balogh, et al. (1957). "Lung denervation in the therapy of intractable bronchial asthma." J Thorac Surg 33(2): 166-84.

Downing, S. Evans, and John C. Lee. "Nervous control of the pulmonary circulation." Annual Review of Physiology 42.1 (1980): 199-210.

Drott, C. and G. Claes (1996). "Hyperhidrosis treated by thoracoscopic sympathicotomy." Cardiovasc Surg 4(6): 788-90; discussion 790-1.

Dumont, Pascal. "Side effects and complications of surgery for hyperhidrosis." Thoracic surgery clinics 18.2 (2008): 193-207.

Dun, N. J., and A. G. Karczmar. "Evidence for a presynaptic inhibitory action of 5-hydroxytryptamine in a mammalian sympathetic ganglion." Journal of Pharmacology and Experimental Therapeutics 217.3 (1981): 714-718.

Evicore. Clinical Guidelines. Aug. 11, 2017. [Retrieved Sep. 3, 2019] Retrieved from online URL: https://www.evicore.com/-/media/files/evicore/clinical-guidelines/solut1on /m sk-advance/archive/cmm-207---oain-eoidural-adhesiolvsiseffOB1117 102118.pdf.

Extended European Search Report in Application No. 17821282.5, dated Mar. 6, 2020, in 9 pages.

Feinberg, Samuel M. "Progress in Asthma: Literature for 1934 and 1935." Journal of Allergy 7.3 (1936): 268-294.

Finucane 2017, "complications of regional anesthesia" published by Springer, 2017 p. 213.

Fredman, B., E. Zohar, et al. (2000). "Video-assisted transthoracic sympathectomy in the treatment of primary hyperhidrosis: friend or foe?" Surg Laparosc Endosc Percutan Tech 10(4): 226-9.

Freeman, N. E., R. H. Smithwick, et al. (1934). "Adrenal Secretion in Man." Am. J. Physiol. 107(3): 529.

http://www.fziomed.com/core-science/ web page last updated Aug. 19, 2016 in 2 pages.

Garcia-Morales, Luis et al., "Intraoperative Surgical Sealant Application during Cardia Defect Repair", Texas Heart Institute Journal, vol. 41, No. 4, Aug. 1, 2014, pp. 440-442.

Gay, L. N. and W. M. Reinhoff (1934). "Further Observations on the Treatment of Intractable Bronchial Asthma by Bilateral Resection of the Pulmonary Plexus." J. Allergy 13(6): 626-631.

Gloor et al., J Clin Invest., 1983, 71(5), p. 1457-1466 (Year: 1983).

Gossot, D., H. Kabiri, et al. (2001). "Early complications of thoracic endoscopic sympathectomy: a prospective study of 940 procedures." Ann Thorac Surg 71(4): 1116-9.

Gossot, D., L. Toledo, et al. (1997). "Thoracoscopic sympathectomy for upper limb hyperhidrosis: looking for the right operation." Ann Thorac Surg 64(4): 975-8.

Haam, Seokjin, et al. "An anatomical study of the relationship between the sympathetic trunk and intercostal veins of the third and fourth intercostal spaces during thoracoscopy." Clinical Anatomy 23.6 (2010): 702-706.

Hayakawa, Kazuhiro, et al. "Nerve growth factor prevention of aged-rat sympathetic neuron injury by cisplatin, vincristine and taxol—in vitro explant study." Neuroscience letters 274.2 (1999): 103-106.

(56) References Cited

OTHER PUBLICATIONS

Hsu, C. P., C. Y. Chen, et al. (1998). "Resympathectomy for palmar and axillary hyperhidrosis." Br J Surg 85(11): 1504-5.

Huang, B., et al. "[Therapeutic feasibility of percutaneous puncture and chemical neurolysis of thoracic sympathetic nerve block in palmar hyperhidrosis under the guidance of computed tomograph]." Zhonghua yi xue za zhi 91.38 (2011): 2710-2713.

Ilfeld, et al. "Ultrasound-guided Percutaneous Peripheral Nerve Stimulation for Analgesia Following Total Knee Arthroplsaty: a Prospective Feasibility Study" Journal of Orthopaedic Surgery and Research 2017, vol. 12, No. 4, pp. 1-9.

Imrich, Richard, et al. "Functional effects of cardiac sympathetic denervation in neurogenic orthostatic hypotension." Parkinsonism & related disorders 15.2 (2009): 122-127.

Ireland, S. J., and C. C. Jordan. "Pharmacological characterization of 5-hydroxytryptamine-induced hyperpolarization of the rat superior cervical ganglion." British journal of pharmacology 92.2 (1987): 417-427.

Ischemia. Wikipedia. Dec. 24, 2017. [Retrieved Sep. 3, 2019] Retrieved from online URL:https://en.wikipedia.org/w/index.php?title=Ischemia&oldid=816854406.

Karmakar, M. K., T. Gin, and AM-H. Ho. "Ipsilateral thoracolumbar anaesthesia and paravertebral spread after low thoracic paravertebral injection." British journal of anaesthesia 87.2 (2001): 312-316.

Kaur, Gurjinder, et al. "Estrogen regulation of neurotrophin expression in sympathetic neurons and vascular targets." Brain research 1139 (2007): 6-14.

Kimura, Tomohiko, Toshitake Shimamura, and Susumu Satoh. "Effects of pirenzepine and hexamethonium on adrenal catecholamine release in responses to endogenous and exogenous acetylcholine in anesthetized dogs." Journal of cardiovascular pharmacology 20.6 (1992): 870-874.

Klodell, Charles T., et al. "Oximetry-derived perfusion index for intraoperative identification of successful thoracic sympathectomy." The Annals of thoracic surgery 80.2 (2005): 467-470.

Koyama et al., Circ. J., 2002, 66, p. 645-648 (Year: 2002).

Krediet, Annelot C., et al. "Different Approaches to Ultrasound-guided Thoracic Paravertebral BlockAn Illustrated Review." The Journal of the American Society of Anesthesiologists 123.2 (2015): 459-474.

Lee, Ju Young, et al. "In vivo efficacy of paclitaxel-loaded injectable in situ-forming gel against subcutaneous tumor growth." International journal of pharmaceutics 392.1 (2010): 51-56.

Lee, Sang Beom, et al. "Morphometric Study of the Upper Thoracic Sympathetic Ganglia." Journal of Korean Neurosurgical Society 50.1 (2011): 30-35.

Levin, G. L. (1935). "The Treatment of Bronchial Asthma by Dorsal Sympathectomy: Direct and Indirect." Ann Surg 102(2): 161-70.

Li, et al. "Controlled Release of Protein from Biodegradable Mutio-Senstitive Injectable Poly (ether-urethane) Hydrogel" ACS Appl. Mater. Interfaces 2014, vol. 6, No. 5, pp. 3640-3647.

Lin K L et al. "DuraSeal as a Ligature in the Anastomosis of rat Sciatic Nerve Gap Injury", Journal of Surgical Research, Academic Press Inc. San Diego CA US, vol. 161, No. 1, Jun. 1, 2010, pp. 101-110.

Lin, Zhiqiang, et al. "Novel thermo-sensitive hydrogel system with paclitaxel nanocrystals: High drug-loading sustained drug release and extended local retention guaranteeing better efficacy and lower toxicity." Journal of Controlled Release 174 (2014): 161-170.

Liu, et al, 2009, European J of Cariothoracic Surgery, 35, 398-402.

Macaya, D., and M. Spector. "Injectable hydrogel materials for spinal cord regeneration: a review." Biomedical materials 7.1 (2012): 012001.

Mahajan, Mohit, P. Utreja, and S. K. Jain. "Paclitaxel Loaded Nanoliposomes in Thermosensitive Hydrogel: A Dual Approach for Sustained and Localized Delivery." Anti-cancer agents in medicinal chemistry (2015).

Malik, Tariq. "Ultrasound-Guided Paravertebral Neurolytic Block: A Report of Two Cases." Pain Practice 14.4 (2014): 346-349.

Marinescu, Mark A., et al. "Coronary microvascular dysfunction, microvascular angina, and treatment strategies." JACC: Cardiovascular Imaging 8.2 (2015): 210-220.

Matchett, Gerald. "Intercostal Nerve Block and Neurolysis for Intractable Cancer Pain." Journal of Pain & Palliative Care Pharmacotherapy (2016): 1-4.

Mehdizadeh, Mohammadreza, and Jian Yang. "Design strategies and applications of tissue bioadhesives." Macromolecular bioscience 13.3 (2013): 271-288.

Microstimulation. Wikipedia. Jun. 30, 2016. [Retrieved Sep. 3, 2019) Retrieved from online URL:https://en.wikipedia.org/w/index.php?title=Microstimulation&oldid=727594711.

Moawad, H. M. M., and H. Jain. "Development of nano-macroporous soda-lime phosphofluorosilicate bioactive glass and glass-ceramics." Journal of Materials Science: Materials in Medicine 20.7 (2009): 1409-1418.

Murray, Gary L., and Joseph Colombo. "Ranolazine preserves and improves left ventricular ejection fraction and autonomic measures when added to guideline-driven therapy in chronic heart failure." Heart International 9.2 (2014): 66-73.

Naja, M. Z., et al. "Varying anatomical injection points within the thoracic paravertebral space: effect on spread of solution and nerve blockade." Anaesthesia 59.5 (2004): 459-463.

Ng, Ivan, and Tseng-Tsai Yeo. "Palmar hyperhidrosis: intraoperative monitoring with laser Doppler blood flow as a guide for success after endoscopic thoracic sympathectomy." Neurosurgery 52.1 (2003): 127-131.

Nunn, J. F., and G. Slavin. "Posterior intercostal nerve block for pain relief after cholecystectomy anatomical basis and efficacy." British journal of anaesthesia 52.3 (1980): 253-260.

Ostermann Pa et al. "The ligament system of the spleen and its significance for surgical interventions" Langenbecks Arch Chir 1987;371 (3):207-16, abstract.

Pandin, Pierre, Samia Rettab, and Alphonse Lubansu. "Ultrasound Guidance Is Helpful for Paravertebral Block Performance and Catheter Placement in Patients with Laminectomy after Thoracotomy or Lumbotomy: A Case Series Imaging Study." (2013).

Paredi, P. and P. J. Barnes (2009). "The airway vasculature: recent advances and clinical implications." Thorax 64(5): 444-50.

Parlato, Matthew, et al. "Adaptable poly (ethylene glycol) microspheres capable of mixed-mode degradation." Acta biomaterialia 9.12 (2013): 9270-9280.

Phillips, E. W. and W. J. M. Scott (1929). "The Surgical Treatment of Bronchial Asthma." Arch Surg. 19(6): 1425-1456.

Pierce, Nathan E. et al, "Hydrogel sutureless facial nerve repair: Pilot Clinical Investigation: Sutureless Facial Nerve Repair", The Laryngoscope, Jun. 2015. vol. 125, No. 6, First Published, Dec. 4, 2014, pp. 1456-1459.

Ponce Gonzalez, M. A., G. J. Serda, et al. (2005). "Long-term pulmonary function after thoracic sympathectomy." The Journal of Thoracic and Cardiovascular Surgery 129(6): 1379-1382.

Richardson and Lonnqvist, (1998) "Thoracic Paravertebral Block" British Journal of Anaesthesia 81: 230-238.

Rienhoff WF Jr, G. L. (1938). "Treatment of Intractable Bronchial Asthma by Bilateral Resection of the Posterior Pulmonary Plexus." Arch Surg. 37(3): 456-469.

Riquet, M. (2007). "Bronchial arteries and lymphatics of the lung." Thorac Surg Clin 17(4): 619-38, viii.

Robinson, Eric A., et al. "Estimating sympathetic tone by recording subcutaneous nerve activity in ambulatory dogs." Journal of cardiovascular electrophysiology 26.1 (2015): 70-78.

Rongen, Gerard A., et al. "Presynaptic inhibition of norepinephrine release from sympathetic nerve endings by endogenous adenosine." Hypertension 27.4 (1996): 933-939.

Rosas-Ballina, et al., "Cholingergic control of inflammation" J. Intern Med. Jun. 2009; 265(6): 663-679.

Shvaichak E. Zavisimost vyazkosti vodnogo rastvora gialuronovoi kisloty ot ee mikrostruktury. Chast 1. Rossysky zhurnal biomekhaniki, tom 7, No. 3: 87•98, 2003.

Singh, Narendra K., and Doo Sung Lee. "In situ gelling pH- and temperature-sensitive biodegradable block copolymer hydrogels for drug delivery." Journal of Controlled Release 193 (2014): 214-227.

(56) References Cited

OTHER PUBLICATIONS

Takatori, Mayumi, Yoshihiro Kuroda, and Munetaka Hirose. "Local anesthetics suppress nerve growth factor-mediated neurite outgrowth by inhibition of tyrosine kinase activity of TrkA." Anesthesia & Analgesia 102.2 (2006): 462-467.
Vallieres, E. (2007). "The costovertebral angle." Thorac Surg Clin 17(4): 503-10.
Van der Velden, Vincent HJ, and Anthon R. Hulsmann. "Autonomic innervation of human airways: structure, function, and pathophysiology in asthma." Neuroimmunomodulation 6.3 (1999): 145-159.
Vanaclocha, V., N. Saiz-Sapena, et al. (2000). "Uniportal endoscopic superior thoracic sympathectomy." Neurosurgery 46(4): 924-8.
Vida, Gergely, et al., "α7-Cholinergic Receptor Mediates Vagal Induction of Splenic Norepinephrine", *J Immunol* 2011; 186:4340-4346; Prepublished online Feb. 21, 2011.
Vida, Gergely, et al., "β2-Adrenoreceptors of regulatory lymphocytes are essential for vagal neuromodulcation of the innate immune system", The FASEB Journal, vol. 25, Dec. 2011, pp. 4476-4485.
Wallace D G et al., "A tissue sealant based on reactive multifunctional polyethylene glycol", Journal of BioMedical Materials Research, Wiley, New York, NY US. vol. 58, No. 5, Apr. 25, 2015 pp. 545-555.
Wang, Peizong, et al. "Antinociceptive effect of intrathecal amiloride on neuropathic pain in rats." Neuroscience letters 604 (2015): 24-29.
Wang, William et al.: "Clinical efficacy of epicardial application of drug-releasing hydrogels to prevent postoperative atrial fibrillation", Journal of thoracic and Cardiovascular Surgery, vol. 151, No. 1, First read: Apr. 25, 2015, pp. 80-85.
Weksler et al, 2008, Thorac Surg Clin, 18, 183-191.
Westerlund, Taina, Ville Vuorinen, and Matias Röyttä. "The perineurium modifies the effects of phenol and glycerol in rat sciatic nerve." Acta neuropathologica 108.4 (2004): 319-331.
Wilensky, H. M. (1940). "Peri-Sympathetic Injection Treatment of Asthma." Can Med Assoc J 43(1): 59-62.
Xu, Xian, et al. "Hyaluronic acid-based hydrogels: from a natural polysaccharide to complex networks." Soft matter 8.12 (2012): 3280-3294.
Yahagi, Naoki, Tsuyoshi Akiyama, and Toji Yamazaki. "Effects of ω-conotoxin GVIA on cardiac sympathetic nerve function." Journal of the autonomic nervous system 68.1 (1998): 43-48.
Yamazaki, Toji, Tsuyoshi Akiyama, and Toru Kawada. "Effects of ouabain on in situ cardiac sympathetic nerve endings." Neurochemistry international 35.6 (1999): 439-445.
Yohn, Samantha E., et al. "Not all antidepressants are created equal: differential effects of monoamine uptake inhibitors on effort-related choice behavior." Neuropsychopharmacology (2015).
Zarse, Markus, et al. "Selective increase of cardiac neuronal sympathetic tone: a catheter-based access to modulate left ventricular contractility." Journal of the American College of Cardiology 46.7 (2005): 1354-1359.
Zhang, Hongling, and Javier Cuevas. "Sigma Receptors Inhibit High-Voltage-Activated Calcium Channels in Rat Sympathetic and Parasympathetic Neurons." Journal of neurophysiology 87.6 (2002): 2867-2879.
Zhao, Ying-Zheng, et al. "Using NGF heparin-poloxamer thermosensitive hydrogels to enhance the nerve regeneration for spinal cord injury." Acta biomaterialia 29 (2016): 71-80.

* cited by examiner

TREATMENT OF SEPSIS AND RELATED INFLAMMATORY CONDITIONS BY LOCAL NEUROMODULATION OF THE AUTONOMIC NERVOUS SYSTEM

INCORPORATION BY REFERENCE TO ANY PRIORITY APPLICATIONS

This application is the U.S. National Stage of PCT App. No. PCT/US2017/040074 filed on Jun. 29, 2017, which in turn claims the benefit under 35 U.S.C. § 119(e) as a nonprovisional application of U.S. Prov. App. No. 62/355,889 filed on Jun. 29, 2016. Each of the foregoing are hereby incorporated by reference in their entireties.

FIELD OF THE INVENTION

Some aspects of the invention relate to methods, drugs and their formulations to modulate the immune system, particularly for the treatment of life-threatening inflammatory disease, are described.

BACKGROUND

Sepsis is a major public health issue and one of the most frequent causes of death in hospitalized patients. It is a clinical syndrome of physiologic, pathologic and biochemical abnormalities induced by infection or injury. Recent publications in the Journal of the American Medical Association (JAMA) indicate that in-hospital mortality rates in infected patients are alarmingly high ranging between 18-54%. Patients that survive sepsis can suffer physical and cognitive impairment, which can more than double their 5-year mortality risk, compared to hospitalized controls.

Nearly a million people are affected by sepsis annually in the United States and over 200,000 people die, placing a significant burden on the healthcare system. Estimates suggest that over $20 billion were spent in 2011 on sepsis-related intensive care unit (ICU) hospitalizations, which represents 5.2% of the total US hospital costs.

The cellular and molecular mechanisms influencing pathogenesis of sepsis are not well understood. It affects all age groups irrespective of race, gender, geography, or health status. Sepsis develops in patients affected by an infection or tissue injury from noninfectious sources such as pancreatitis, ischemia reperfusion injury, cancer, and a host of other disorders that are inflammatory in nature. The host immunological response and reaction to infection and injury plays an equally important role in the restoration or deterioration of organ function. There are no reliable diagnostic blood markers or cellular markers in organs or tissue for the detection of sepsis. Common symptoms include fever, increased respiratory rate, increased heart rate, lethargy, edema, confusion and low blood pressure.

Antibiotics and intravenous fluids (fluid replacement therapy) are used to treat septic patients in the intensive care unit. Mechanical ventilation and dialysis are used to assist respiratory and kidney function. Medications like vasopressin may be used to control blood pressure. The use of corticosteroids is controversial and treatment using the drug drotrecogin-alfa has not been effective and the drug has been withdrawn from the market. No FDA-approved drugs are available for the treatment of sepsis. Current mortality rates from sepsis, severe sepsis and septic shock conditions are currently about 30%, 50% and 80%, respectively.

Newer device-based treatments using vagus nerve stimulation (VNS), noninvasive therapeutic ultrasound delivery, and membrane filters are in development. Electrical stimulation of the vagus nerve has been shown to activate the splenic release of acetylcholine and suppress pro-inflammatory cytokine release via the brain-immune cholinergic anti-inflammatory pathway (CAP) and treat sepsis in animal models. Non-invasive ultrasound treatment, before renal ischemic reperfusion injury (IRI), also has been found to stimulate CAP in rats and protect the kidney. Hollow-fiber dialysis and cytopheretic membrane filters, which bind and sequester the activated leukocytes from blood circulation, have been clinically tested in septic patients.

All these methods have significant limitations. VNS requires the surgical implantation of an expensive electrical generator and placement of electrodes in critically-ill patients. Also, VNS may result in unwanted side effects when delivered at the cervical level because branches innervate many off-target organs. A randomized clinical study in experimental endotoxemia failed to show a similar reduction in cytokines as had been observed in preclinical studies. Non-invasive ultrasound energy treatment is not targeted and may damage surrounding tissue. Finally, the cytopheretic device therapy also did not show clinical benefit beyond small open-label clinical studies.

We describe in some embodiments therapeutic drugs, compositions and methods of administration that can overcome these limitations. The spleen is one of the largest secondary lymphoid tissues and plays a significant role in the neuro-immune axis of inflammation and maintaining immune homeostasis. Nerve signaling through the splenic nerve and its branches may modulate the production of cytokines and may activate other molecular pathways that indirectly lead to inflammation and symptoms consistent with sepsis. Methods described in some embodiments of the invention provide a treatment strategy for sepsis by the administration of a drug to alter the pro- and anti-inflammatory neuro-immune signaling pathways between the spleen and the brain. Other methods described herein disclose the treatment of a patient having symptoms consistent with sepsis by the administration of drug to an organ containing primary or secondary lymphoid tissues. In addition, some embodiments of the invention describe methods to access points of innervation between an organ containing lymphoid tissue and the brain, verify the nerve site and measure the splenic nerve signals before, during and after treatment. Specific drugs, compositions and formulations are also described.

SUMMARY

Methods of use, formulations, and devices for delivering therapeutic drugs locally to the region of the spleen are described herein. In one embodiment, a method for treating sepsis and other inflammatory disease conditions comprises inserting a drug delivery system inside the body, advancing the device to the spleen through the splenic artery, splenic vein or other blood vessel adjacent to the splenic nerves. In one embodiment, the drug delivery system is advanced next to the splenic nerve and the splenic nerve activity may be measured at the target tissue site before a small volume of therapeutic formulation is administered locally to the splenic nerve and nerve branches, related nerve plexi or ganglia to stimulate, modulate or alter neuro-immune activity. The change in splenic nerve activity may be measured to assess treatment effect prior to the delivery device removal from the body. In some embodiments, the nerve activity may be attenuated to achieve the desired immune response and maintain immune homeostasis.

In yet another embodiment, the drug delivery therapy can be advanced through the vasculature beyond the hilum into one or more post-hilum segments of the spleen prior to injecting the drug delivery system more distally. The drug delivery system may target the delivery of drugs to the postganglionic catecholaminergic neurons innervating the spleen or to target immune cells in the spleen directly. Drug delivery systems may be delivered in a formulation that can be administered into the blood vessels such that the system(s) are sequestered in the vasculature until the drug is released and the carrier cleared from the site. Alternatively, drug delivery systems may be delivered transvascularly via a drug delivery microcatheter into the spleen itself in order to achieve this. In yet another embodiment, a drug coated balloon is deployed within the splenic vasculature to deliver drug transarterially or transvenously. In yet another embodiment, a bioerodible stent is placed in the vasculature to deliver drug both transvascularly and into the blood stream distal to the site of placement.

In comparison to conventional intravenous therapy, the drug may be pre-loaded and delivered through a catheter, needle-syringe system or pump and wherein drug may be administered in a manner that perfuses the organ directly to provide for a more rapid intervention. In one embodiment, the drug is delivered from a drug delivery catheter placed in the splenic artery directly through the arterial system to the spleen. By administering the drug formulation prior to the splenic artery branching into terminal branches, the entire organ, such as the spleen may be bathed in the drug in this manner. If the drug is coated on or encapsulated within nanoparticle or microparticles, these nano- and micro-particles will course through the vasculature where they may either get trapped in a progressively smaller arteriole or capillary or alternatively extravasate into the splenic tissue. In this manner, sustained release formulations of agents can be delivered locally into the spleen.

Drug may be administered near organ innervation nodes, for example the splenic nerves, directly or may be mixed with excipients and polymers to provide sustained drug release over time to stimulate nerves or permanently affect nerve function to have durable treatment effects lasting a few days to several weeks.

The neuromodulatory effects of drug compositions described below may stimulate or upregulate nerve activity to enhance or inhibit the release of anti- or pro-inflammatory cytokines, alter the host immune response to inflammation, and maintain immune homeostasis. Other effects of blocking nerves and attenuating or downregulating nerve activity to enhance or inhibit the release of anti- or pro-inflammatory cytokines, over short or long periods of time, are also described.

Methods and devices for accessing the splenic nerve and other nerve targets involved in the brain-immune pathway are also described. The application also describes methods for visualizing nerves and measuring local autonomic activity before locally administering the drug formulation near the splenic nerve; and monitoring nerve feedback during and after treatment.

Methods described here may in some cases be used either as an adjunctive treatment to therapies currently in clinical practice or therapies under investigation to treat sepsis and other inflammatory disorders or medical conditions. Treatments described here may be performed before or after the primary procedure to allow sufficient time to regulate the local and systemic hormone, cytokine and catecholamine levels to achieve optimal clinical efficacy and restore immune homeostasis.

Other nerve targets innervating other target organs inside the body and involved in neuro-immune signaling and inflammatory disorders and medical conditions are also described. Drug formulations may be injected locally at one or more target nerve sites inside the body to treat sepsis. Drug formulations may be administered at different nerve sites to achieve the desired therapeutic benefit at specific locations over the desired time periods.

In some embodiments, a method of modulating inflammation in a patient is disclosed. The method can include, for example, providing a therapeutic agent delivery system comprising at least one therapeutic agent; accessing between the folds of one or more ligaments directly connected to a splenic hilum of the patient, wherein the one or more ligaments comprise the splenorenal ligament and the gastrosplenic ligament of the patient; and delivering the therapeutic agent delivery system between the folds of the one or more ligaments.

In some embodiments, accessing between the folds of the one or more ligaments comprises: inserting a catheter into a first blood vessel; advancing the catheter into a second blood vessel (e.g., a splenic artery, splenic vein, splenic artery end branches, etc.); and penetrating a wall of the second blood vessel with a portion of the catheter to a position between the folds of the one or more ligaments. In some embodiments, accessing between the folds of the one or more ligaments includes inserting a catheter percutaneously (e.g., between ribs in some cases); and positioning the catheter between the folds of the one or more ligaments with a portion of the catheter. The one or more ligaments could include the splenorenal ligament, gastrosplenic ligament, or others. The therapeutic delivery system can be an implant delivered between the folds of the one or more ligaments, and can coil around a blood vessel in some cases. The delivery system could include, for example, microspheres, or a gel such as a hydrogel, that can be in situ cross-linking in some cases, an injectable hydrogel slurry, be biodegradable, or combinations of the foregoing.

In some embodiments, the method, e.g., delivering the therapeutic agent delivery system treats or prevents systemic inflammatory response syndrome, sepsis, septic shock, an autoimmune disease, or acute respiratory distress syndrome. The therapeutic agent could include, for example, a sympathomimetic agent, such as an alpha-1, alpha-2, alpha-nonselective, beta-1, beta-2, or beta-nonselective agonists. In some embodiments, the therapeutic agent includes a nicotinic acetylcholine receptor agonist, such as nicotine or acetylcholine, for example. Delivering the therapeutic agent delivery system can neuromodulate sympathetic and/or parasympathetic nerves, and/or cells residing in the spleen, such as immune cells, including T-cells, B-cells, macrophages, polymorphonuclear cells, eosinophils, basophils, NK cells, or other cells.

In some embodiments, a method of modulating inflammation of a patient can include accessing between the folds of one or more ligaments directly connected to a splenic hilum of the patient, wherein the one or more ligaments comprise the splenorenal ligament and the gastrosplenic ligament of the patient; and flowing a gel comprising a therapeutic agent between the folds of the one or more ligaments such that the folds of the one or more ligaments serves as a boundary and limits the spread of the gel to between the folds of the one or more ligaments.

In some embodiments, a method of modulating inflammation in a patient can include providing a therapeutic agent delivery system comprising at least one therapeutic agent;

accessing the splenic hilum of the patient; and delivering a therapeutic agent delivery system comprising a hydrogel to the splenic hilum.

In some embodiments, a system configured for modulating inflammation in a patient can include a catheter sized and configured for being positioned percutaneously within a blood vessel directly proximate and for delivering a therapeutic agent to the splenic hilum; and a first hydrogel comprising one or more of: a nicotinic acetylcholine receptor agonist and a sympathomimetic agent. A hydrogel for use modulating inflammation by delivery to the splenic hilum percutaneously or transvascularly, such as through the wall of the splenic artery, end branches thereof, or the splenic vein, directly within the folds of the splenorenal ligament or the gastrosplenic ligament of a patient can include a therapeutic agent comprising one or more of: a nicotinic acetylcholine receptor agonist and a sympathomimetic agent.

DETAILED DESCRIPTION

Figure 1:
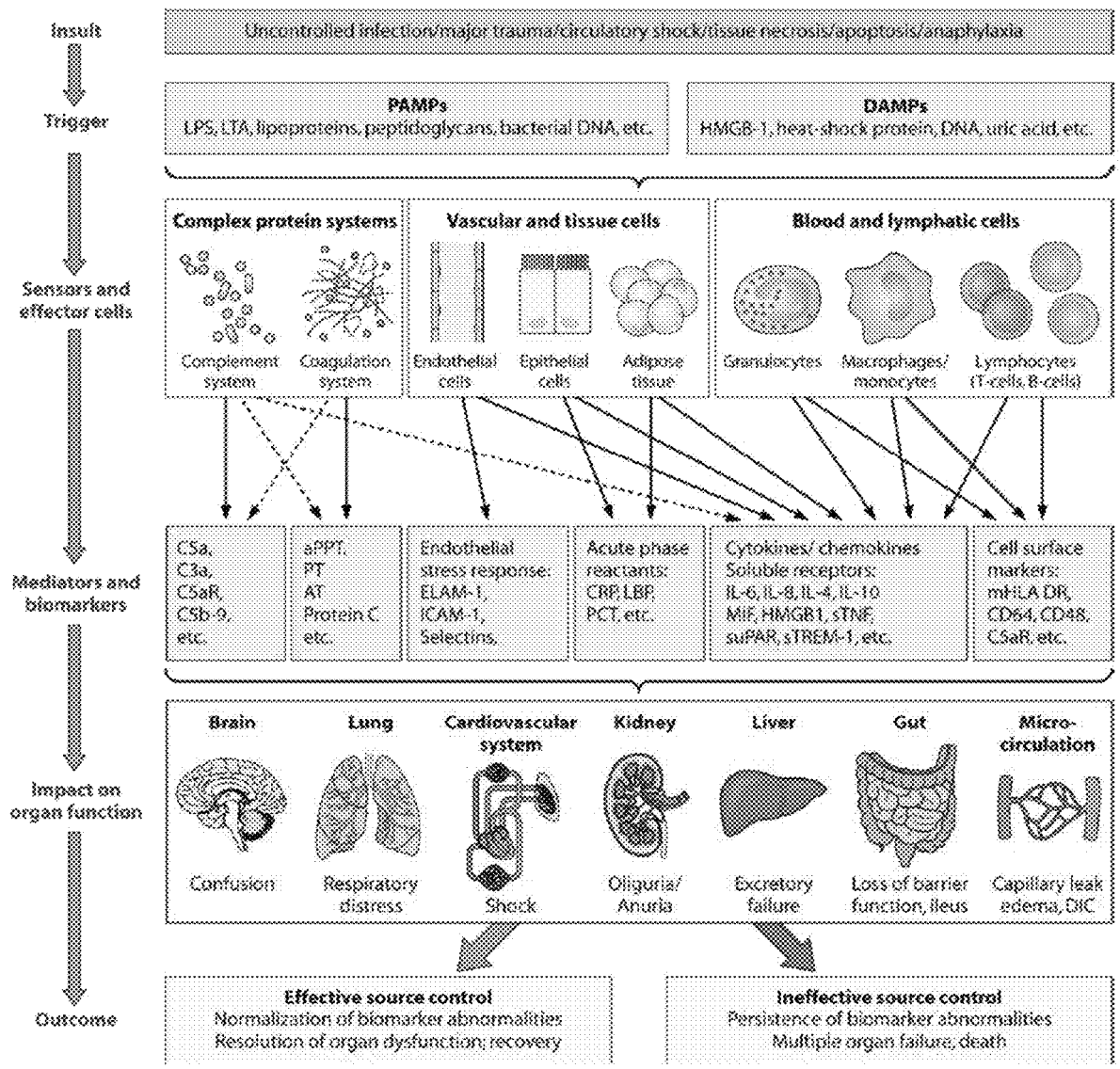
FIG. 1 shows examples of the pathways associated with injury, infection, inflammation, sepsis and resulting effects on restoring organ function or organ failure and death.

Local drug delivery systems to modulate and prevent or treat infection, trauma, injury, inflammation, sepsis, septicemia, septic shock, systemic inflammatory response syndrome (SIRS) and acute respiratory distress syndrome (ARDS) through abrogation of neuro-immune axis-specific signaling, by the administration of drug to an organ containing lymphoid tissue near the site of innervation, are described. Drug delivery systems may be injected locally near autonomic nerves innervating the spleen or other target organ to affect neuro-immune signaling and effector pathways for the treatment of inflammatory diseases. Alternatively, drug delivery systems may be injected in proximity to the effector or target cells that are modulated by the autonomic nervous system in order to directly modulate these cells. Other nerve target sites and methods to affect and improve the immune function are also described.

Methods, drugs, drug formulations and devices to treat inflammation, sepsis, septicemia, septic shock, systemic inflammatory response syndrome, acute respiratory distress syndrome and related inflammatory medical conditions through local chemical neuromodulation of the splenic nerve are described. Other nerve target sites of the autonomic nervous system, ganglia and nerve plexi inside the body that affect neuronal, neuro-immune and neuro-humoral pathways of inflammation, sepsis and related conditions to restore and preserve organ function are also described.

Sepsis and Other Inflammation-Mediated Medical Conditions

Sepsis can be considered a syndrome or a medical condition and not a disease per se. It is a life-threatening condition when the body's response to an infection injures its own tissues and organs. The pathophysiology is unknown and there are no standard diagnostic tests or blood markers for detecting sepsis. Sepsis can be identified by a set of clinical symptoms in patients with a suspected infection or injury/trauma to tissue from noninfectious sources such as pancreatitis, renal ischemia reperfusion injury (IRI), cancer, and a host of other disorders. For example, immune response after IRI contributes to renal tissue damage and reduced glomerular filtration rate (GFR) in patients that suffer acute kidney injury (AKI). The infection, host body response and organ dysfunction are the three clinical factors used to identification and treatment of sepsis. Common symptoms are fever, increased respiratory rate, increased heart rate, confusion and low blood pressure. Sepsis is the most common cause of multiple-organ failure.

Sepsis can be caused by pathogen factors and host factors. Microbes and pathogens from an infectious source invade the body and enter the bloodstream leading to signs of systemic illness. Immune response to antigens and foreign bodies involves interactions between the pro- and anti-inflammatory cytokines released through the inflammation process. Pro-inflammatory cytokines (PICs) include tumor necrosis factor (TNF-α), interleukin (IL)-1, IL-1a, IL-1b, IL-6, IL-8, IL-12, IL-18, gamma-interferon (IFN-γ), platelet-activating factor (PAF), macrophage migration inhibitory factor (MIF), granulocyte-macrophage colony stimulating factor, and high mobility group protein 1 (HMG-1). IL-4, IL-10, IL-13, alpha-interferon (IFN-a) and transforming growth factor-beta (TGF-b) are considered to be anti-inflammatory cytokines (AICs). Cytokines are produced by immune cells including, monocytes, macrophages and neutrophils, and non-immune cells such as fibroblasts, osteoblasts, smooth muscle cells, epithelial cells, and neurons. Monocytes and macrophages may be classified as pro-inflammatory (classically-activated, or M1 cells that can be differentiated by IFN-γ) and anti-inflammatory (alternatively-activated, or M2 cells that are stimulated by IL-4). M1 cells secrete high levels of PICs (TNFα, IL-10, IL-6 and IL-12), while M2 cells secrete AICs (IL-10 and TGF-β). Under normal conditions the balanced inflammatory response and feedback loop between AICs and PICs resolves the infection, restores organ function and maintains immune homeostasis.

Under abnormal conditions, imbalance in the feedback loop may lead to deleterious effects. The initial local tissue response, appropriate to infection, becomes amplified primarily by the innate immune system. Both pro- and anti-inflammatory cytokines are activated and a hyperinflammatory reaction, or a cytokine storm, of pro-inflammatory cytokines and activated leukocytes can exacerbate tissue damage and lead to non-resolving inflammation and patient death. Imbalance in the production and release of (excessive) pro-inflammatory and (reduced) anti-inflammatory cytokines can gradually escalate from inflammation into sepsis, septic shock, and organ failure. In addition, the host immune response may become abnormal and damage tissue and organs. With time, the persistent failure of the innate immunity (natural immune system) and adaptive immunity (defined as the acquired antigen-specific immune response developed and memorized over time) may further lead to multiple organ failure and ultimately patient death. In other words, patients could die from the body's dysfunctional immune response to infection rather than from the infection itself. Sepsis has been shown to involve early activation of pro- and anti-inflammatory responses along with major changes in non-immunological pathways such as cardiovascular, neuronal, autonomic, hormonal, bioenergetic, metabolic and coagulation pathways. Some infections may cause organ failure without the influence of a dysfunctional host response.

New definitions, published recently in JAMA, define sepsis as a medical condition with evidence of infection and life-threatening organ dysfunction. Septic shock is considered a more severe form of sepsis in which the underlying circulatory and cellular metabolic abnormalities are greater or in a state of acute circulatory failure. Patients in septic shock are hypotensive, despite the use of adequate fluid therapy, hyperlactatemic (serum lactate levels >2 millimolar per liter or >18 milligrams per deciliter) and need vasopressor therapy to maintain a mean blood pressure of 65 mm of Hg or above. Changes in brain function (mental status), lung function ($PaO_2/FiO_2 \leq 280$, without other pulmonary or cardiovascular disease as the cause) and kidney function (oliguria or urinary output <0.5 mL/kg for at least 2 hours) are also indicators of organ dysfunction and septic shock.

Systemic inflammatory response syndrome (SIRS) is another life-threatening inflammatory medical condition that is prevalent among hospitalized patients with or without an infection. Tachycardia (heart rate >90 beats/minute), tachypnea (respiratory rate >20/minute or $PaCO_2$<32 mm Hg in a spontaneously breathing patient), hyperthermia (temperature >38° C.), hypothermia (temperature <36° C.) and abnormalities in white blood cell count (>12000/mm$^3$ or <4000/mm$^3$) are common features of SIRS. Like sepsis, SIRS may follow a variety of clinical insults, including infection, pancreatitis, ischemia, multiple trauma, tissue injury, hemorrhagic shock, or immune-mediated organ injury. SIRS is considered a medical condition with an adaptive host response.

Acute respiratory distress syndrome (ARDS) or lung shock is another life-threatening medical condition that is characterized by widespread inflammation in the lungs triggered by pathologies like trauma and pneumonia. Symptoms may include shortness of breath, fast breathing, and a low oxygen level in the blood. ARDS often occurs with the failure of other organ systems such as the liver or kidneys.

Gastric and colorectal cancer, among other cancers may also be targeted with splenic neuromodulation system that blocks the pro-carcinogenic inflammation in the spleen. By blocking release of splenic TFF2, an anti-inflammatory peptide from T-cells, the expansion of myeloid-derived suppressor cells (MDSCs) can be suppressed.

Stroke, ischemic and hemorrhagic, may both be potentially treated with a drug delivery system targeted at the spleen. Preclinical testing suggests that in stroke, the activation of the spleen has a detrimental effect on stroke-induced neurodegeneration. A drug delivery system that can temporarily block the activation of the CAP through blocking sympathetic nerve firing or release of norepinephrine, would be desirable. Local drug delivery with (alpha1, beta, pan) adrenergic receptor blockers such as carvedilol, prazosin, or propranolol, may be desirable.

Several other medical conditions may be caused by uncontrolled inflammation, imbalance in cytokines released and resultant cell death. These conditions include diseases related to the gastrointestinal tract (appendicitis, peptic, gastric and duodenal ulcers, peritonitis, pancreatitis, ulcerative colitis, pseudomembranous, acute and ischemic colitis, diverticulitis, epiglottitis, achalasia, cholangitis, coeliac disease, cholecystitis, hepatitis, Crohn's disease, enteritis, and Whipple's disease); related to systemic or local inflammation (asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases related to the urogenital system (septic abortion, epididymitis, vaginitis, prostatitis and urethritis); related to the respiratory system (bronchitis, emphysema, rhinitis, cystic fibrosis, adult respiratory distress syndrome, pneumonitis, pneumoultramicroscopic silicovolcanoconiosis, alveolitis, bronchiolitis, pharyngitis, pleurisy, and sinusitis); hemorrhagic shock, infectious diseases from viruses (influenza, respiratory syncytial virus, HIV, hepatitis B virus, hepatitis C virus and herpes), bacteria (disseminated bacteremia, Dengue fever), fungi (candidiasis), and protozoal and multicellular parasites (malaria, filariasis, amebiasis, and hydatid cysts); dermatological and skin diseases (e.g., dermatitis, dermatomyositis, sunburn, urticaria, warts, and wheals); cardiovascular diseases (like vasculitis, angiitis, endocarditis, arteritis, atherosclerosis, thrombophlebitis, pericarditis, myocarditis, myocardial ischemia, congestive heart failure, periarteritis nodosa, and rheumatic fever): diseases related to the nervous system (Alzheimer's disease, meningitis, encephalitis, multiple sclerosis, cerebral infarction, cerebral embolism, Guillain-Barre syndrome, neuritis, neuralgia, spinal cord injury, paralysis, and uveitis); diseases of the bones, joints, muscles and connective tissues (various arthritides and arthralgias, osteomyelitis, fasciitis, Paget's disease, gout, periodontal disease, rheumatoid arthritis, and synovitis); other autoimmune and inflammatory disorders (such as myasthenia gravis, thyroiditis, systemic lupus erythematosus (including in patients with functional asplenia), Goodpasture's syndrome, Behcets's syndrome, allograft rejection, graft-versus-host disease, Type I diabetes, ankylosing spondylitis, Berger's disease, Type II diabetes, ankylosing spondylitis, Reiter's syndrome); as well as various cancers, tumors and proliferative disorders (e.g., Hodgkin's disease).

In other embodiments, the patients suffering from other conditions mediated by inflammatory cytokines may be treated using methods described above. These include inflammation of the gut and gastrointestinal tract, such as, appendicitis, peptic, gastric or duodenal ulcers, peritonitis, pancreatitis, ulcerative colitis, pseudomembranous colitis, acute or ischemic colitis, diverticulitis, epiglottitis, achalasia, cholangitis, cholecystitis, hepatitis, Crohn's disease, enteritis, Whipple's disease; systemic and local inflammatory diseases like asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts; dermatological diseases and conditions of the skin such as, for example, burns, dermatitis, dermatomyositis, sunburn, urticaria, warts, wheals; conditions involving the cardiovascular or cerebrovascular systems and related tissues like, vasculitis, angiitis, endocarditis, arteritis, atherosclerosis, cerebrovascular accident, sleep apnea, hypertension, thrombophlebitis, pericarditis, myocarditis, myocardial ischemia, periarteritis nodosa, rheumatic fever, coeliac disease, congestive heart failure, adult/acute respiratory distress syndrome; inflammatory conditions involving the central and peripheral nervous system like Alzheimer's disease, meningitis, encephalitis, multiple sclerosis, cerebral infarction, cerebral embolism, Guillain-Barre syndrome, neuritis, neuralgia, spinal cord injury, paralysis and uveitis; diseases of the bones, joints, and muscles and connective tissues such as various forms of arthritis and arthralgia, osteomyelitis, fasciitis, Paget's disease, gout, periodontal disease, rheumatoid arthritis, synovitis; other autoimmune and inflammatory disorders like, myasthenia gravis, thyroiditis, systemic lupus erythematosus, Goodpasture's syndrome, Behcets's syndrome, allograft rejection, graft-versus-host disease, Type I diabetes, ankylosing spondylitis, Berger's disease, Type II diabetes and Reiter's syndrome; as well as various cancers (of the breast, esophagus, prostrate, colon endometrial or kidney), tumors and proliferative disorders such as Hodgkin's disease; and other abnormal host responses to any of the primary diseases like polycystic ovary syndrome, metabolic syndrome, osteoarthritis, Pickwickian syndrome and obesity-related insulin resistance. Other conditions and diseases that may benefit from the therapy are described in U.S. Pat. Pub. Nos. 2005/0075702 A1 to Shafer, 2006/0287678 A1 to Shafer, 2009/0247934 A1 to Tracey et al., and U.S. Pat. No. 6,610,713 B2 to Tracey, U.S. Pat. No. 7,273,872 B2 to Tracey et al., and U.S. Pat. No. 7,769,442 B2 to Shafer, each of which are hereby incorporated by reference in their entireties.

Molecular Pathways and Mechanisms

Exact molecular pathways and mechanisms for sepsis, ARDS, SIRS and other inflammatory medical conditions are not well understood. Not to be limited by theory, FIG. 1 illustrates some of the complex pathways by which the inflammatory response to injury or infection occurs inside the body. Under normal conditions, the pathways are effective in controlling infection, injury, trauma etc., regulating immune response and restoring immune homeostasis without affecting organ function. Under abnormal conditions, they may be ineffective in controlling inflammation and lead to sepsis, inflammatory syndromes like SIRS and ARDS, septic shock, organ failure and death. At a cellular level, the insult from infection or trauma triggers danger-associated molecular patterns (DAMPs) and pathogen-associated molecular patterns (PAMPs), which activate innate immune cells to produce a wide range of pro- and anti-inflammatory cytokines. PAMPs and/or DAMPs sense pathogen activity by pattern recognition mechanisms (such as pattern recognition receptors or PRRs) on cell surfaces, within the cytosol and in the nucleus. Different types of cells, tissues, organs, proteins, and other molecules can act as sensors and effectors including complex protein systems (complement and coagulation systems), vascular and tissue cells (endothelial cells, epithelial cells and adipose tissue), and blood and lymphatic cells (granulocytes, macrophages, monocytes, T-cells and B-cells).

The effector cells mediate immune response by releasing different pro- or anti-inflammatory biomarkers like complement components 5a and 3a (C5a and C3a); C5a receptor protein (C5aR); terminal complement complex (C5b-9); activated partial thromboplastin time (aPTT); prothrombin time (PT); antithrombin (AT); high-mobility-group protein B1 (HMGB1); endothelial leukocyte adhesion molecule 1 (ECAM-1); intercellular adhesion molecule 1 (ICAM-1); C-reactive protein (CRP); liposaccharide-binding protein (LBP); procalcitonin (PCT); IL-6, IL-8, IL-10; macrophage migration inhibitory factor (MIF); soluble tumor necrosis factor (sTNF); soluble urokinase type plasminogen activator receptor (suPAR); soluble triggering receptor expressed on myeloid cells 1 (sTREM-1); monocytic human leukocyte antigen DR (mHLA-DR); CD64 and CD48 integral membrane glycoproteins; disseminated intravascular coagulation (DIC), to influence organ function and regulate the host immune response. These mediators may be effective in clearing the infection and restoring organ function under normal conditions of immune homeostasis. However, the uncontrolled production of PICs like TNF, IL-1a, IL-1b, IL-6, IL-8, IFN-γ, PAF, MIF and HMG-1 or HMGB1 can cause sepsis. Glucocorticoids and IL-10 anti-inflammatory mediators can suppress inflammation. The ineffective regulation between the biomarker and cytokine release may lead to continued deterioration in organ function, multiple organ failure and patient death.

Cytokine functional response depends on a number of factors. They can act as pro- and anti-inflammatory depending on the amount of cytokine, the nature of the target cell, the nature of the activating signal, the nature of cytokine produced, the timing, the sequence of cytokine action and the experimental animal model used to study inflammation and sepsis. For example, a high concentration of TGF-b suppresses cell proliferation and produces excessive amounts of extracellular matrix (fibrosis); low concentrations of TGF-b may cause excessive cell proliferation and result in impaired wound healing. As noted above, there are two types of monocyte/macrophage cells and they can be activated by different signals. Pro-inflammatory M1 monocytes can be differentially induced by IFN-γ and anti-inflammatory M2 monocytes are stimulated by IL-4. As a result, M1 cells secrete high levels of the TNFα, IL-β, IL-6 and IL-12 PICs while M2 cells secrete IL-10 and TGF-β AICs. M1 cells are known to be associated with inflammatory or autoimmune disorders; M2 cells are known to restore immune homeostasis and organ function. Timing and sequence of cytokines released can affect inflammatory response. When IL-4 and IL-13 are administered simultaneously to activated monocytes, they inhibited the production of IL-6, IL-12, MCP-1 and TNF; IL-6 and TNF levels were found to be enhanced, when they were delivered before activating signals. Similarly, the simultaneous delivery of TNF and IFN-γ at the same time was found to have no effect on production of nitric oxide (NO) by macrophages; but IFN-γ can prime the cells and produce significant amount of NO when exposed to TNF later. The local administration of drug formulations described in this invention, the timing and their sequence of delivery can regulate the pro- and anti-inflammatory cytokine levels to treat inflammatory disorders like sepsis and restore organ function.

Innate immunity refers to nonspecific defense mechanisms that come into play immediately or within hours of an antigen's entry and detection in the body. These mechanisms include physical barriers such as skin, chemicals in the blood, and immune system cells that attack foreign cells in the body. The innate immune response is activated by chemical properties of the antigen. Adaptive immunity refers to antigen-specific immune response and is more complex than the innate immunity. The antigen first must be processed and recognized. Once an antigen has been recognized, the adaptive immune system creates an army of immune cells specifically designed to attack that antigen. Adaptive immunity also includes "memory" effects that make the future host response against a specific antigen more efficient. Under normal conditions, the antigen-specific immune response fights the infection and cytokines return to their homeostasis levels.

Two mechanisms have been proposed to explain the host response to injury, inflammation and sepsis. One mechanism suggests that both PICs and AICs are activated after injury and infection and early deaths from sepsis are caused by the hyperinflammatory reaction or a cytokine storm. The second proposal suggests that activation of cytokines/innate immunity and suppression of the adaptive immunity occurs after the onset of sepsis, leading to uncontrolled inflammation, tissue injury and organ damage. Late deaths from sepsis are believed to be from failure of the adaptive immune system to regulate uncontrolled infection and death.

Recent work has demonstrated that immunity and the impaired host response are coordinated by interactions between the nervous and immune systems. There is direct evidence that the immune system is functionally and anatomically connected to the nervous system. Neural circuits of the autonomic nervous system (ANS) and the central nervous system (CNS) operate reflexively by sensing injury and infection and activate immune pathways to combat inflammation through various biomarkers, cytokines, catecholamines and neurotransmitters. The ANS is composed of afferent (sensory) nerves and efferent (motor) nerves which control body movement, organ function, heart rate, etc. to maintain normal homeostasis. The ANS also controls the inflammatory response through the inflammatory reflex circuit in which afferent signals sense injury and infection in different parts inside the body and efferent signals from the brain (CNS) regulate cytokine release to reduce inflammation. Immune cells express different neurotransmitter receptors which are modulated based on their activation status. Failure of the inflammatory reflex or pathway disrupts immune homeostasis in afferent and efferent signaling in both the immune and nervous systems and contributes to non-resolving inflammation and sepsis. In particular, preclinical studies have shown that the immune cells and the immune response are controlled by the cholinergic anti-inflammatory pathway (CAP) or reflex, mainly acting through autonomic innervation of the spleen.

Inflammation inside the body may be mediated by humoral, cellular and neural mechanisms. FIG. 1 describes some of the humoral and cellular mechanisms of inflammation. Corticosteroids, glucocorticoids, macrophage-derived tissue growth factor (TGF-b), IL-10, soluble cytokine receptors, eicosanoids and oxygenated and nitrated lipids are some examples of anti-inflammatory mediators that target the humoral component of inflammation. TGF-b and IL-4 (that stimulate macrophages to assume anti-inflammatory phenotypes), regulatory T-cells and myeloid-derived suppressor cells are examples of mediators of the cellular mechanisms of inflammation. The central nervous system receives information from the immune system from sensory neurons in response to changes in cytokine levels, pH, oxygen content and other molecular/chemical changes. Afferent neurons express receptors for TNF, IL-1, LPS and other products of inflammation.

Figure 2A:
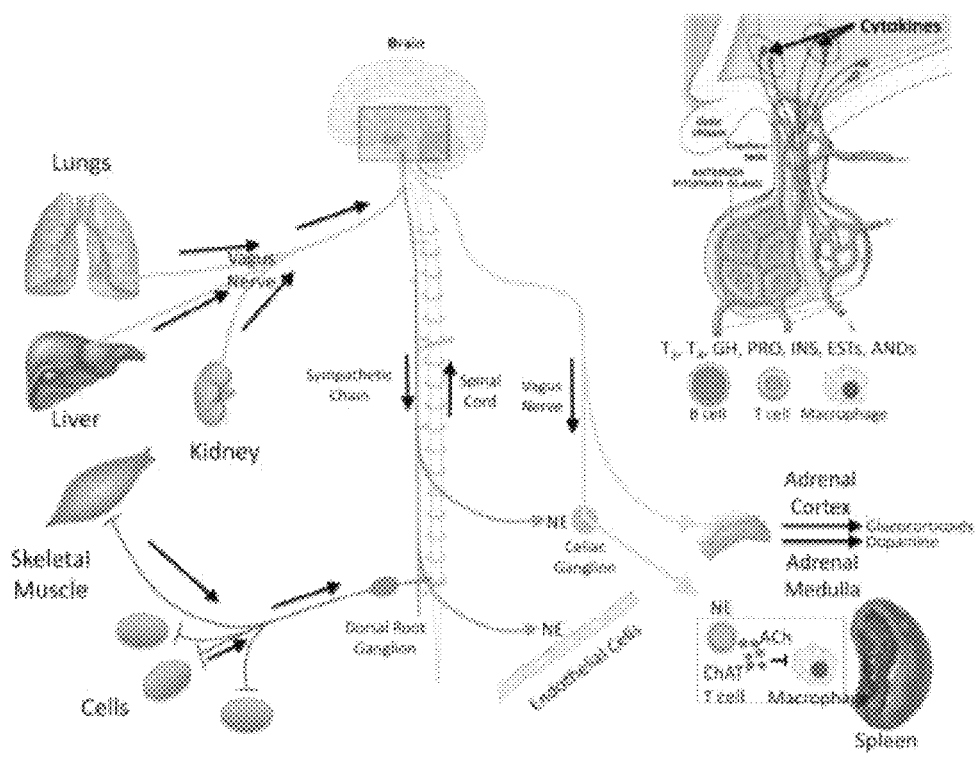
FIGS. 2A-2B shows the various afferent (sensory) and efferent (motor) neuronal pathways that maintain organ homeostasis inside the human body mediated by the vagus nerve and the sympathetic chain.
Figure 2B:
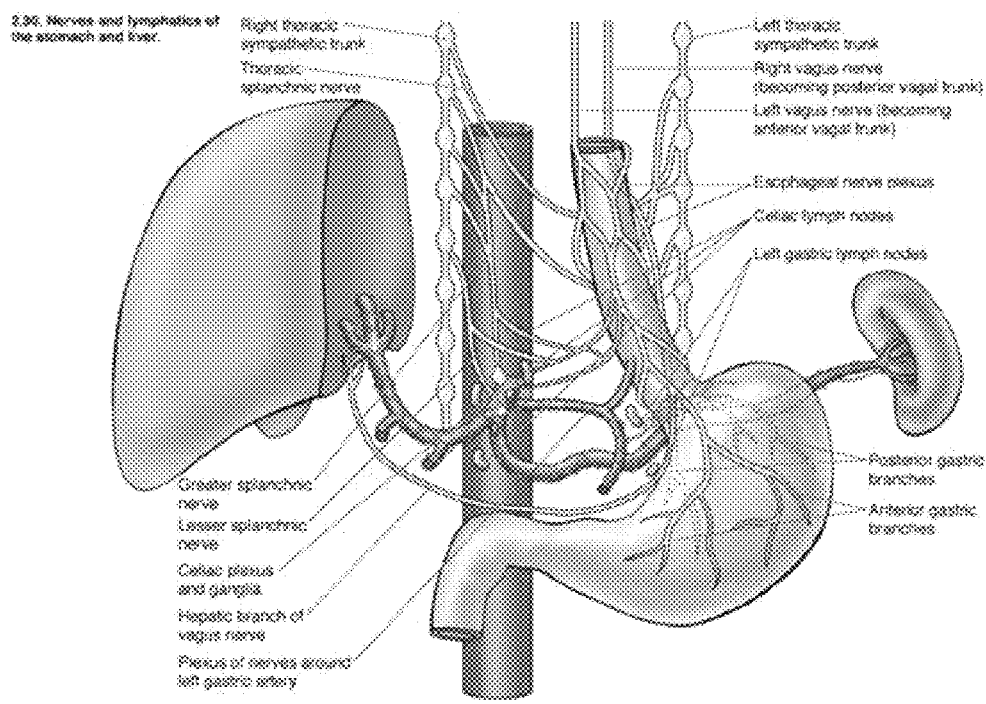
Figure 3:
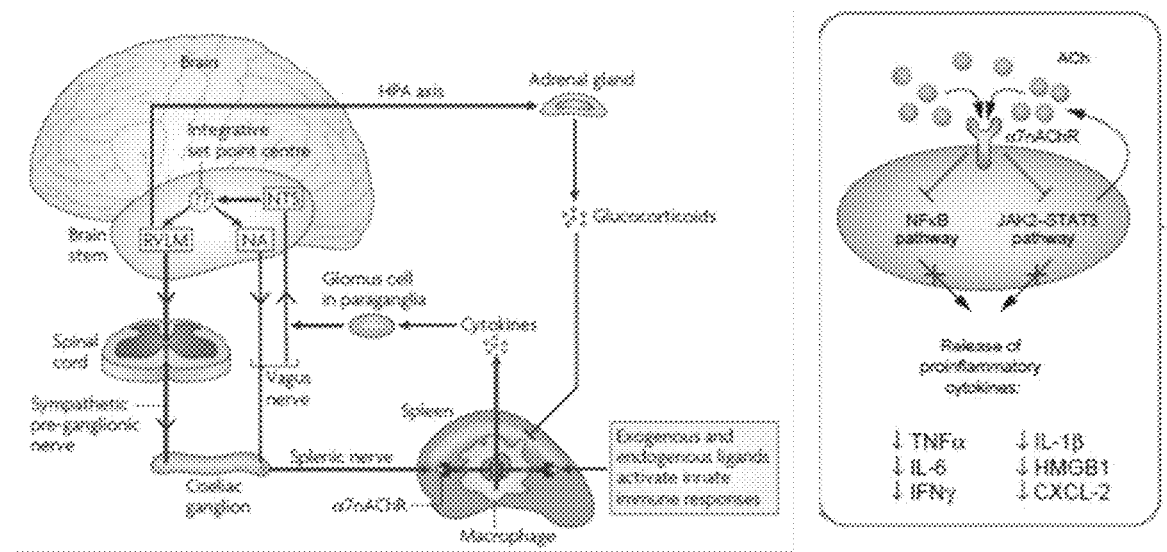
FIG. 3 shows the immune control through the cholinergic anti-inflammatory pathway (CAP) in the spleen and the underlying cellular mechanisms.

FIGS. 2 and 3 illustrate the neuronal and neuroendocrinal pathways that maintain immune homeostasis inside the body. The inflammatory reflex can include afferent and efferent signals transmitted through the vagus nerve in response to the molecular products (or biomarkers) of infection and injury, including cytokines, eicosanoids, DAMPs, and PAMPs. Since acetylcholine is the primary neurotransmitter of the vagus nerve, this mechanism of immunosuppression is also referred to as the cholinergic anti-inflammatory pathway (CAP) to mediate the neural control of systemic inflammation. The signals from biomarkers of inflammation (or cytokines) in the organs activate afferent signals in the vagus nerve to the nucleus tractus solitaries (NTS) of the brain stem, which are modulated in the dorsal root ganglia and transmitted to the brain via the spinal cord (to nuclei located in the hypothalamus and brain stem). As shown in FIGS. 2A-2B, afferent vagal signals can be activated from different organs including the lung, liver, spleen, pituitary gland and endothelial cells of other organs (intestine, stomach and colon). Efferent signals from the nucleus ambiguus (NA) and dorsal motor nucleus (DMV) return through the vagus nerve and the preganglionic efferent nerves through the rostral ventrolateral medullary (RVLM) which originate in the sympathetic trunk. Vagal afferent signals terminate in the celiac ganglion and interact with the adrenergic nerve cell bodies that project distally via the splenic nerve. Sympathetic pre-ganglionic nerves also connect at the celiac superior mesenteric plexus ganglion and innervate the spleen, liver, stomach, pancreas, adrenal glands and intestines.

As shown in FIGS. 2A-2B and 3, the splenic nerve endings release norepinephrine (NE) in the spleen, which in turn stimulates T-cells (expressing choline acetyltransferase, ChAT) and enhances acetylcholine (ACh) production. ACh interacts with a7nACh receptors (a7nAChRs) on macrophages, prevents activation of the NF-kB (nuclear factor, kappa-light-chain-enhancer of activated B cells) pathway and suppresses the release of pro-inflammatory cytokines. ACh may also inhibit the activation of the JAK (janus-kinase)-STAT3 (signal transducer and activator of transcription) signaling pathway for transmitting extracellular chemical signals and limit or reduce the release of pro-inflammatory cytokines TNF-a, IL-1b, IL-6, HMGB1, IFN-γ and CXCL-2 (cytokine belonging to the CXC family, also called macrophage inflammatory protein 2-alpha, or MIP2-alpha). Neuromodulation or activation of the sympathetic chain can enhance the release of NE in target tissues. NE stimulation of alpha-adrenergic receptors enhances cytokine release. NE stimulation of beta-adrenergic receptors suppresses cytokine release and treats inflammation and sepsis. Local administration of drug formulations described in this invention near various target organ nerve sites can affect neuronal signaling and regulate PIC and AIC levels to treat sepsis and other inflammatory disorders. Preclinical studies have shown that stimulating the vagus nerve suppresses innate immune responses and downregulates PIC release in the spleen through the α7nAChR mechanism.

Activation of the inflammatory reflex by sensory input to the brain or CNS can also trigger efferent signals to other organs or affect the cytokine levels through neuro-humoral pathways. As shown in FIG. 3, the signals are transmitted to the adrenal gland through hypothalamic-pituitary-adrenal (HPA) axis can increase the release of glucocorticoid hormones and provide another method for neuronal control of the humoral anti-inflammatory pathway to regulate the immune response and restore immune homeostasis.

Under normal conditions, the vagus nerve inhibits activity of the innate immune response to pathogen associated molecular products. The inhibitory activity of the inflammatory reflex can be enhanced by increasing adrenergic signals in the splenic nerve by electrical stimulation of the vagus or splenic nerves or by pharmacologically activating adrenergic splenic neurons using cholinergic agonists. The inflammatory reflex can also be inhibited by increasing splenic adrenergic activity by altering signals from the preganglionic neurons arising on the sympathetic chain, or by altering signals arriving from the vagus nerve that terminate on interneurons residing in the celiac ganglion that can modulate the signals arising from the sympathetic chain. In addition, adrenergic neurons in the spleen may be modified by the onset of inflammation leading to an impaired inflammatory reflex and resulting in abnormal (increased) inflammation and cytokine levels.

Experimental studies have demonstrated that stimulation of the vagus nerve may attenuate cytokine release in sepsis, renal ischemia reperfusion injury (IRI), and other states of inflammation. Electrical stimulation of the splenic tissue, both ex vivo and in vivo, through the (cholinergic) vagus nerve reduced cytokine production when challenged with inflammatory stimuli. Administration of cholinergic agonists and surgical methods to stimulate the vagus nerve may also be promising pathways to treat sepsis. Drug formulations and methods of administration to alter these signaling pathways and optimize the expression of cytokines for resolving inflammation and treat sepsis and related medical conditions are described.

Preclinical work in mice showed that ultrasound energy can protect mice from IRI and prevent acute tissue injury and resulting fibrosis through the splenic CAP and preserve kidney morphology and function. Splenectomy and other studies revealed that CD4+ T cells in the spleen may mediate the protective effects; blockade or genetic deficiency of the a7nAChR nullified the protective effect and an a7nAChR agonist promoted the therapeutic effect. Although ultrasound energy-based treatment has been proposed for the prevention of AKI, by stimulating the splenic CAP, its clinical benefit on sepsis-associated AKI has not been established.

Nicotinic acetylcholine receptors (nAChRs) are also involved in mechanisms of immune regulation. nAChR ligands such as nicotine may protect mice against various inflammatory diseases like rheumatoid arthritis and sepsis. In preclinical models, nicotine acts on monocytes (macrophages) and inhibit the release of PICs (TNFα, IL-1β, IL-6 and IL-12) and the concomitant upregulation and secretion of AICs (IL-10, TGF-β). α7 and α9 subunits of nAChRs may be involved in the production of bone marrow M1 monocytes.

Other neuro and/or immune pathways and organs may also affect inflammation and cytokine release. Vagal nerve signals may modulate the release of dopamine from the adrenal medulla. The stimulation of D1 receptors on monocytes and macrophages may limit cytokine expression and/or cytokine release. Inflammatory afferent signals to the brain from endocrine system may enable cytokine transfer across the attenuated blood-brain barrier of the hypothalamic-pituitary junction, and trigger cytokine production by cells in the central nervous system (CNS).

Melanocyte-stimulating hormone (MSH), thyroid stimulating hormone (TSH), glucocorticoids, leptin, ghrelin, and adrenocorticotropin (ACTH) are some of the factors that modulate cytokine production in the CNS. In addition, the hypothalamic response to cytokines may alter the release of ACTH, TSH, prolactin (PRO), growth hormone (GH), and follicle stimulating hormone. Monocyte and macrophage activity and cytokine production may also be altered by thyroid hormones (T3, T4). Similarly, both T and B cells function may be decreased by estradiols (EST) and increased by androgens (AND); GH, prolactin, and insulin stimulate T cell activity. Such neuro-hormonal signaling pathways in the adrenal glands, liver, lungs kidney, hypothalamus, pituitary gland and the CNS may be affected using methods and devices described in the following sections to resolve uncontrolled inflammation and pro-inflammatory cytokine release, treat sepsis and restore organ function.

Current Treatments for Sepsis

There are no approved drugs to treat sepsis. Antibiotics, oxygen and intravenous fluids (fluid replacement therapy) are used to treat sepsis patients in the intensive care unit. Mechanical ventilation and dialysis are also used to assist lung and kidney function. Medications to control blood pressure (e.g., vasopressin, dopamine, neosynephrine, norepinephrine) may be used. The use of corticosteroids is controversial, and the use of activated drotrecogin alfa (a drug marketed for severe sepsis) has been discontinued and withdrawn from the market due to bleeding complications. Mortality rates from sepsis, severe sepsis and septic shock conditions can be as high as 30%, 50% and 80%, respectively.

Accordingly, in some embodiments, a method can involve a minimally-invasive therapy to treat sepsis using local chemo neuromodulation without the need for a permanent implant inside the body. A small volume of drug or a drug delivery system may be administered locally near the splenic nerve, which runs along the splenic artery and splenic vein, with the clinical goal of treating sepsis and providing mortality benefit. The drug may be injected near the target nerve site using percutaneous needle-based techniques under external ultrasound or CT imaging guidance, or using an endovascular catheter under x-ray fluoroscopy guidance. In one embodiment, the injectable drug may be administered one time to affect local nerve signaling, causing changes in neuronal and/or immune function through different neuronal and neuro-hormonal pathways to control and resolve inflammation and sepsis. In other embodiments, the drug may be administered over a period of time by administering a sustained/controlled release formulation of the drug or by drug infusion, over a period of a few hours, days or weeks to modulate the immune and nervous systems and treat sepsis. These methods are described in detail below.

Other Mechanisms of Sepsis and Treatment:

Other mechanisms may also be involved in the development of sepsis. It can be caused by, e.g., bacterial pneumonia or peritonitis from leaking of intestinal contents. Subsequent events include apoptotic deletion of T and B cells, defective DCs, and onset of immunosuppression, together with defective innate immunity. These events may lead to loss of the ability to clear bacteria, resulting in development of multi-organ failure (MOF) and death. Repetitive systemic administration of cardiac glycosides has been shown to down-modulate pro-inflammatory B and T cells. Other studies have shown that regular administration of cardiac glycoside can down-modulate the expression of type I interferons. We describe in some embodiments a new method to treat diseases associated with inflammatory signaling by administering a site-specific bolus of drug, locally over a period of time, directly into an innervated organ with lymphoid tissue to prevent sepsis and restore organ function.

Sepsis may also be caused from inflammation induced by defects or dysfunction of the redox balance between reactive oxygen species (ROS) and anti-oxidant enzymes inside the body. ROS buildup may lead to high levels of sustained inflammation and other immune activation states in endothelial cells and leukocytes, ultimately causing organ failure and death. Neuromodulation, by local administration of drug formulations described below near target organs and target tissue (including neurons) may affect the redox balance and restore immune function.

Examples include inducers of Nrf2, a basic leucine zipper protein that regulates expression of anti-oxidant proteins. Dietary products, such as sulforaphane, may cause of induction of Nrf2 and may be candidates for reversal of the redox imbalance in sepsis.

Cellular depletion of adenosine tri-phosphate (ATP) may cause inflammation and sepsis. Under normal conditions peroxisome proliferator activity receptors (PPARs) respond to oxidative stresses and preserve mitochondrial function to contain inflammation. Sepsis may reduce PPAR levels, lead to a reduction in the mitochondrial ATP levels and cause uncontrolled inflammation. Neuromodulation by local administration of drug formulations described below, near target organs and target tissue, may alter neuronal and/or immune signaling, affect cellular ATP levels and restore immune homeostasis. Sepsis may also be caused by defective phagocytosis from dysfunction in macrophages and dendritic cells (DCs), T-cell and B-cell death, and expression of inhibitory ligands and receptors that suppress immune response. Defective phagocytes are unable to defend pathogens like bacteria and fungi. IL-7 has anti-apoptotic effects and promotes T and B cell proliferation. Neuromodulation by local administration of drug formulations described below, near target organs and target tissue, may alter IL-7 production, control inflammation and restore immune homeostasis.

Recent studies have shown that infectious pathogens may also be involved in electrical signaling by affecting nerve conduction, inflammation and circulating cytokine levels. Specifically, bacteria are found to interact through ion channels in addition to communication through the transmission of chemical molecules. For example, bacterial communication is believed to be one of the reasons why biofilms (bacteria trapped in an extracellular matrix) are resistant to antibiotics and can act like a microorganism. Bacteria on the outer surface sense the (harmful) antibiotic and can trigger an immune response to prevent the antimicrobial agent from entering the core of the biofilm. This may be one of the reasons why sepsis patients may not respond to antibiotics and other drugs since the collective signaling from bacteria (pathogens) may alter the body's immune response. Neuromodulation, by local administration of drug formulations described below near target organs and target tissue may alter the tissue (endothelial and/or epithelial) response, nerve signaling, and cytokine levels, to control inflammation and restore immune homeostasis.

Immune Function of the Spleen and Local Chemo Neuromodulation

The spleen is an important organ for mediating inflammation inside the body. Tissue expression of proinflammatory cytokines like interleukin (IL)-1, IL-6, IL-8, tumor necrosis factor (TNF)-α, and IL-12] and elevated plasma levels are detected within hours after macrophages sense the bacteria. Large amounts of cytokines are produced in these tissues, with peak TNF-α mRNA expression occurring around 3 h after septic surgery or lipopolysaccharide (LPS, an endotoxin) injection in mice, resulting in the engulfment of bacteria by macrophages. The spleen produces nearly 10-fold more TNF-α than the liver and lung on a per-gram-of-tissue basis. Preclinical data show that a reduction in inflammatory cytokines can reduce inflammation, endotoxemia and improve survival from sepsis.

Studies have shown that TNF-producing macrophages are found in the spleen near the catecholaminergic nerve terminals suggesting the vagus nerve controls immune function and inflammation through the CAP mechanism involving two serially-connected nerves. The first is the pre-ganglionic parasympathetic (afferent) vagus nerve, which senses pathogens, ischemia, injury and cytokine levels and sends sensory signals to the brain via the NTS (FIGS. 2 and 3). Polysynaptic relays in the brain stem then connect to ANS outflow centers, the rostral ventrolateral medullary (RVLM) sympathoexcitatory neurons and the vagal motor neurons in the nucleus ambiguus (NA) and the dorsal vagal motor nucleus. The vagal efferent signals from the brain arrive at the celiac ganglion through the vagus nerve. The second nerve involved in the CAP mechanism is the post-ganglionic sympathetic (efferent) splenic nerve which originates in the celiac-superior mesenteric plexus and travels along the splenic artery. Signals from the brain through the efferent vagus and efferent splenic nerve trigger the splenic CAP mechanism, attenuate PIC levels and treat sepsis and other inflammatory disorders.

Electrical stimulation of the cervical vagus nerve has been found to attenuate systemic TNF levels in control rats subjected to sham surgery. In contrast, vagus nerve stimulation (VNS), after surgical ablation of the splenic nerve, was not effective in reducing TNF levels suggesting the role of the spleen in mediating inflammation. Studies by Tracey et al [2008] also show that the vagus nerve functionally communicates to the splenic nerve. VNS increased the pancreatic NE levels independent of muscarinic receptors. Electric stimulation of the splenic nerve enhanced NE release from the spleen and attenuated LPS-induced TNF through a beta-adrenergic-dependent mechanism, in ex-vivo models. In vitro, acetylcholine and other cholinergic agonists were shown to reduce LPS-induced TNF in human and mouse macrophages and in mouse splenocytes through the a7-nicotinic acetylcholine receptor (a7-nAchR) mechanism. The nicotinic acetylcholine receptor subunit-7 is expressed in autonomic ganglia, where it may mediate fast synaptic transmission. Acetylcholine released by the vagus nerve may act on a7-nAChR receptors expressed in the ganglia of the celiac superior mesenteric plexus and modulate splenic nerve function. This mechanism is supported by evidence that VNS activity does not suppress TNF production in a7 knock-out mice.

Figure 4A:
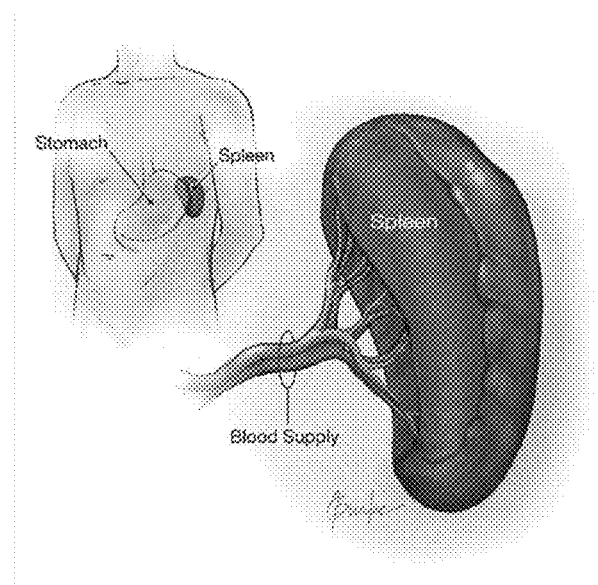
FIGS. 4A-4B shows the location of the spleen inside the body (4A) and structure of the spleen (4B) illustrating the blood vessels and nerve fibers innervating the white pulp, red pulp and the marginal zone.
Figure 4B:
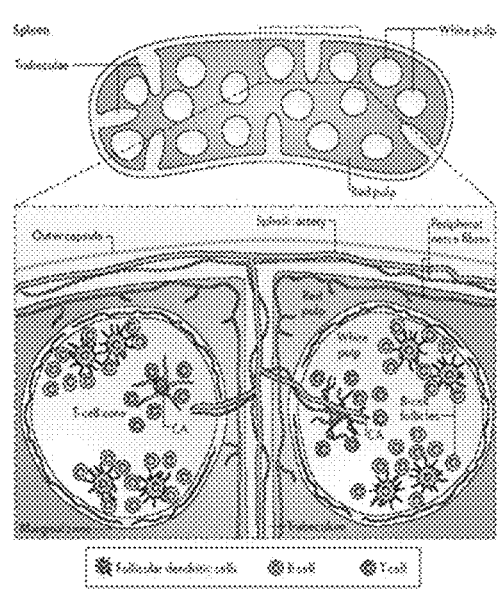
Figure 7A:
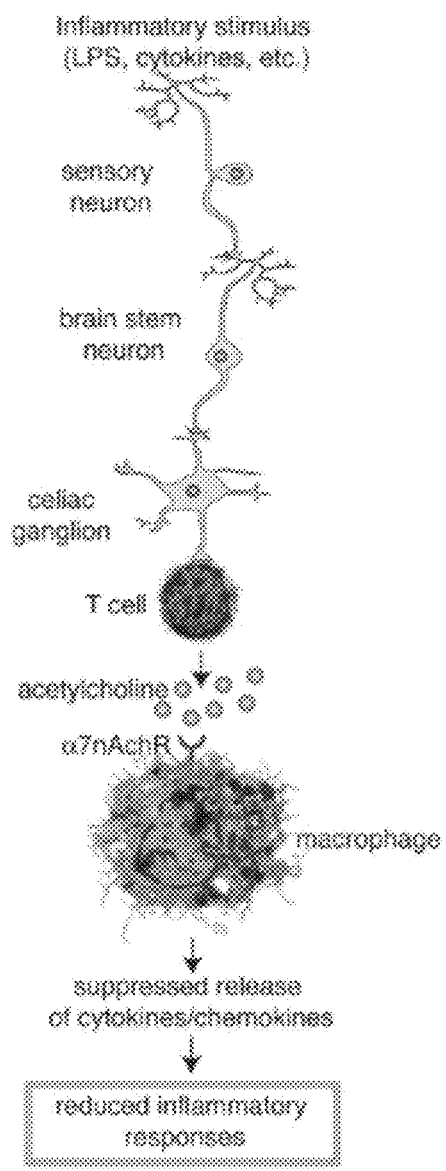
FIGS. 7A-7B show the sympathetic and parasympathetic neuronal pathways in inflammation and sepsis.

As shown in FIG. 4B, activation of the adrenergic splenic nerve results in the release of NE. NE binds to beta-adrenergic receptors in the vicinity of CD4+ T cells in the white pulp of the spleen. The binding stimulates T cells to express choline acetyltransferase (ChAT) and enhances the secretion of acetylcholine (ACh). ACh then crosses the marginal zone into the red pulp of the spleen, where it binds to a7nAChR receptors on splenic myeloid cells (or macrophages). A7nAChR signal transduction suppresses the synthesis and release of proinflammatory cytokines such as TNF-a, IL-1b, IL-18, HMGB1, and other cytokines. The suppression initially occurs in the spleen, which in turn lowers the systemic cytokine levels and limits inflammatory cytokine expression and release during sepsis and related medical conditions. This cholinergic anti-inflammatory pathway, mediated by the parasympathetic nervous system, is summarized in FIG. 7A.

Figure 7B:
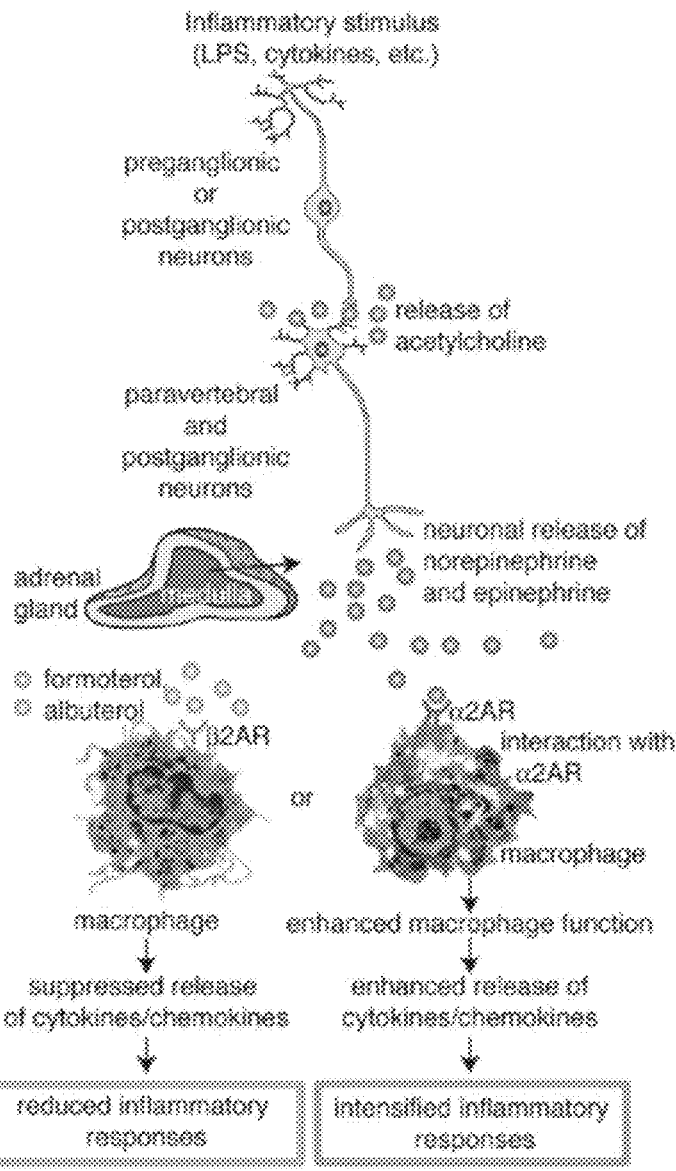

Similarly, the SNS may also influence inflammation and sepsis (FIG. 7B). Activation of the sympathetic chain leads to release of NE in target organ tissues of the spleen, lung, adrenal glands, pancreas, stomach, gut, intestines. NE stimulation can increase or suppress inflammation depending on adrenergic receptor type involved. Alpha-adrenergic receptors (α-ARs) enhance cytokine release and β-AR stimulation suppresses cytokine release. Thus activation of SNS pathway may suppress the inflammatory response in the presence of β2AR agonists (formoterol, albuterol, salmeterol) or may intensify the inflammatory response in the presence of α2AR agonists (epinephrine, norepinephrine). These mechanisms and pathways provide new nerve target sites to modulate SNS and PSNS activity through local chemo neuromodulation and influence the inflammatory response inside the body using local administration of drug formulations described below. The therapeutic agent could be a nonselective beta agonist such as isoprenaline, or a beta-1 or beta-2 selective agonist in some embodiments. The therapeutic agent could be an alpha-1 agonist or alpha-2 agonist (e.g., clonidine) in some embodiments.

In one embodiment, a drug formulation may be administered locally within the splenic tissue using delivery methods described below. Local neuromodulation of adrenergic receptors on macrophages may enhance or decrease TNF production depending on whether α or β receptors are activated. NE release may attenuate the production of TNF in the spleen through β receptors are activated. NE release may attenuate the production of catecholaminergic activation of the α7nAChR signaling in CAP to release cytokines. Since there are no cholinergic nerve fibers in the spleen, the acetylcholine may be produced by non-neuronal endothelial cells and lymphocytes like splenic T-cells, and B-cells which are richly innervated by the adrenergic axons of the splenic nerve.

In another embodiment, the drug formulation may be delivered locally near the splenic nerve to stimulate and upregulate the production of NE. The splenic nerve is an inherent component of a pathway that originates in the brain and terminates in the spleen to regulate the immune response. Electrical stimulation of the hypothalamus and central administration of angiotensin, IL-β, or IFN-α have been shown to modulate spleen immune cell function via the splenic nerve, an effect that has been ascribed solely to the sympathetic nervous system.

Additionally, NE release may activate the CAP pathway (through α7nAChR signaling and T-cell mediated macrophage activity), and suppress cytokine release.

Figure 8:
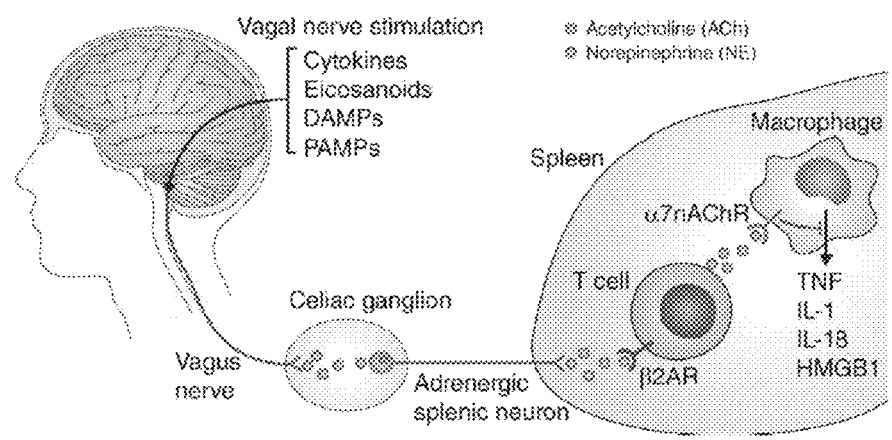
FIG. 8 illustrates the effect of vagus nerve on inflammatory pathways in the spleen.

FIG. 8 illustrates the vagus nerve and the sympathetic chain network that innervates the spleen and surrounding organs. In one embodiment, the drug formulation may be delivered locally to a portion of the vagus nerve to induce neuromodulation and suppress the release of pro-inflammatory cytokines in the spleen. Following activation of the inflammatory reflex by sensory input to the brainstem, the signals are relayed to the nuclei controlling the function of the hypothalamic-pituitary-adrenal (HPA) axis, which increases glucocorticoid hormone release by the adrenal gland. This provides another pathway and potential nerve target site for local neuromodulation, through a one-time administration of drug formulations described below, and affect the neural networks, the compensatory nerve and molecular signals to adjust immune responses, and the humoral anti-inflammatory mechanisms that may more chronically modulate innate and adaptive immune responses.

In another embodiment, the immune and cytokine activity may be controlled by modulating the sympathetic nerves originating from the sympathetic chain through the local administration of drug formulations described below. The drug acts to block nerve conduction, attenuate neurotransmitter levels and reduce cytokine levels. Specific formulations and methods to treat sepsis are described in the following sections.

Anatomy and Physiology of the Spleen

Figure 4C:
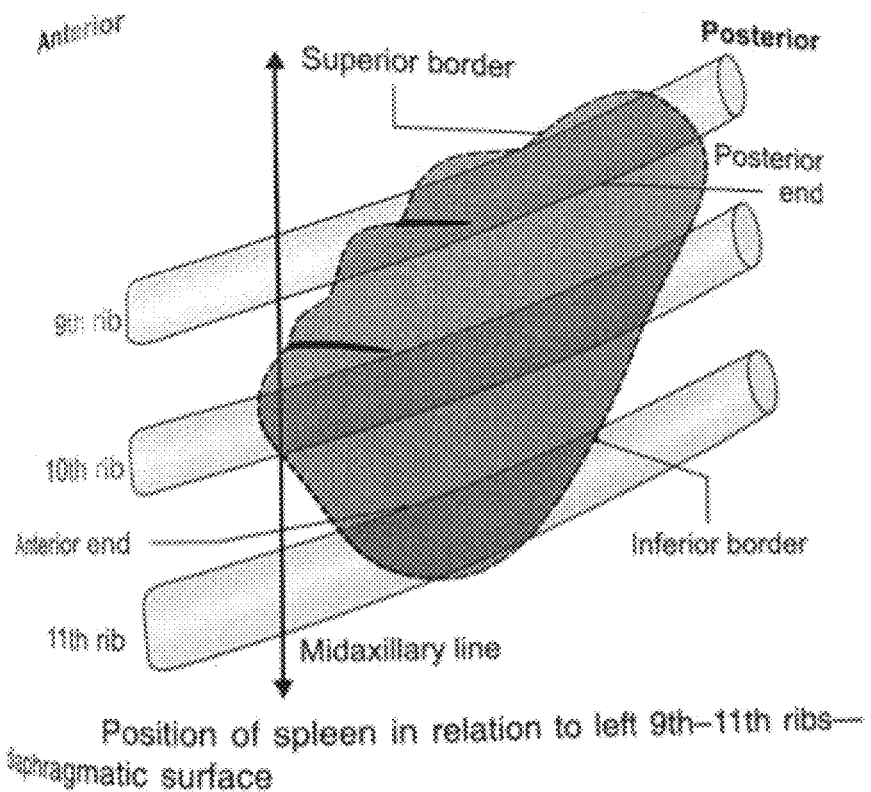
FIG. 4C illustrates the position of the spleen in relation to the left $9^{th}$ through $11^{th}$ ribs.

The spleen plays an important role in the body's immune system, and filters blood and mediates the immune system against bacterial infection and multi-organ dysfunction or failure. It is an organ of the lymphatic system and is located in the upper left quadrant of the abdomen, to the left of the stomach, as illustrated in FIG. 4A. The spleen has a diaphragmatic surface, which extends between the $9^{th}$ ribs to the $11^{th}$ ribs on the lateral aspect at the left side, as shown in FIG. 4C. The spleen also has a visceral surface. The two surfaces meet at a sharp superior margin, which carries the splenic notch. Below the notch is the angle at the same superior margin. The visceral surface includes the following four impression: the gastric impression for the stomach; the pancreatic impression for the pancreas; the colic impression for the splenic flexure; and the renal impression placed at its hilus for the left kidney.

Figure 5A:
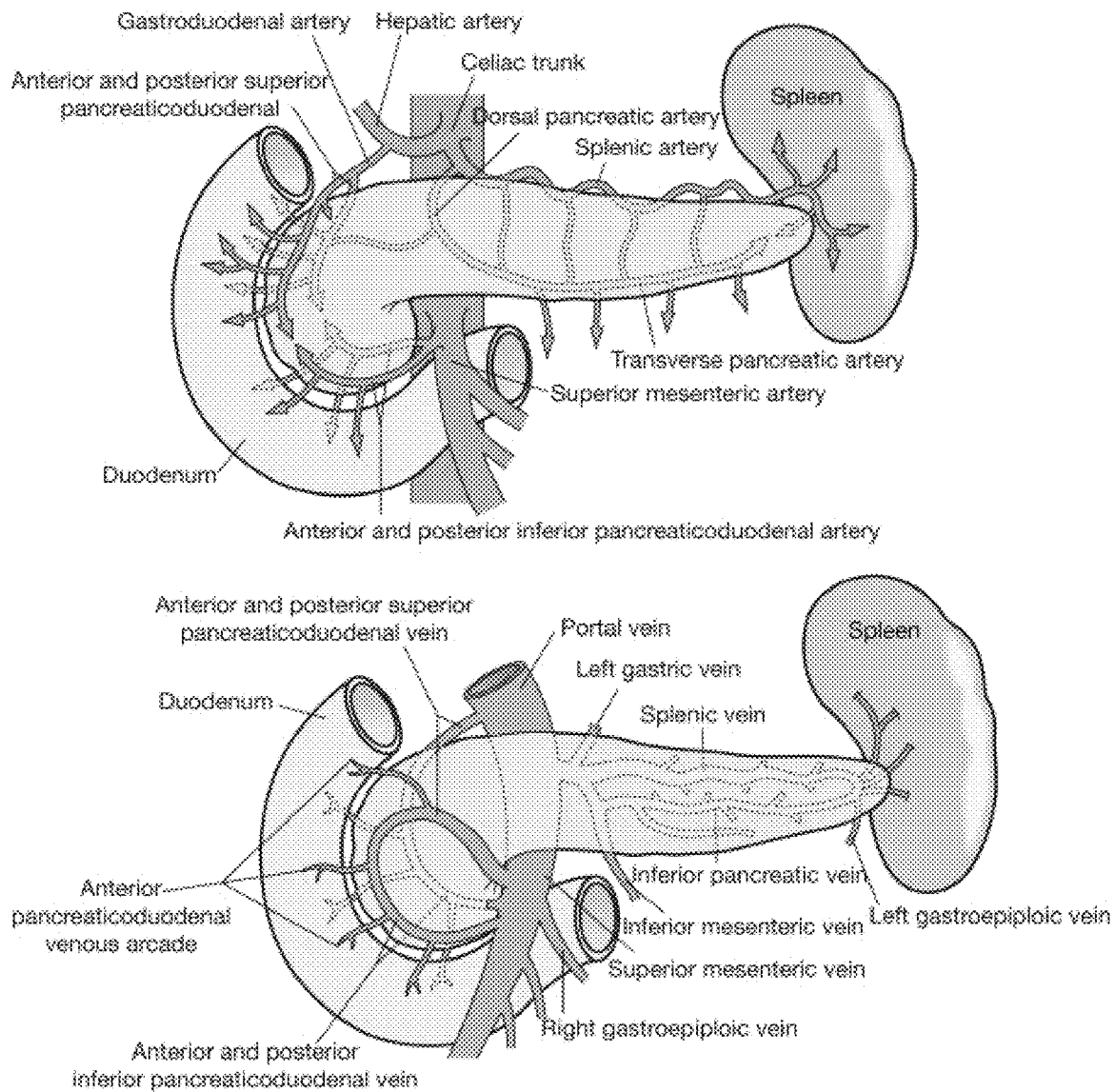
FIG. 5A shows the blood circulatory system supplying the spleen and nearby organs (stomach and pancreas).
Figure 5B:
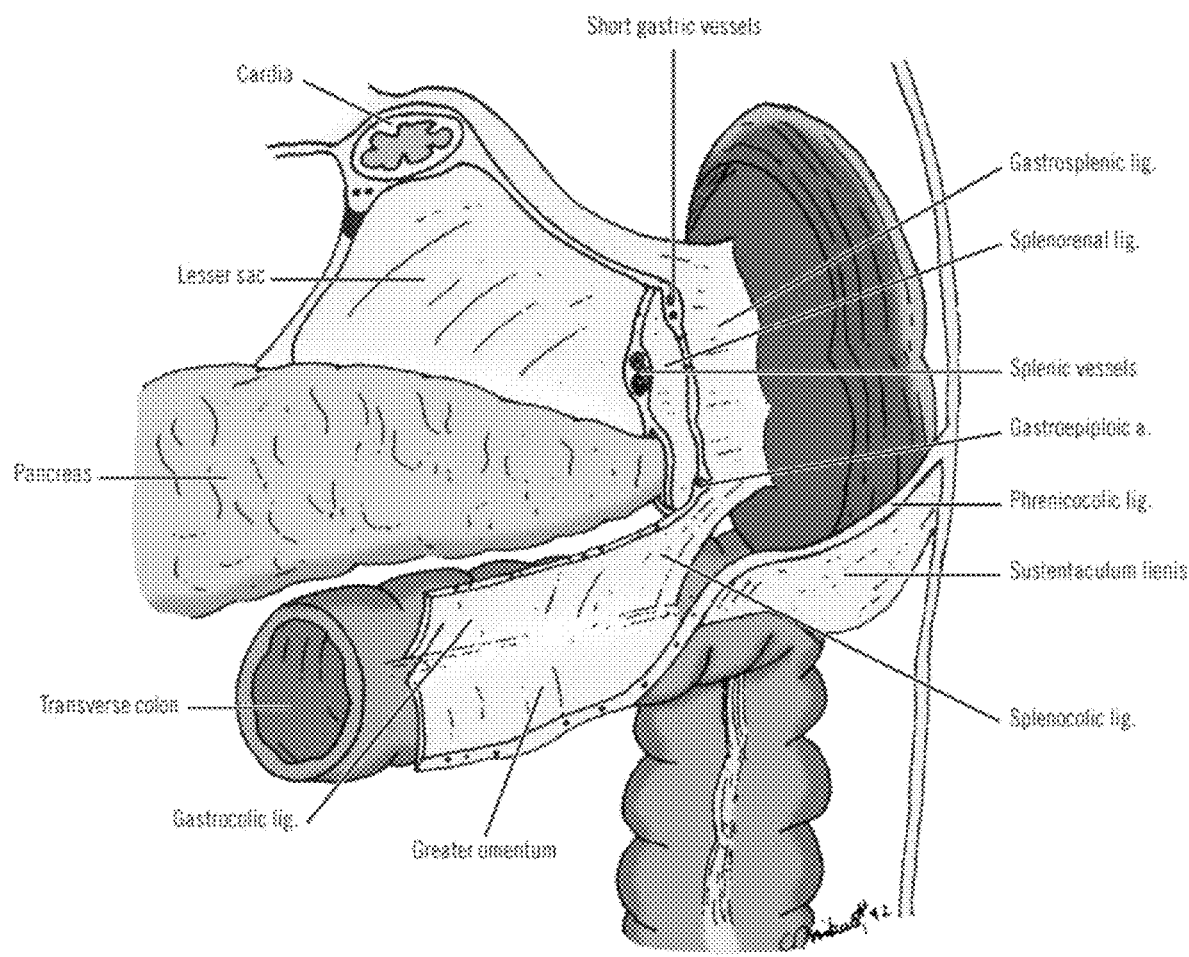
FIGS. 5B-5E illustrate various views of spleen and associated anatomy, including the splenorenal and gastrosplenic ligaments.
Figure 5C:
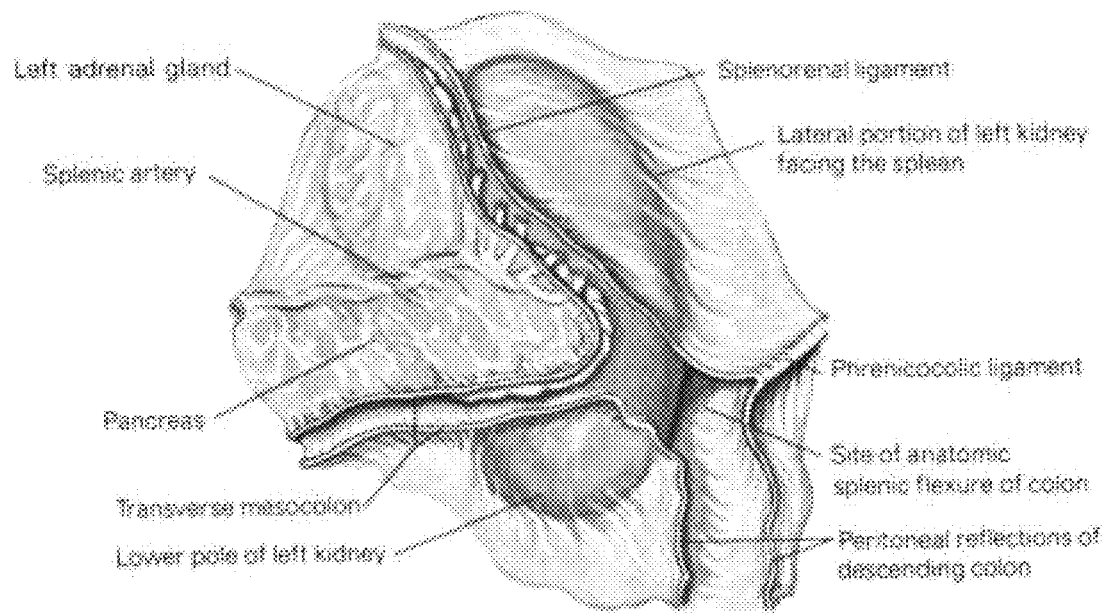
Figure 5D:
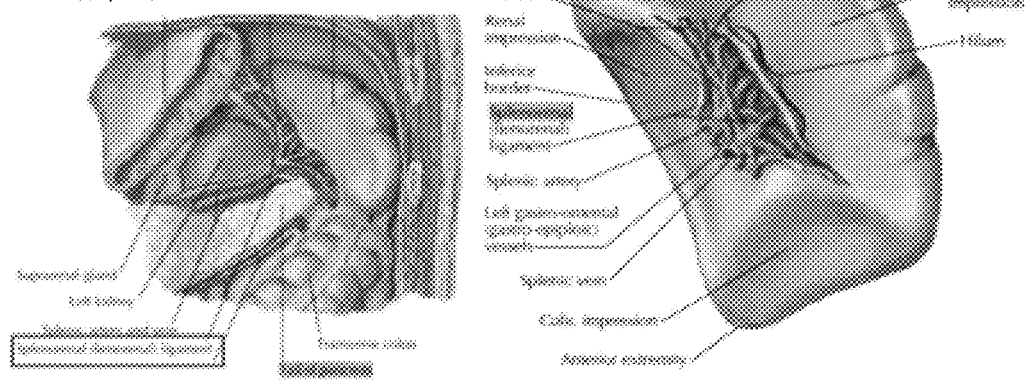
Figure 5E:
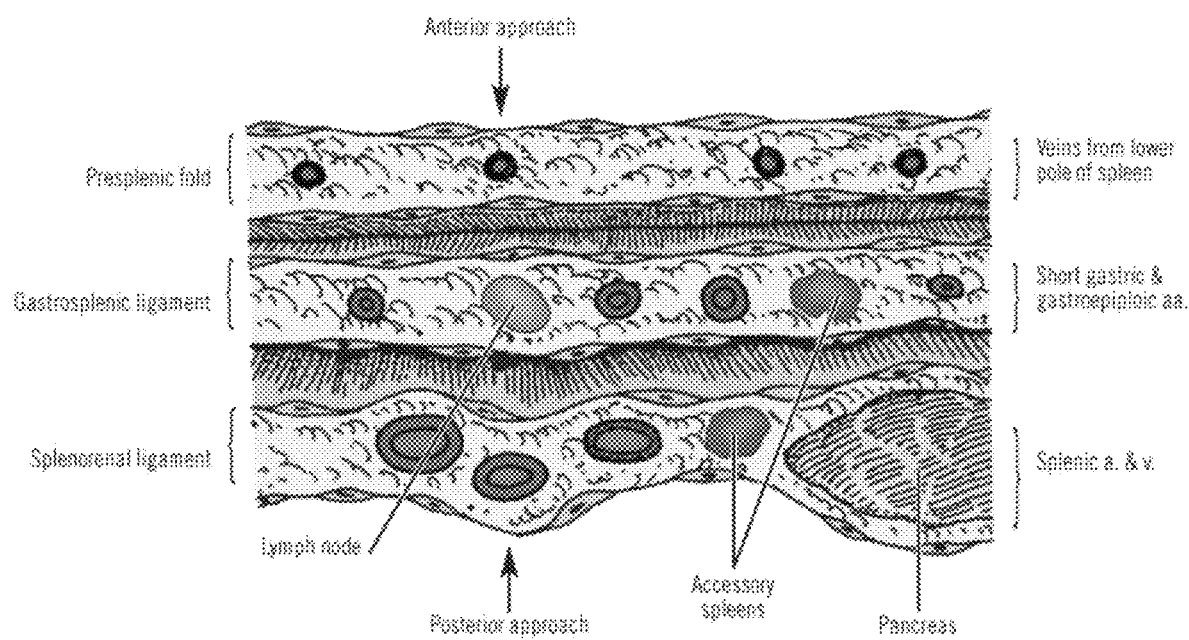
Figure 5F:
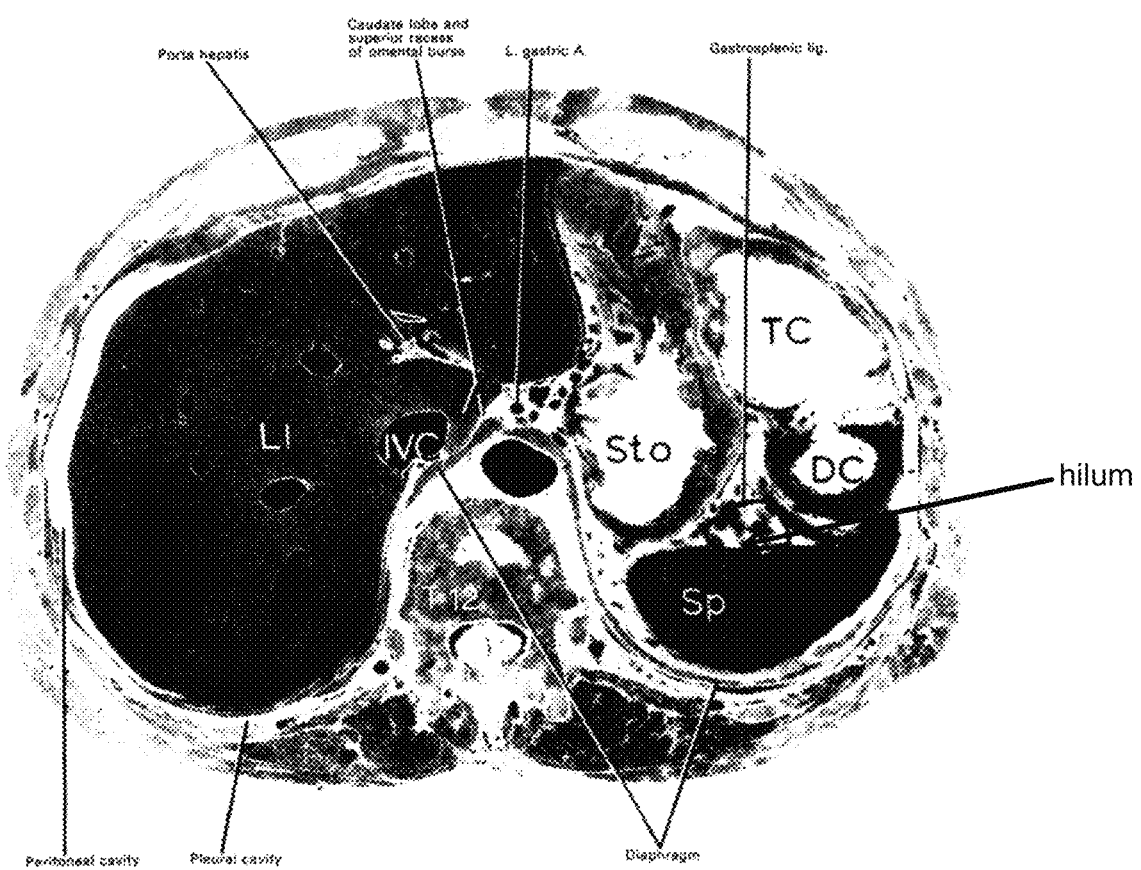
FIG. 5F illustrates an axial section at T12 illustrating the gastrosplenic ligament attachment site to the spleen at the splenic hilum.

Hilum. The hilum is located on the inferomedial part of the gastric impression and contains splenic arteries, nerves, and veins. The hilum is also the location of attachment to the gastrosplenic and splenorenal (lienorenal) ligaments. Double layered peritoneal folds (e.g., with an anterior layer and a posterior layer in some cases), variously named as ligaments, omenta and mesenteries, connect the intraperitoneal organs to the abdominal wall. Some of these ligaments contain blood vessels and lymph nodes while others are avascular. The peritoneal folds can act as conduits for the passage of blood vessels and lymphatics from the retroperitoneum to reach intraperitoneal organs, The gastrosplenic ligament is a fold of the peritoneum that extends from the hilum of the spleen to the greater curvature of the stomach and contains short gastric vessels, lymphatics, and sympathetic nerves, including the short gastric vessels and left gastro-epiploic vessels. The splenorenal/lienorenal ligament is a fold of peritoneum that extends from the hilum to the anterior surface of the left kidney and also contains the splenic vessels and splenic nerves (e.g., where the splenic artery branches into several end arteries within the splenorenal ligament). The phrenicocolic ligament is a fold of peritoneum that extends from the splenic fixture of the colon to the diaphragm along the midaxilary line. Branches of the splenic artery enter the hilum where the gastrosplenic and splenorenal ligaments attach. Some of these anatomic features are illustrated, for example, in the different anatomic views of FIGS. 5B-5D. FIG. 5E schematically illustrates a cross-section illustrating, from anterior to posterior, the presplenic fold, gastrosplenic ligament, and the splenorenal ligament. The presplenic fold can include veins from the lower pole of the spleen. The gastrosplenic ligament can include short gastric and gastroepiploic arteries between its folds. A lymph node and accessory spleen is also shown. The splenorenal ligament can include between its folds the pancreas, splenic artery, splenic vein, and an accessory spleen. FIG. 5F illustrates an axial cross-section through the body of the T12 vertebra (and proximate the $9^{th}$, $10^{th}$, and $11^{th}$ ribs) showing where the gastrosplenic ligament attaches to the spleen (Sp) which defines the hilum of the spleen.

Figure 4D:
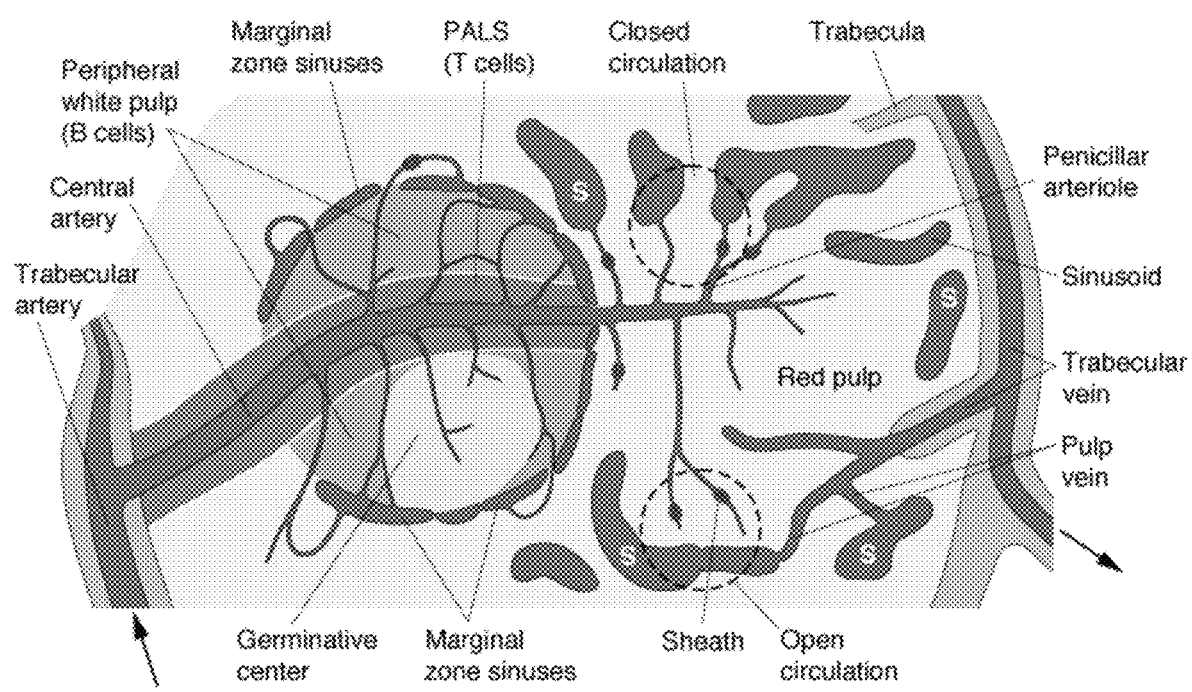
FIG. 4D also schematically illustrates a histological section of the spleen and selected features.

There are two main types of tissue in the spleen that are specialized for their functions. The spleen includes regions containing red pulp, white pulp and a marginal zone, as illustrated in FIG. 4B. The white pulp includes ovoid masses of lymph tissue called Malpighian corpuscles, or lymph follicles, within which may be seen germinal centers. Here, lymphoid aggregations including (B- and T-) lymphocytes and macrophages are arranged around arteries. The red pulp forms the greater part of the splenic substance, including the reticular meshwork and venous sinuses between which are splenic cords of cells. FIG. 4D also schematically illustrates a histological section of the spleen and selected features, including the trabecular arteries (branches of the splenic artery after it passes into the trabeculae of the spleen, where it branches), central arteries (when the trabecular arteries reach the white pulp and become covered with periarteriolar lymphoid sheaths), peripheral white pulp, marginal zone sinuses, trabecula, germinative center, penicillar arterioles (when branches of the central arteries are given to the red pulp), sinusoids, trabecular vein, and pulp vein.

Once bacteria or other infectious organisms enter the body, the reticuloendothelial system that includes phagocytic myeloid cells (macrophages) in the spleen, liver, lung and the peritoneum filter and scavenge the organisms from blood. Although the liver is the largest organ, the red pulp of the spleen is more efficient in removing debris through phagocytosis. The red pulp mechanically filters the old red blood cells and platelets, and maintains a reserve of red blood cells, platelets and monocytes. White pulp removes antibody coated bacteria and blood cells, moving through the blood and lymph node circulation, by active immune response through different humoral and cell-mediated pathways described below. Blood supply to and from the spleen primarily occurs through the splenic artery and splenic vein, respectively, as shown in FIG. 5A, which also illustrates arterial (top) and venous (bottom) anatomy relevant to the spleen, pancreas, and duodenum.

Artery. The splenic artery is the primary vessel supplying blood to the spleen and is the largest branch of the celiac trunk. The splenic artery may be tortuous in adults (10%) and the tortuosity is thought to increase with age. The artery typically ranges in diameter between 7 and 8 mm of diameter.

The splenic artery originates from the celiac trunk the majority of the time (90.6%) but also the abdominal aorta (8.1%) and other sites (1.3%). The splenic artery typically courses across the superior surface of the pancreas to reach the spleen. While the artery assumes a suprapancreatic course 74.1% of the time, an enteropancreatic (18.5%), intrapancreatic (4.6%), and retropancreatic (2.8%) course have also been observed. Occasionally, the splenic artery divides into two or more branches with supra- and enteropancreatic courses. The artery reaches the hilum by passing through the splenorenal ligament. Prior to entering the hilum of the spleen, the splenic artery typically divides into terminal branches (97%). Two terminal branches are common (63.1%) followed by four (18.8%) six (9.7%) and more than six (5.6%). These terminal branches are also known as lobar arteries, since each branch supplies a corresponding lobe (a lobe is also referred to as a segment) and then may divide into subsequent two to four lobular branches. The lobar arteries do not anastomose with one another and therefore supply individual segments of the spleen but the lobular arteries do anastomose with one another. The majority of the time, there are two primary lobes/segments (92.8%) but three primary segments have been observed. In association with these, a superior polar segment (29.3%), inferior polar segment (44.8%), and both superior and inferior polar segments (10.5%) are present. The arteries follow the trabeculae and pass into the red pulp. Almost immediately, each artery is invested in the white pulp (lymph follicle). Having given off capillaries to the follicle it re-enters the red pulp and divides into several parallel penicillate vessels.

The splenic artery also gives off branches to the pancreas and stomach. Five to seven short gastric branches arise from the terminal spleen or left gastroepiploic artery to supply the gastric cardia and fundus. For example, the posterior gastric artery arises from the middle of the splenic artery in approximately 40% of patients. The inferior polar artery usually gives rise to the left gastroepiploic artery. The branch called the dorsal pancreatic artery and the greater pancreatic artery arise from the proximal and middle segments of the splenic artery, respectively. These branches may also provide minor collateral supply to the spleen.

Vein. The splenic vein form the principal drainage of the spleen and is part of the hepatic portal system. The splenic vein has a straighter course than the artery, but runs generally in close relation to the artery. Five or six large veins draining the spleen at the hilum unite to form the splenic vein which grooves on the pancreas on the upper back side of the pancreas, below the splenic artery. The splenic vein connects with the inferior mesenteric vein (returning blood from the rectum, sigmoid, descending colon) before joining the superior mesenteric vein (returning from the small intestine and cecum, ascending, transverse colon) to form the portal vein, which drains the blood from these organs into the inferior vena cava. Other veins that drain into it include the short gastric, left gastroomental, and pancreatic veins.

Innervation of the Spleen and the Inflammatory Reflex

Figure 6A:
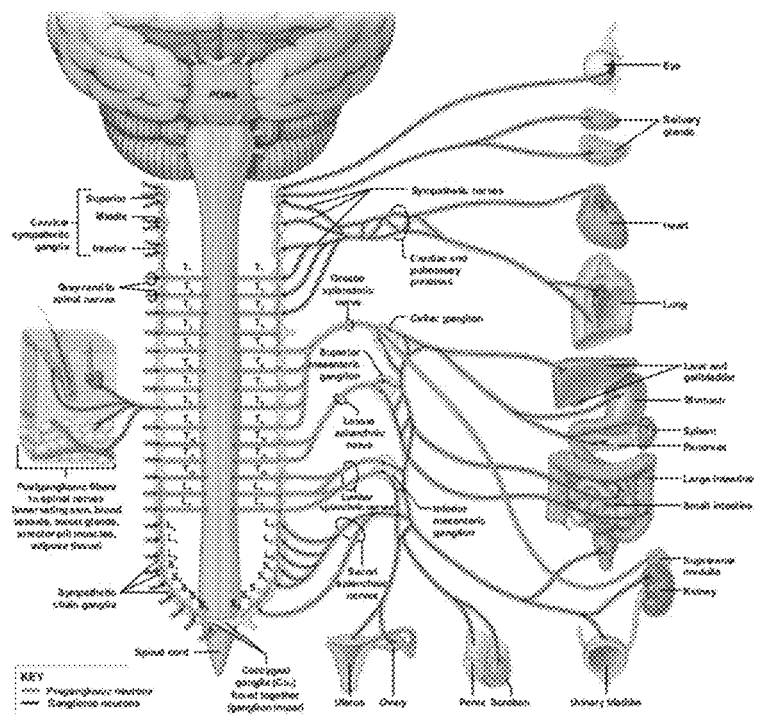
FIGS. 6A-6B shows the sympathetic (6A) and parasympathetic (6B) nervous system innervating the spleen and other organs.

Sympathetic innervation: As shown in FIG. 6A, the sympathetic pre-ganglionic fibers from the T6-T9 thoracic sympathetic chain ganglia travel along the greater splanchnic nerve and to celiac plexus, the celiac ganglion and the esophageal plexus. Sympathetic nerves from these celiac, mesenteric and esophageal plexi and ganglion innervate the spleen and other organs involved with inflammation, cytokine activation and release. They include the liver, stomach, pancreas the adrenal medulla. In addition, some nerve fibers from the thoracic T9, T10, lumbar (L1-L5) and sacral (S1-S4) sympathetic chain ganglia may also travel along the lesser splanchnic nerve, lumbar splanchnic nerve and sacral splanchnic nerves synapsing near the near the superior mesenteric ganglion, inferior mesenteric plexus and ganglion and the hypogastric plexus.

In most cases, sympathetic and parasympathetic nervous systems have opposing actions of activating and inhibiting a physiological response and form feedback loops to regulate organ function and maintain homeostasis inside the body. There is increasing evidence that the two arms act together in certain diseases and, in particular, at certain stages of disease. A method to treat sepsis, by leveraging the sympathetic nervous systems actions in concert with the parasympathetic nervous system to resolve inflammation and develop immune memory to combat infections from the same pathogens in the future can be desirable.

The spleen is primarily innervated by the splenic nerve/nerves which course along the splenic artery (formerly known as the lienal artery). The cell bodies of these nerves primarily originate in the mesenteric/superior mesenteric and celiac ganglion, although fibers may also be found to originate from other ganglia. Although the majority of the splenic innervation is perivascular in distribution, noradrenergic nerves also accompany smaller vessels without smooth muscles cells or travel through the parenchyma, suggesting a direct immunomodulatory role. Noradrenaline or norepinephrine is the primary neurotransmitter thought to mediate this given the presence of adrenoreceptors on lymphoid cells. Noradrenaline may control the equilibrium between pro-inflammatory and anti-inflammatory neuro-immuno-modulation. The nerve bundle(s) primary contain noradrenergic postganglionic nerve fibers (sympathetic efferent, catecholaminergic, 98%) which enter the spleen together with the splenic artery, run along the trabeculae in plexuses and extend into the white pulp along the central artery where they terminate in the periarterial lymphatic sheath and marginal zone/sinus and the parafollicular zone. The greatest density of nerve fibers are found in the periarterial lymphatic sheath. Nerve fibers may be co-localized with T-cells, macrophages (e.g. ED3+ cells), as well as B cells residing in the marginal zone where lymphocytes enter the spleen. The richest innervation is in T-cell zones and in areas of mast cells and macrophages, whereas follicular and nodular zones where B cells mature are poorly innervated. Scattered nerve fibers have been observed traveling into the red pulp.

Peptidergic innervation has been identified in the spleen through neuropeptide immunoreactivity illustrating NPY-like, Met-enkephalin-like, and cholecystokinin-8 (CCK)-like, neurotensin-like labelling of the central artery of the white pulp and its smaller arteries. Also, VIP-positive nerves accompany large arteries and central arterioles ending in the white pulp. Several groups have also found 'low-pressure baroreceptors' in the spleen that are thought to reflex with the sympathetic nerves, however significant afferent innervation in humans is thought to be unlikely, particularly outside of the hilum/hilus of the spleen. Other organs and related neural networks are involved with inflammation and cytokine release. The lesser splanchnic nerve originates from T10 and T11 thoracic sympathetic chain ganglia and connects to the superior mesenteric ganglion plexus (SMGP). Post-ganglionic nerve fibers from the SMGP innervate the small and large intestine. Pre-ganglionic sympathetic nerve fibers from the T12 thoracic and L1 and L2 lumbar ganglia form the lumbar splanchnic nerves and connect near the inferior mesenteric ganglion plexus (IMGP); post-ganglionic renal nerves from the IMGP innervate the kidney. Post-ganglionic sympathetic nerves from the cervicothoracic (C3-T4 T12) ganglia form the cardiac and pulmonary plexus and innervate the lung, which is an important organ for the entry of infectious pathogens into the body and resolution of inflammation. Local chemical neuromodulation of these nerve pathways to regulate the activation and circulation of cytokines and treat sepsis and related inflammatory disorders are described in the present invention.

Figure 6B:
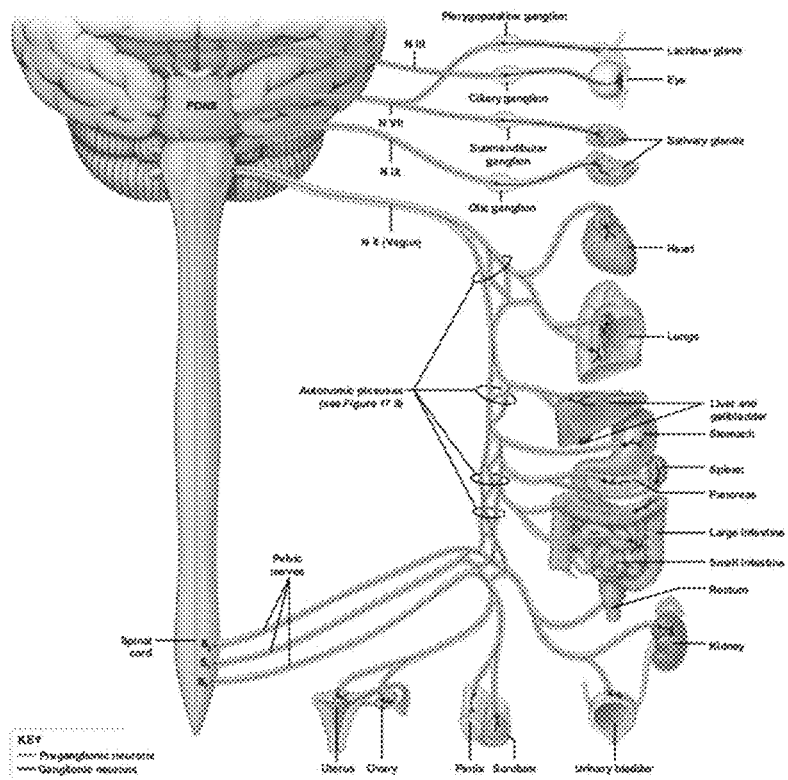

Parasympathetic innervation: The parasympathetic nervous system modulates the neural activity in of the spleen and thus is an indirect modulator through the vagus nerve (cranial nerve X), as shown in FIG. 6B. There are few, if any, vagal nerve fibers innervating the spleen. The pre-ganglionic vagus nerve branches at several locations along the thoracic trunk forming various autonomic nerve plexi (or networks); the parasympathetic fibers (cholinergic, acetylcholine) synapse on the celiac, superior mesenteric, and other ganglia in the vicinity. Some of these fibers innervate the postganglionic sympathetic nerves that innervate the spleen.

Clinical Procedure and Devices

Drug formulations described above may be injected locally, near the splenic nerve and other nerve target sites inside the body, under x-ray (fluoroscopy or angiography), electron beam computed tomography (EBCT or CT), magnetic resonance imaging (MRI), optical coherence tomography (OCT), external ultrasound (ultrasonography, color Doppler sonography) or intravascular ultrasound (IVUS) imaging using a device. Imaging may be used to insert the device into the body and advance it near the nerve target site, visualize the nerves and surrounding tissue, verify location and inject the drug locally near the splenic nerve or other nerve tissue. Nerve stimulation may be performed to confirm the target nerves innervating organs, nerve sites for drug administration and measure the nerve signaling activity before, during and after treatment.

The splenic nerve and other nerve target tissue sites associated with inflammation and/or sepsis may be accessed using different routes. These include open surgery, laparoscopic methods, direct access using percutaneous needle or catheter-based techniques or endovascular methods using a catheter-based device. Among these, the percutaneous and endovascular methods are preferred to minimize the additional injury, trauma and infection in critically ill patients from surgery or laparoscopy.

Percutaneous Access Needle and catheter-based devices: The device may be, in some embodiments, a simple syringe connected to a long 18-33 gauge needle (like a biopsy needle) to reach the splenic nerve site under x-ray, CT, MRI, or ultrasound imaging. Ultrasound and CT can be preferred for needle-based treatment because of real-time guidance and shorter time to reach the target. The splenic artery, splenic hilum and surrounding tissue and organs may be used as land marks to administer the drug near the splenic nerves or to the spleen itself. Coaxial needles may be used in order to provide better structural support for low-caliber needles to penetrate the tissue. In addition, the coaxial method allows the introduction of microelectrodes and electrophysiology (EP) catheters to measure nerve activity and/or stimulate the nerve tissue before, during and after treatment through a single needle.

Different approaches may be used to access the splenic nerve. The patient is consciously sedated and placed in the lateral decubitus position. The needle is inserted using a subcostal approach under CT, along a direct and shortest trajectory, avoiding the colon, kidney, lung and pleura. Once the needle is in position, a negative aspiration test is performed to verify that the location of the needle is outside blood vessels (no puncture of the splenic artery, splenic vein, or other surrounding blood vessels is indicated by the lack of blood draw during aspiration) or the peritoneum. Next a small amount of dilute contrast material is injected under fluoroscopic or CT guidance to further ensure that the needle tip is in the correct position and there no peritoneal spill, no puncture of nearby blood vessels, bowel, or the kidney. Once the position is verified about 0.01-10 mL of the drug delivery system is injected near the splenic nerve or another nerve target site using the syringe. The needle is removed and the puncture site is closed. In one embodiment, direct venous access can be obtained in the perihilar splenic vein with a 21 gauge Chiba needle under ultrasound or fluoroscopic guidance. Optionally, access may be possible through a transsplenic route. The puncture site is typically between the $7^{th}$ and $9^{th}$ intercostal space on the left midaxillary line. For hilar delivery, the needle is advanced to the splenic hilus and, after confirmation that the needle is not in a vessel, the drug delivery system can be administered. Alternatively, if vascular access is desired, the core of the needle can be removed and pulling back slowly until blood can be aspirated followed by contrast medium to confirm that the tip of the needle is inside the vein or artery. A 0.018" guide wire can be introduced and then a 5 F catheter sheath is pushed into the artery/vein through the exchanged guide wire. Direct percutaneous endovascular access of the splenic vessels provides a less cumbersome approach than femoral artery puncture and improves the maneuverability of the catheter tip with fewer exchanges. Microcatheters advanced through the lumen of the needle can then access the spleen at the terminal, lobar, and lobular arteries and arterioles, allowing for the placement of the drug delivery system in closer approximation to the immune cells.

In another embodiment of the device, the needle may be exchanged for a flexible 4-10F catheter tube. After aspiration of the catheter and injection of contrast through the catheter to confirm target location, 0.01-10 mL of the drug formulation may be injected near the nerve target site.

In yet another embodiment an EP catheter or a microelectrode may be inserted to reach the nerve target site to confirm the location of the nerve target site. The nerve tissue may be electrically stimulated and the reactive signal response may be measured to verify the disease condition before treatment. After local administration of the drug formulation to affect nerve or ganglion function, the EP catheter or the electrode may be stimulated again to measure the nerve signaling, to verify that the treatment is effective and complete. The EP stimulation catheters and microelectrodes may be introduced through the inner lumen of the needle. Alternatively, the catheter and electrode may be left in place adjacent to the needle while treatment is being delivered to continuously monitor the change in nerve signaling during treatment. In some embodiments, the target nerves can be stimulated either before or after drug delivery as a synergistic combination.

An ultrasound (e.g., 3.5 MHz curvilinear probe) probe may be used to locate the spleen and surrounding tissue/organs in real-time and select the best trajectory to advance the needle and the catheter. Color Doppler imaging may be used to avoid damage to major blood vessels along the needle tract. When ultrasound is not sufficient for image guidance, CT may be used for needle or catheter guidance with minimal disruption to the patient. For CT-based treatment, a spiral non-contrast CT of the spleen may be performed with a radiopaque marker or grid to identify the shortest and safest route for introducing the needle and the catheter.

In one embodiment of the needle-based device, one or more nanoelectrode sensors are incorporated at the tip of the needle (on outer the surface), to measure the electrical signals transmitted from the target nerve tissue, ganglion or portion of the nerve. Nerve activity may be measured directly using a wired connection to a data logger or remotely using a wireless connection. For example, planar nanoelectrode arrays (PNAs) have been used to measure SNA near the stellate ganglion using a wireless transmitter.

In another embodiment, the needle itself may be used to measure the SNA activity of the nerve, ganglion or portion of the nerve. Typically, 18-33G needles are made from stainless steel, high-carbon steel and cobalt-chromium alloys. They may be coated with high conductivity elements like gold, tungsten, tantalum, niobium and chromium, etc., to improve conduction and the nerve signal measurements. Such measurements may be used to study the efficacy of treatment by monitoring the signal, before, during and after treatment, e.g., local administration of a drug formulation to modulate and/or interrupt nerve signaling.

In another embodiment of the present invention the treatment may be performed under MRI. MRI may be used to locate the splenic nerve or other nerve targets involved with inflammation and sepsis, and introduce the needle to the target nerve location. Most needles are made of metals and alloys like stainless steel, high-carbon steel and cobalt-chromium alloys. Metallic needles may cause artifacts under CT and MRI imaging which makes it difficult to identify surrounding tissue during clinical treatment. MRI and CT compatible needles may be made from niobium, tantalum, platinum, zirconium and palladium-based alloys, which have low magnetic susceptibility and reduce artifact size and enhance needle visibility. Other examples of non-metallic materials include ceramics (zirconia, alumina), carbon fibers, polymers and their composites, etc. Needle tip designs may be coated with bismuth and other low magnetic susceptibility materials to clearly identify the target nerve tissue.

Locations of Drug Delivery.

In one embodiment, the drug delivery system can be delivered after saline hydrodissection to create a potential space between the peritoneum and the capsule of the spleen or the two folds of the peritoneum. In another embodiment, the drug delivery system can be injected or placed within the folds of the splenorenal ligament, which contains the splenic artery, vein, and sympathetic nerves. In this manner, the drug delivery system can be delivered proximal to the hilum or within the hilum itself. The ligament itself advantageously provides a boundary for the spread of an injectable drug delivery system such as an in situ forming gel, which can be entirely or substantially entirely contained within the folds of the ligament in some embodiments without spreading into unintended locations outside of the folds of the ligament. In another embodiment, the drug delivery system is delivered along, e.g., within the folds of the gastrosplenic ligament to communicate with the sympathetic nerves there. In some embodiments, the therapeutic agent is delivered at or proximate a location where the splenic artery enters the splenorenal ligament, and the therapeutic agent is allowed to flow in a controlled manner, e.g., unidirectionally between the folds of the splenorenal ligament toward the splenic hilum.

In another embodiment, a gel depot can be placed between the splenic capsule and the diaphragm or peritoneum. A potential space can be created by, e.g., blunt or saline hydrodissection or the formulation itself can hydrodissect and then a drug delivery system can spread across the surface of the spleen. Depending on the extent of the spread, about 10% to about 100% of the spleen may be covered in the drug delivery system. An in situ forming hydrogel, in which the components are a low-viscosity liquid on injection and then react to form a viscous hydrogel, would be desirable in some embodiments as the low-viscosity liquid can readily spread across the spleen. In yet another embodiment, the lienorenal ligament and gastrosplenic (gastrolienal) ligament bound the spread of the depot system.

In yet another embodiment, the spleen can be accessed from the stomach, lung, kidney or descending colon at the lower ribs (R9-R11) or lower thoracic (T11-T12) levels. In this manner, the system can be delivered to the spleen hilum or the spleen itself. In these embodiments, a minimally invasive needleoscopic approach would provide access from the lumen of one organ, such as the stomach, to the hilum of the spleen.

In another embodiment, a solid depot system can be placed in one or more trabeculae passing into the spleen. In another embodiment, a drug delivery implant can be delivered into the vascular sinusoid through a needle with the lumen of a 25 XXTW needle. In another embodiment, the drug depot system may be delivered to or in proximity to the pancreatosplenic lymph nodes which lie along the splenic artery. In yet another embodiment, the drug depot system may be delivered to the nodes in the hilus of the spleen which receive lymph vessels from the splenic capsule. Of note, only the lymph from the capsule and trabeculae, pass to the pancreatosplenic lymph nodes. In another embodiment, the drug depot system is placed around the splenic vein as this is the route by which the pulp drains from the spleen. In patients with accessory spleens, as may be found in the splenorenal ligament, the therapy can be delivered to these as well as needed.

Endovascular Access-Catheter-Based Devices:

Another embodiment of the device may be an endovascular catheter, with multiple lumens, ports and elements, to assist navigation through the human blood circulatory system to reach the splenic nerve or other nerve target sites, and locally administer the drug formulation to treat sepsis and related inflammatory diseases. The catheter device may be introduced and advanced from the arterial or venous vessels of the circulatory system. Typically, the treatments involve the use of introducer kits, flexible guidewires, guiding catheters, sheaths and other ancillary devices by those skilled in the art (interventional physician specialists) to reach the target tissue location, and are not described here.

Typical endovascular access or puncture sites for introducing the catheter are the femoral artery, femoral vein, brachial artery, brachial vein, radial artery, radial vein, carotid artery, jugular vein, subclavian artery and subclavian vein. After the vessel is punctured, catheters are advanced from the puncture sites to reach one of the blood vessels adjacent to the splenic nerve or other target nerve locations under x-ray fluoroscopy, CT, ultrasound, optical coherence tomography (OCT) or MRI guidance.

A typical endovascular catheter used to deliver the drug formulation near the splenic nerve or other nerve target sites comprises at least three design elements. The first element can be a long hollow cylindrical shaft that facilitates advancement through blood vessels along a thin guidewire used in endovascular interventional procedures. The second element can be a positioning anchor that locks the position of the catheter relative to the nerve target site. In an exemplary catheter, the positioning anchor could be a balloon, which upon activation (or dilation though a lumen that exits through an inflation port on the proximal end, outside the body), conforms to the luminal surface of the vessel and stabilized the position of the device. The third element can be an injection component that may be in fluid communication through a separate port on the proximal end of the catheter (outside the body). When the injection element is activated, it penetrates the vascular wall to reach the target nerve tissue and locally administers the drug formulation near the target nerve tissue with minimal injury to the vessel wall.

In some procedures, the catheter may introduced into the femoral artery and advanced through the iliac artery, the abdominal aorta and the celiac trunk into the splenic artery under x-ray fluoroscopy guidance. Once the position of the catheter is confirmed under angiography, the balloon may be inflated to lock the position of the catheter. The microneedle (injection element) may then be activated to penetrate through the splenic artery wall and reach the perivascular space surrounding the splenic artery. A small amount of contrast may be injected to verify the location of the microneedle relative to the splenic nerve under angiography. After confirming the location, the drug formulation may be injected near the splenic nerve. After treatment, the injection element may be deactivated, the balloon is deflated and the catheter is removed from the body. The splenic artery may be accessed through other routes (radial artery, radial vein, femoral vein, brachial artery). Other nerves may similarly be accessed through different vessels of the circulatory system that are adjacent to the nerve target sites.

Figure 5G:
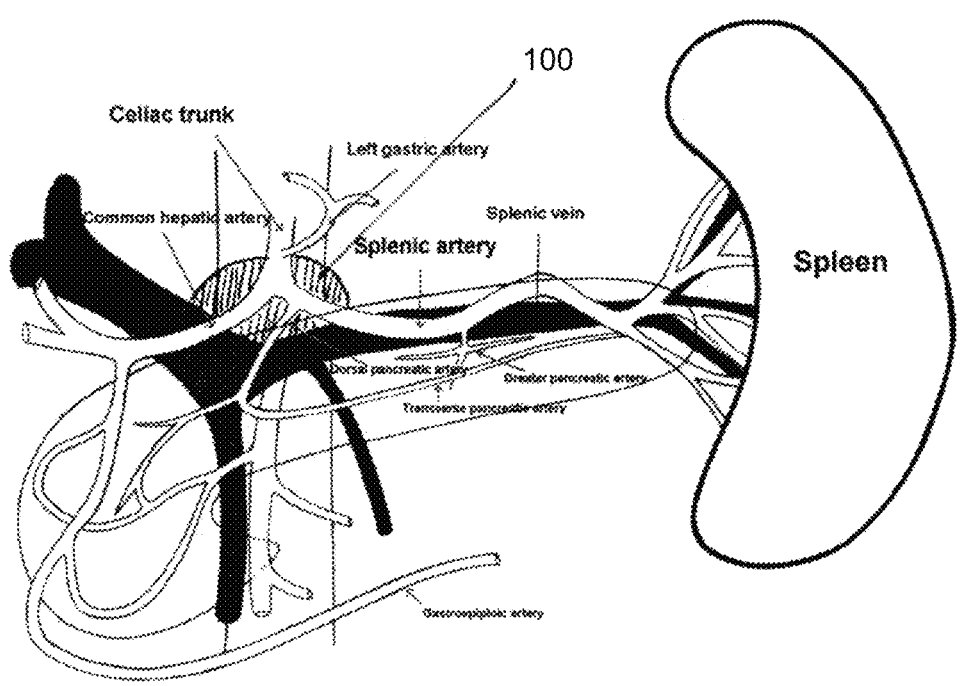
FIGS. 5G-5I schematically illustrate non-limiting examples of potential drug delivery sites.
Figure 5H:
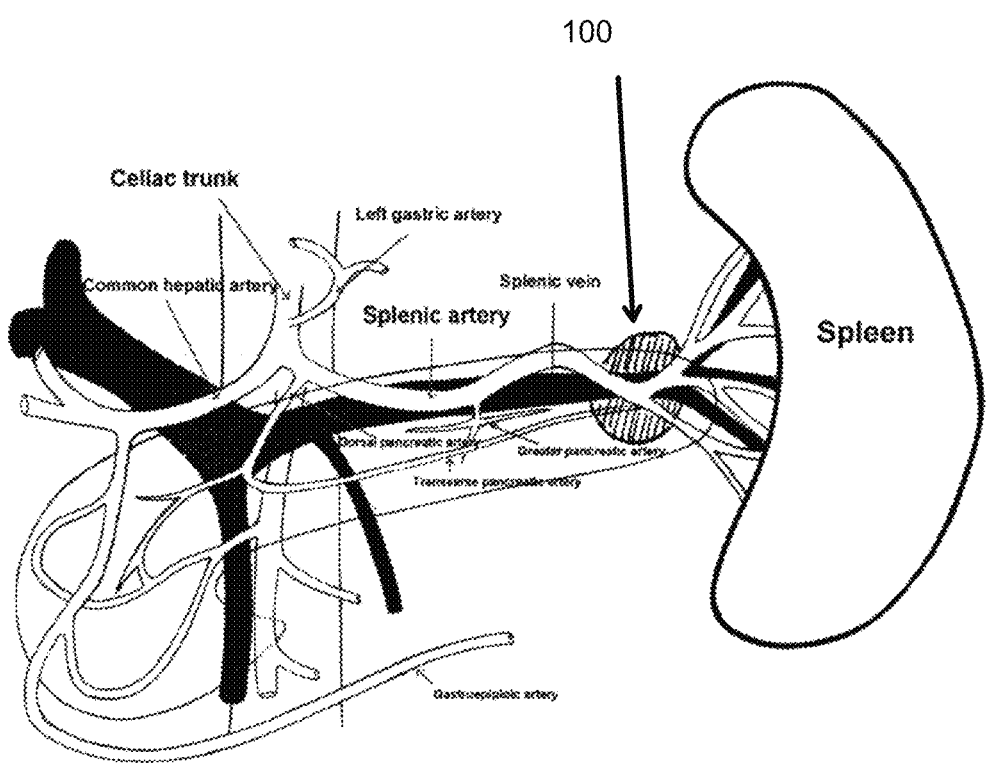
Figure 5I:
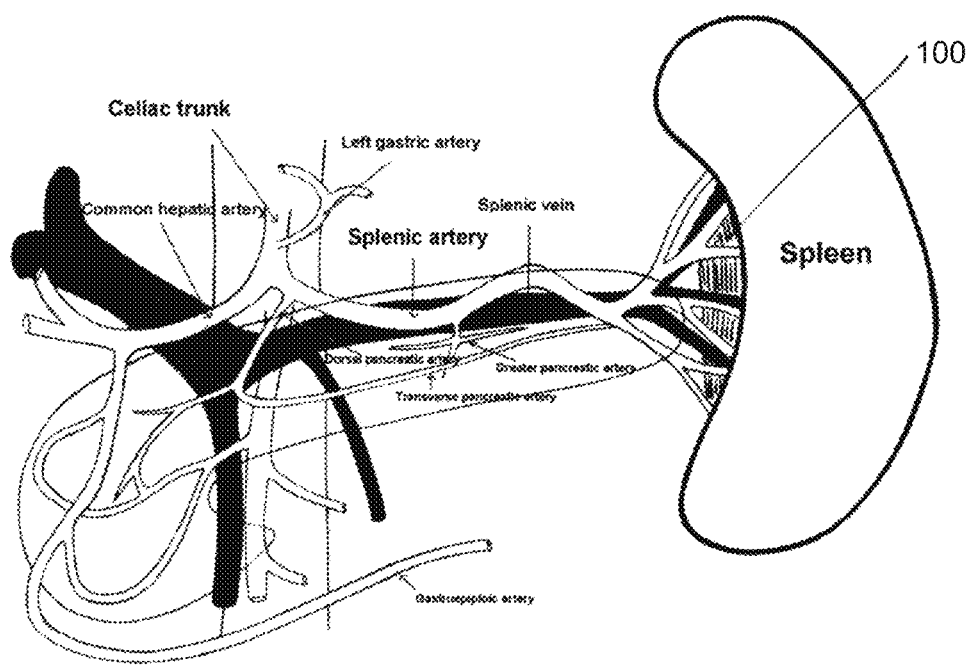

As shown in anatomical target sites illustrated, for example, in FIGS. 2B, 4A and FIG. 5A, the catheter may be advanced to other vessel locations and deployed at those locations to reach the splenic nerve. These vessels include the celiac artery, celiac vein, bifurcation of the celiac and splenic artery, bifurcation of the celiac and splenic vein, the left gastro-epiploic (or gastro-omental) artery, the left gastro-epiploic vein, the splenic hilum (venous and arterial access), the left gastric artery, the left gastric vein, the short gastric arteries, the short gastric veins, and related bifurcations and ostia of these vessels. FIG. 5G schematically illustrates drug delivery, such as via a gel 100 for example which can be delivered proximate the celiac trunk, where the splenic artery arises. FIG. 5H schematically illustrates drug delivery, such as via a gel 100 for example which can be delivered proximate where the splenic artery branches into smaller splenic branches, e.g., after the splenic artery enters the splenorenal ligament. FIG. 5I schematically illustrates drug delivery, such as via a gel 100 for example into the hilum of the spleen, which can be accomplished via delivery of a therapeutic agent delivery system directly into the hilum, or in some embodiments flowing into the hilum between the folds of the splenorenal ligament, for example (e.g., in some embodiments as a result of delayed flow distally into the hilum after the initial delivery location of FIG. 5H in some cases). Other potential therapeutic agent delivery sites can be utilized, including but not limited to any anatomical site(s) and approach method disclosed herein depending on the desired clinical result.

In one embodiment of the device, the anchoring element to stabilize the position of the catheter may be a compliant balloon made from a homogenous material to accommodate different sizes (diameters) of the splenic artery. In other embodiments, the balloon may be made from different materials so that portions of the balloon are compliant to ensure that the injection element is oriented towards the target nerve location. In another embodiment, the balloon may incorporate an electrical sensor (that accommodates balloon expansion) to locate the splenic nerve or other nerve sites, ganglia and nerve plexi, based on local nerve-signaling activity. In yet another embodiment, the anchoring element may be a spring or self-expanding mesh or stent-like structure. The anchoring element is constrained with a sheath of the catheter. Once the catheter is advanced to the target nerve site, the sheath is retracted so that the anchoring element is released to expand and conform to the vessel wall.

The self-expanding anchoring element may be pre-shaped and constrained in such a way as to orient the injection element towards the nerve target site upon release.

In one embodiment of the device, the injection element is a microneedle (or an equivalent drug delivery element). The injection element may be activated by the anchoring element (balloon expansion or unconstraining the self-expanding mesh) or activating it separately using a handle to advance the microneedle across the vessel wall to reach the target nerve location. The microneedle is designed to of sufficient strength and caliber (between 10-200 microns in diameter) to penetrate the vessel wall, yet small in diameter to minimize vessel trauma, vessel perforation and bleeding complications.

In another embodiment, the injection element may be a needle-less balloon with a micro-aperture. The injection balloon element may administer a small volume (10-500 microliters) of drug formulation to the target nerve tissue through a small aperture from a reservoir, by piercing the tissue under transient conditions (<1 second) of high pressure (between 100-10,000 psi). The method comprises of positioning a delivery device comprising the aperture with the artery and injecting the drug formulation at high velocity out of the aperture, across the artery wall and interacts with the nerve tissue to disrupt nerve signal transmission and treat disease. The micro-aperture can be of sufficient caliber (between, e.g., 10-200 microns in diameter) to avoid injury to the vessel wall (perforation, bleeding) and surrounding tissue. The needleless component is in communication with the drug reservoir and the high pressure injection system on one end (outside the body) and the microaperture in contact with the vessel wall (inside the body). The needleless component could be a balloon, a long injection tube or a series of injection tubes, with a microaperture, in fluid communication with the drug reservoir.

The microneedle injection elements may be used as microelectrodes to monitor nerve signal activity before, during and after treatment. In one embodiment, one or more nanoelectrode sensors are embedded on surfaces of the microneedle tips to measure the electrical signals near target nerves, plexi or ganglia. Both wired and wireless sensors may be used to monitor local nerve activity.

In another embodiment, the microneedles may be used to stimulate the local nerves and measure the extent of nerve overactivity or identify/verify the regions of abnormal nerve activity or abnormal cytokine activity or abnormal biomarker activity before treatment near the target nerve site. The microelectrodes may be connected to a generator to stimulate the nerves and monitor nerve signal activity before, during and after treatment. In one embodiment, one or more nanoelectrode sensors may be incorporated into the anchoring element to amplify the local nerve signal and assist measurement. Injection and anchoring elements may incorporate additional sensors for activating, amplifying and receiving local nerve signals.

In one embodiment, tip of a 5-Fr or 6-Fr catheter is advanced distally through the splenic artery until it is positioned beyond the dorsal pancreatic artery to prevent off-target delivery to the gastrointestinal tract and pancreas. Similarly, as needed other vessels can be avoided including the pancreatica magna and short gastric branches. A coaxial system may be needed due to the size and tortuosity of the vessels. A coaxial microcatheter may safely allow for access to splenic arteries distal to the hilum. Intraarterial injection of lidocaine (50 to 100 mg) may be performed to decrease patient discomfort and abdominal pain during the procedure. In another embodiment, a 3 French (3-Fr) microcatheter can be advanced into the spleen through the terminal and lobar branches to deliver the formulation beyond the hilum, or posthilar deployment, similar to those employed for superselective distal embolization of the spleen after trauma, may be used to advance the catheter within the spleen. In this manner, specific segments of the spleen can be selectively targeted as needed.

In another embodiment, the catheter may be introduced through the radial artery or brachial artery to reach the splenic artery and the splenic nerves surrounding the splenic arteries and veins. The radial or brachial veins may also be punctured to introduce and advance the catheter through the splenic vein to access the splenic nerve fibers, other target nerves, ganglia and nerve plexi.

Delivery systems for injecting polymer and gel-based formulations: The composition mixtures of the dehydrated hydrogel precursors and the drug molecules may be delivered using several delivery systems. They may be delivered using, for example, pre-filled syringes or gas powered atomizers. Other delivery methods include aerosolizing apparatus (Inhale Therapeutics, Aradigm Corp.) and pneumatic, needleless injectors (Powderject Ltd., U.K.; Bioject, Portland, Oreg.). Pneumatic injectors may be actuated by compressed gases (argon, carbon dioxide, nitrogen, or helium) or springs. The injectors may be partially or fully disposable and often come packaged with a fill needle or vial adaptor to draw the medication or an implant-forming material or solution from a vial into a syringe.

Other Target Organs and Sites: Liver, Lung and Thymus

Liver: The liver is a vital organ located below the diaphragm in the upper right side of the abdomen (FIG. 2B). It plays a major role in metabolism by regulating glycogen storage, plasma protein synthesis, hormone production and detoxification of metabolites.

Blood supply to the liver is provided by the hepatic artery and the hepatic portal vein. The hepatic artery branches from the celiac trunk, which originates from the aorta, and supplies oxygen-rich blood to the liver. Then, it subdivides into the proper hepatic artery (supplying the gall bladder through the cystic artery), gastroduodenal artery (which further branches into the right gastroepiploic artery and the superior pancreatic-duodenal artery) and the right gastric artery (supplying the stomach). These vessels further branch into small capillary vessels called sinusoids, which lead to lobules. The lobules are functional units of the liver and are made up of millions of hepatocytes. Blood flows through liver sinusoids and empties into the central vein of each lobule. The central veins from each lobule merge into the hepatic portal vein, which carries nutrient-rich blood, collected from the spleen, gastrointestinal tract, related organs, pancreas and liver, and drains it into the inferior vena cava.

The liver is innervated by sympathetic and parasympathetic nerves containing afferent and efferent fibers, as shown in FIGS. 6A and 6B. Sympathetic splanchnic nerves originate from the celiac and superior mesenteric ganglia, which are innervated by pre-ganglionic neurons located in the intermediolateral column of the spinal cord between the T7-T12 thoracic vertebrae. Parasympathetic innervation is provided by branches of the vagus nerve (cranial nerve X) which originates in the dorsal motor nucleus (DMV). The nerve fibers enter the liver at the porta hepatis and follow the course of branches of the hepatic artery and portal vein. In addition, the fibrous covering of the liver is innervated by branches of the lower intercostal nerves.

Lymphatic vessels of the liver drain into hepatic lymph nodes, which lie along the hepatic vessels and ducts in the lesser omentum, and empty in the coelic lymph nodes.

Figure 9A:
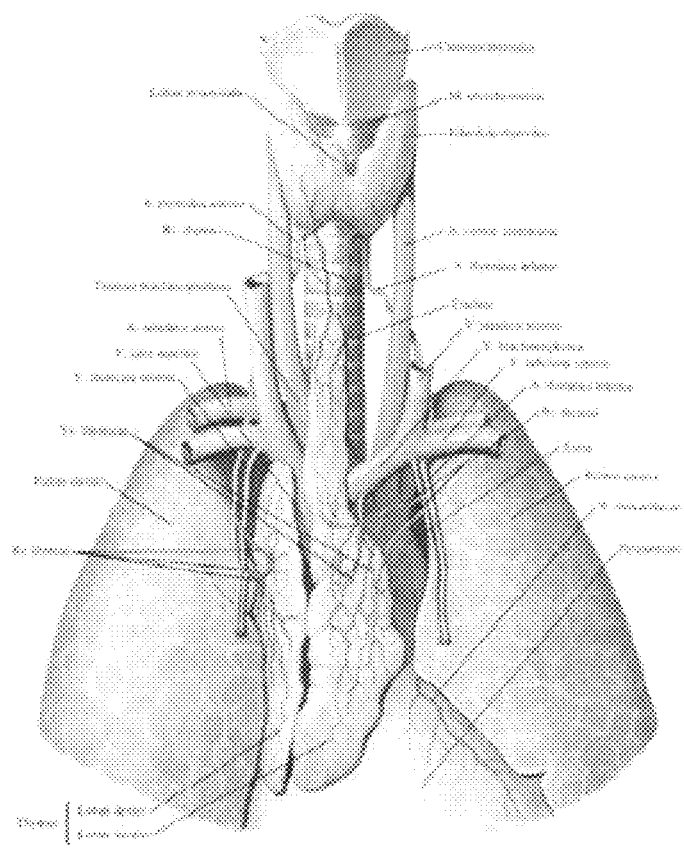
FIGS. 9A-9C shows (A) the anatomical location of the thymus, (B) thymic vessels providing blood supply, and (C) sympathetic and vagus (parasympathetic) nervous systems connected to the thymus, relative to adjacent organs.
Figure 9B:
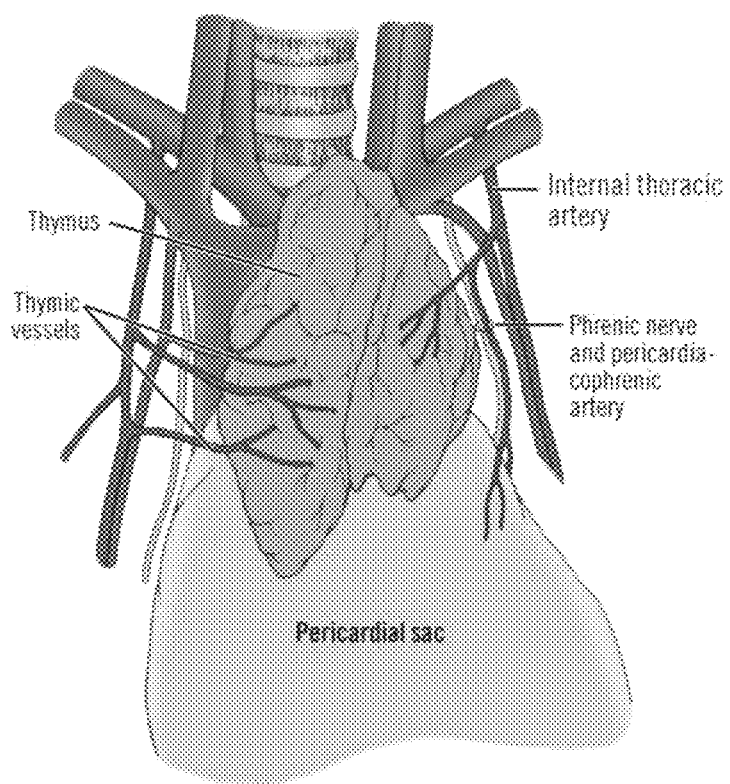
Figure 9C:
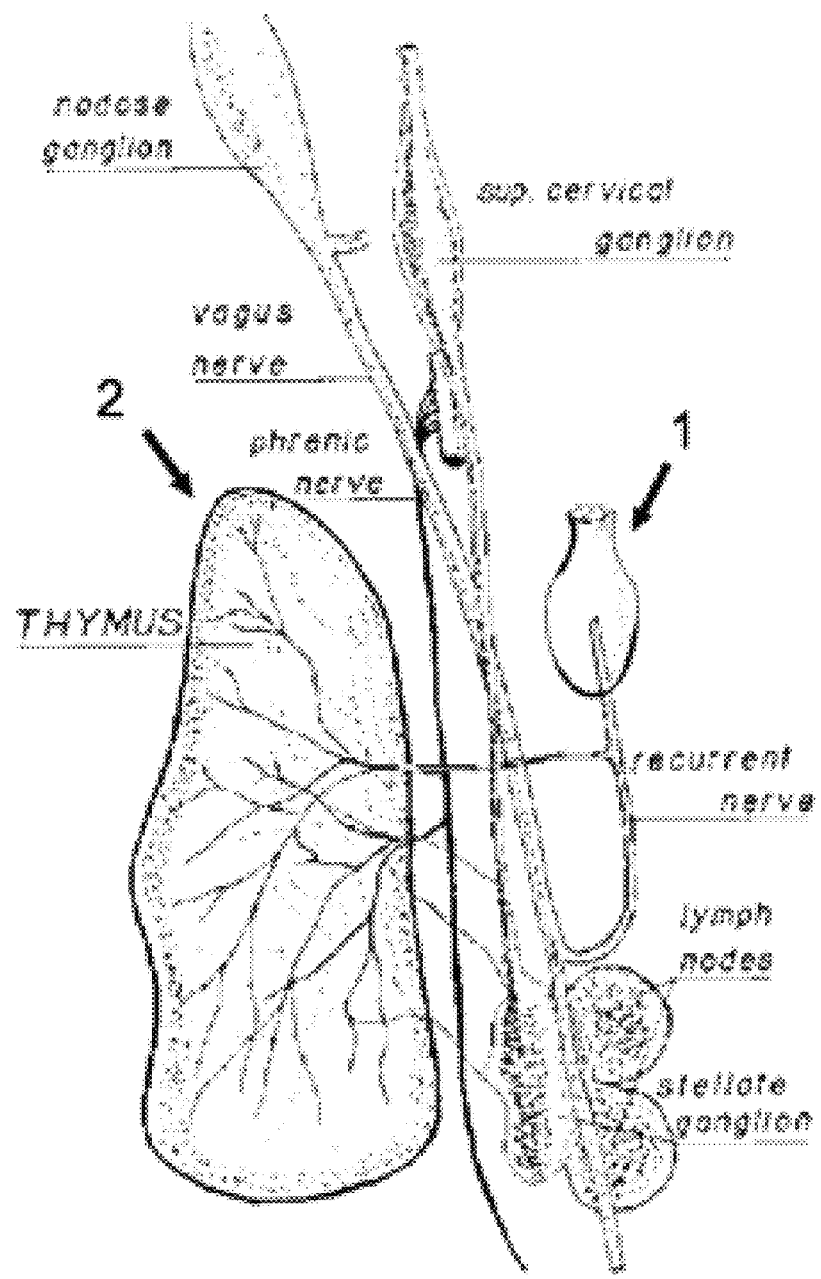

Thymus: The thymus is a lymphoid organ of the immune system which produces T cells or T-lymphocytes and maintains the T-cell levels in the circulation. FIGS. 9A-9C shows (A) the anatomical location of the thymus, (B) thymic vessels providing blood supply, and (C) sympathetic and vagus (parasympathetic) nervous systems connected to the thymus, relative to adjacent organs. As noted above, T cells can play a critical role on the body's immune response, specifically the adaptive immune response against external pathogens. It can include two identical lobes that are located in the anterior superior mediastinum, between the sternum and the heart, extending from part of the neck to the thorax. Each lobe can include several lobules, made up of small nodules, which enclosed in a capsule. The cortical portion is composed of lymphocytes supported by epithelial reticular cells. The medullary portion may have fewer lymphocytes with a network of coarser reticular cells, called Hassall's corpuscles. The medulla is the site where thymocyte development (T-cell receptor gene arrangement) is completed.

Blood supply to the thymus is provided by the internal thoracic artery, the superior thyroid artery and inferior thyroid artery. They subdivided into capillaries and coalesce to form the thoracic, thyroid, and the left brachiocephalic vein (innominate vein).

Nerve supply to the thymus is provided by the vagus (parasympathetic) and sympathetic nerves. Branches from the descendens hypoglossi and phrenic nerves mostly innervate the thymus capsule and the cortex. Postganglionic sympathetic nerve fibers extend from nerve bundles and plexi surrounding blood vessels (perivascular) and innervate the thymic capsule, cortex and corticomedullary junction. Most thymic sympathetic (adrenergic) nerves fibers are located on the outer cortex and do not penetrate the medulla. Thymic parasympathetic (cholinergic) nerve fibers originate from the recurrent laryngeal and phrenic branches of the vagus nerve and innervate the cortex and the medulla. In addition, peptidergic nerves (that release peptide neurotransmitters like tachykinin, substance P, neurokinin A and vasoactive intestinal peptide (VIP), calcitonin gene-related peptide (CGRP)) are also found in the thymic lymphoid microenvironment.

Figure 10A:
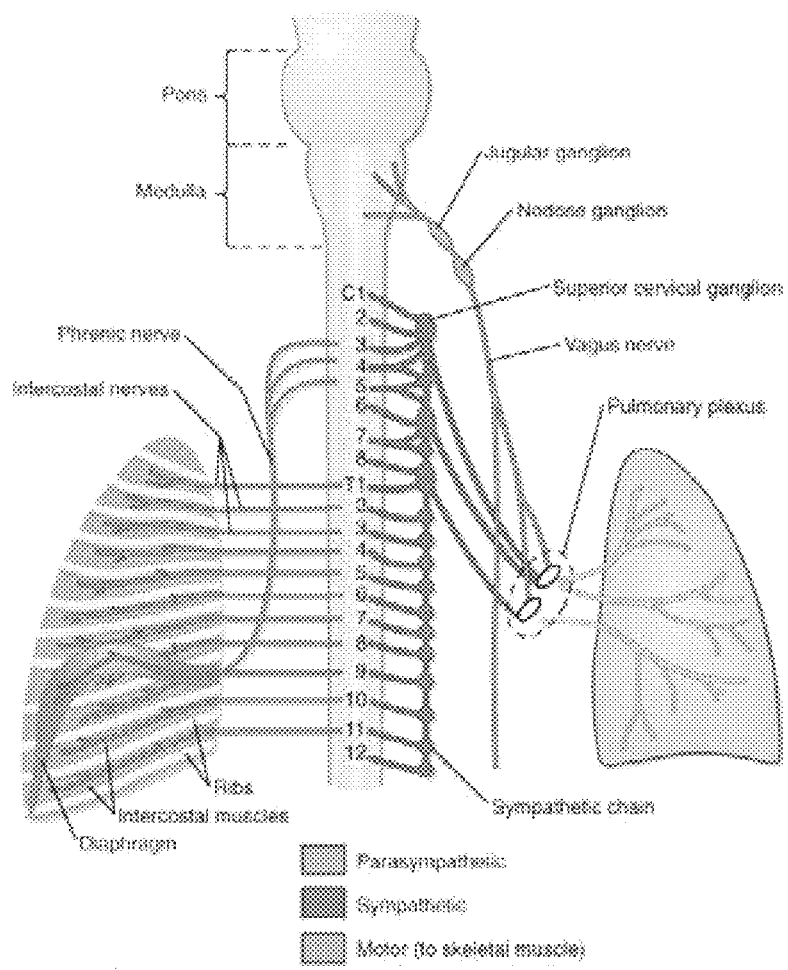
FIGS. 10A-10B illustrates selected lung anatomy.
Figure 10B:
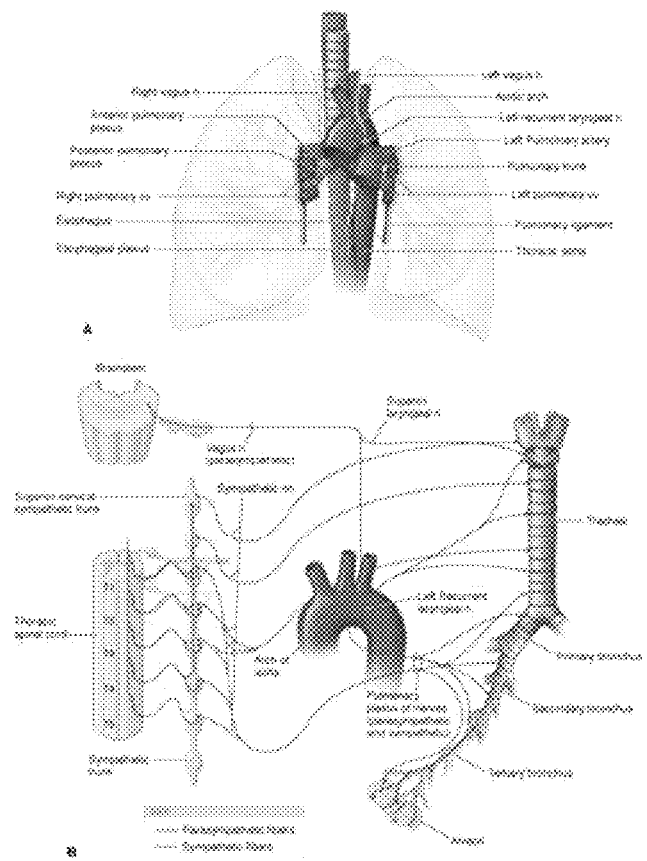

Lung: The lung is the primary organ of respiration which extracts oxygen from the atmosphere and releases carbon dioxide from the blood stream. FIGS. 10A-10B illustrates selected lung anatomy. It is a critical organ in the development of inflammation and progression to sepsis and other chronic diseases like chronic obstructive pulmonary disease (COPD), emphysema etc., The lungs are enclosed within pleural sacs and divided into lobes. The lobes are subdivided into bronchopulmonary segments and lobules. The lungs begin at the trachea and branch into bronchi, bronchioles and alveoli, where the gas exchange takes place.

In addition to respiration, the lungs also protect humans against infection. The lung is lined by epithelial cells which secrete immunoglobulin A and carry mucous (containing antimicrobial compounds like defensins, antiproteases, and antioxidates) that trap airborne pathogens, dust particles and bacteria. The lining also contains macrophages and immune cells that kill microbes and dendritic cells which present antigens to activate components of the adaptive immune system such as T-cells and B-cells.

Blood supply to the lungs is provided by the bronchial circulation of three bronchial arteries, one bronchial artery to the right lung and two arteries to the left lung. They branch from the descending thoracic aorta and supply the bronchial tree. The bronchial veins collect the blood and empty into the azygos vein on the right lung and accessory hemiazygos vein on the left lung. The bronchial arteries and veins constitute the bronchial circulation. In addition, the lung is supplied by the pulmonary blood circulation system from the heart. Two pulmonary arteries (right and left) carry deoxygenated blood to the lungs and branch into thin-walled capillaries. After blood passes through and gas exchange takes place in the alveoli, the capillaries then coalesce to form the pulmonary veins and supply the heart with oxygenated blood. Some bronchial vein branches are connected to the pulmonary veins. Blood supply to the visceral pleura and the parietal pleura are provided by the bronchial circulation and the intercostal arteries, respectively.

The sympathetic and vagus (parasympathetic) nervous systems are connected to the lung and its constituents, related blood vessels and their anatomical locations. Sympathetic and parasympathetic nerve fibers from the pulmonary plexus follow the trachea and bronchial tree (primary, secondary and tertiary bronchi and alveoli) and innervate the smooth muscle and glands of the lungs. Parasympathetic nerve fibers originate from the vagus nerve; release of acetylcholine constricts the smooth muscle lining of the bronchial tree, vasodilated the pulmonary vessels and increases mucous secretion from bronchial glands. The lungs are also innervated by post-ganglionic sympathetic (adrenergic) nerves originating from the T1-T4 sympathetic chain ganglia from the pulmonary plexus. Release of NE acts on b2-adrenergic receptors and causes bronchodilation, vasoconstriction of pulmonary vessels and inhibits mucous secretion.

The lymphatic system of the lungs drains into pulmonary and bronchopulmonary (hilar) nodes, followed by the tracheobronchial (carinal) and paratracheal nodes before connecting with the right lymphatic ducts (right lung) and the thoracic duct (left lung). No lymph nodes are present in the alveolar sacs.

In one embodiment, a drug formulation may be administered locally within the hepatic tissue (including nerves supplying the liver, and its constituents) using delivery methods described below. The drug may cause local neuromodulation or changes in nerve signaling to activate complex protein systems (complement and coagulation systems), vascular and tissue cells (endothelial cells, epithelial cells and adipose tissue) or blood and lymphatic cells (granulocytes, macrophages, monocytes, lymphocytes, T-cells and B-cells), as shown in FIG. 1. The local drug-induced neuromodulation may enhance or decrease the production of inflammation mediators, biomarkers and cytokines and affect the inflammatory response. Examples of cytokines include C5a, C3a, C5aR, C5b-9, ELAM-1, ICAM-1, aPTT, PT, AT, CRP, LBP, IL-6, IL-8, IL-10, CD64, HMGB1, CD48, etc., as listed in FIG. 1.

In another embodiment, a drug formulation may be administered locally within the thymic tissue (including nerves supplying the thymus and its constituents) using delivery methods described below. The drug may cause local neuromodulation or changes in nerve signaling to activate complex protein systems (complement and coagulation systems), vascular and tissue cells (endothelial cells, epithelial cells and adipose tissue) or blood and lymphatic cells (granulocytes, macrophages, monocytes, lymphocytes, T-cells and B-cells), as shown in FIG. 1. The local drug-induced neuromodulation may enhance or decrease the production of inflammation mediators, biomarkers and cytokines and affect the inflammatory response. Examples of cytokines include C5a, C3a, C5aR, C5b-9, ELAM-1, ICAM-1, aPTT, PT, AT, CRP, LBP, IL-6, IL-8, IL-10, CD64, HMGB1, CD48, etc., as listed in FIG. 1.

In another embodiment, a drug formulation may be administered locally within the lung tissue (including nerves supplying the lung and its constituents) using delivery methods described below. The drug may cause local neuromodulation or changes in nerve signaling to activate complex protein systems (complement and coagulation systems), vascular and tissue cells (endothelial cells, epithelial cells and adipose tissue) or blood and lymphatic cells (granulocytes, macrophages, monocytes, lymphocytes, T-cells and B-cells), as shown in FIG. 1. The local drug-induced neuromodulation may enhance or decrease the production of inflammation mediators, biomarkers and cytokines and affect the inflammatory response. Examples of cytokines include C5a, C3a, C5aR, C5b-9, ELAM-1, ICAM-1, aPTT, PT, AT, CRP, LBP, IL-6, IL-8, IL-10, CD64, HMGB1, CD48, etc., as listed in FIG. 1.

Other organs and associated nerve tissue may also be treated through local administration of drug formulations described below to treat inflammation, sepsis and restore organ function (FIG. 1). The target tissue and organs comprise, and not limited to renal nerves, adrenal gland, adrenal nerves, pulmonary nerves, splanchnic nerves, lymph nodes, celiac ganglion, sympathetic chain ganglia, pancreas, intestine, gut and associated nerves that innervate these organs and immune cells affecting circulating cytokine levels.

Drug Neuromodulatory Effects: Mechanism of Action

In order to leverage the sympathetic nervous systems modulation of splenic immune function, the 1) sympathetic nervous system can be stimulated directly to stimulate endogenous norepinephrine production and other co-transmitters within the spleen, 2) the sympathetic nerve release of norepinephrine can be augmented to provide higher local levels of neurotransmitters, cotransmitters, or others agents that act to mimic the effect of norepinephrine, 3) drug delivery directly to the target cells that bind norepinephrine, such as the macrophages and lymphocytes, can be modulated directly and independently of the sympathetic nervous system.

Neurotransmitters. Neurotransmitters and other chemicals released by the nervous system to primary and secondary lymphoid organs. The ANS, and particularly sympathetic afferent and efferent nerves liberate catecholamines, acetylcholine, and peptide transmitters at the synapse to their effector cells in the spleen. These include neuropeptide Y (NPY), substance P (SP), calcitonin-gene related peptide (CGRP) and vasoactive intestinal peptide (VIP), among others. Noradrenergic and neuropeptidergic nerve fibers are found adjacent to immune cells in the spleen and regulate immune responsiveness and thus would be of interest to deliver directly into the lymphoid microenvironment directly through a drug delivery system.

As mentioned previously, the alpha-7 nicotinic acetylcholine receptor ($\alpha 7$ nAChR) is also found on these immune cell and therefore the local delivery of nicotine, for example, may be desirable to stimulate. In one embodiment, 10 micrograms to 1 gram of nicotine can be delivered in a drug delivery system to the target site. Also as mentioned previously, the immune cells are also modulated through their adrenergic receptors, such as beta-adrenergic receptors which bind to norepinephrine released from the catecholaminergic nerves. In one embodiment, beta-agonists are delivered locally to the spleen to modulate immune cells.

The following describes drugs that are directed primarily towards modulating the splenic nerve directly. Neuronal noise is a general term that is defined herein as the random influence on the transmembrane voltage of single neurons, and by extension, the firing frequency of neural networks. This noise may influence the transmission and integration of signals from other neurons, as well as, alter the firing activity of neurons in isolation. The noise may also affect innervated tissue and generate disturbances in cell signaling and organ function. Abnormalities in nerve signaling may lead to, or may be associated with, different inflammatory conditions listed in the aforementioned embodiments.

Ion pump and ion channel antagonists: Ion channels are ion-permeable pores in the lipid membranes of all cells. The channels open and close in response to stimuli, and thus gate the flow of specific small ions. The ions flow downhill thermodynamically to enter or egress cells.

Ion pumps are non-ion permeable pumps in the lipid membranes of all cells that use chemical energy (in the form of adenosine triphosphate (ATP) hydrolysis) to power the transport of ions against an electrochemical gradient (uphill, thermodynamically).

Both ion channels and ion pumps are highly abundant on cells in a ganglion, as ion homeostasis (the regulation of ions that enable maintenance of normal cellular responses) is a hallmark of a neuron. Indeed, the average charge difference across a neuronal membrane when at rest (~70 mV) differs significantly from the charge difference across the membrane of an actively firing neuron (~30 mV). The neuron utilizes both ion channels and ion pumps for membrane depolarization (opening of sodium channels) and repolarization (opening of potassium channels). The Na+/K+ pump is responsible for maintaining the electrochemical gradient of the resting potential (~70 mV).

Perturbations in neuronal activity may lead to prolonged resting periods, cessation in neuronal firing (block) and/or nerve death.

Conductance fluctuations in ion channels may be driven by thermal fluctuations, and in some sense, amplify these fluctuations. These protein channels are made up of subunits and complex domains that weave in and out of the cytoplasmic membrane, and undergo spontaneous changes in conformations between various open and closed states in a heat-influenced manner. The open state is characterized by a pore that allows specific types of ionic species to migrate through the membrane, under the influence of an electrochemical driving force. Such a force arises due to gradients in voltage and ionic concentration across the neural membrane. In a neuron, where there are a large number of channels, single channel fluctuations have minimal impact on neuronal ion homeostasis, multiple channel fluctuations may be required in a neuron to cause action potentials.

The main component of noise experienced by a neuron originates in the myriad of synapses made by other cells onto it. Every spike arriving at this synapse contributes a random amount of charge to the cell due to the release noise. During the time a channel is open, ions migrate in complex ways and varying amounts across the membrane. The associated fluctuations are called channel shot noise. Continued perturbations may lead to downstream dysfunction within a neuron and downstream from said neuron. Discussed herein are drugs that may be used to regulate ion flow by agonistic or antagonistic interaction with ion channels or ion pumps to reduce shot noise, synaptic noise, or to regulate neuronal activity in the ANS.

In some embodiments, it is advantageous to contact a tissue with a channel blocker to affect ganglionic activity in the adjacent tissue. In other embodiments, it is advantageous to contact a tissue with an ion pump antagonist to affect ganglionic activity in the adjacent tissue. Examples of channel blockers and ion pump antagonists for use in modulating ANS activity in ganglionic cells, nerve fibers, ganglia and nerve plexi include the following.

Na/K, H/K and vacuolar ATPase blockers: Cardiac glycosides may be used to locally modulate the ANS. They inhibit Na(+)/K(+) ATPase, disrupt ion homeostasis, control aberrant ion homeostasis, induce cell block or induce cytotoxicity in neurons. Cardiac glycosides may also regulate gene expression of MDR (Pgp), MRP (MRP1), CFTR or cAMP-activated Cl-channels, and others. 3,4,5,6-Tetrahydroxyxanthone is another Na/K-ATPase inhibitor that may inhibit pump function without activating the kinase signaling function. It inhibits Na/K ATPase pump action with an affinity comparable to ouabain, but does not alter sodium or ATP affinity, is not blocked by potassium, and it does not activate the Src complex or downstream kinases. Other examples of cardiac glycosides that may be used to locally neuromodulate the ANS, related nerves to alter neuronal and/or immune function to treat inflammation and sepsis include acetyldigoxin; G-strophanthin; digoxin; digitoxin; ouabain; ouabagenin; lanatoside C; proscillaridin; bufalin; oleandrin; deslanoside; marinobufagenin and their variants.

SCH-28080 is a potent inhibitor of gastric H+ and K+-ATPase. The novel antiulcer agents, SCH-28080 and SCH-32651 were examined for their ability to inhibit the H+/K+ ATPase enzyme activity in a preparation of microsomal membranes from rabbit fundic mucosa. SCH-28080 inhibited the isolated enzyme activity with a potency similar to omeprazole, IC50s of 2.5 and 4.0 µM respectively. SCH 32651 was less potent exhibiting an IC50 of 200.0 µM. Both compounds may therefore exert their antisecretory activity via a direct inhibition of the parietal cell H+K+ ATPase.

Rabeprazole sodium is gastric proton pump inhibitor. It may suppress the production of acid in the stomach by inhibiting the gastric H+/K+ATPase (hydrogen-potassium adenosine triphosphatase) at the secretory surface of the gastric parietal cell. Rabeprazole sodium has been used clinically to treat acid-reflux disorders (GERD), peptic ulcer disease, H. pylori eradication, and prevent gastrointestinal bleeds associated with NSAID use.

KM91104 is a cell-permeable vacuolar ATPase (V-ATPase) inhibitor that specifically targets the V-ATPase a3-B2 subunits interaction. Bafilomycin A1 is another specific inhibitor of V-ATPase. Both may be used in small volumes to locally neuromodulate the ANS and treat chronic medical conditions.

Na/K, Na/H and Na/Ca blockers: Apamin, a potent Na/K channel blocker, and amiloride and its variants are selective inhibitors of Na/H exchangers may be good candidates for local chemo neuromodulation of the ANS. The sodium-proton (Na/H) exchange is a predominant pathway for sodium to entry into an energy-deficient neuron, especially under ischemia-induced intracellular acidosis. The inhibition of the Na/H pump by amiloride or its derivative ethyl-isopropyl-amiloride may be used to treat ANS dysfunction and treat inflammation.

Cariporide is a selective inhibitor of the Na+/H+ exchanger subtype 1 (NHE-1), also known as the Na+/H+ antiporter. Cariporide has shown to have cardioprotective and antiarrhythmic effects, and has recently been investigated for anticancer activity. Cariporide may be administered locally to treat ANS dysfunction, inflammation and neuromodulation, to restore immune homeostasis.

Zoniporide is a potent and selective inhibitor of Na+/H+ exchanger isoform 1 (NHE-1) with an IC50=59 nM at NHE-1, vs. 12,000 nM for NHE-2. It has been shown to inhibit NHE-1-dependent Na+ uptake with an IC50 of 14 nM and have cardioprotective effects against myocardial injuries and ischemic insults. It inhibits the swelling human platelets and attenuates cardiac contractile dysfunction in rats. Zoniporide may have neurotoxic effects as it causes peripheral sensory axonopathy. Zoniporide may be administered locally to treat ANS dysfunction, inflammation and neuromodulation, to restore immune homeostasis.

KK4389KR is a Na+/H+ exchanger-1 (NHE-1) inhibitor (IC50=0.23 µM) that may treat ANS dysfunction. It may inhibit NHE-1-mediated rabbit platelet swelling. In anesthetized rats, KK4389KR reduced infarct size from 67% (control) to 43% (at 0.1 mg/kg) and 24% (at 1.0 mg/kg); reduced number of ventricular premature beats from 530 to 266 (at 0.1 mg/kg) and 115 (at 1.0 mg/kg); reduced VF incidence from 17 to 8 (0.1 mg/kg) and 0 (1.0 mg/kg); with demonstrated efficacy for research and treatment of myocardial ischemic diseases in animal model. Herein, we present its use to modulate NHE-1 activity on NHE-1 expressing neurons.

CGP-37157 is a specific inhibitor of mitochondrial Na+/Ca2+ exchanger NCLX, as well as sarcoplasmic reticulum calcium-stimulated ATPase and possibly other calcium channels to neuromodulate the ANS. 3',4'-dichlorobenzamil may be used to modulate ANS by inhibiting the Na+/Ca2+ exchanger, Na+ transport and sarcoplasmic reticulum Ca2+ release channels. KB-R7943 (mesylate) is a reverse Na/Ca exchanger inhibitor that can treat ANS disorders.

Na, K, Ca channel blockers: Prilocaine, novocaine, articaine, bupivacaine and lidocaine block sodium channels and are currently used for local nerve block and for spinal anesthesia. These drugs may also be used in conjunction with the above drugs. They may also be mixed with polymers to construct drug formulations where the anesthetic is released over a sustained period of time (days to years) and its effects may last a few weeks to a few years.

Specific methods and formulations are described in the following sections.

Other candidate drugs for local administration and neuromodulation of the ANS to treat inflammation and related medical indications are QX-314 (chloride, a selective sodium channel blocker), glyburide (a potassium channel inhibitor, and has been shown to stimulate insulin secretion), and mibefradil hydrochloride (which is used as a general calcium channel blocker).

Other TRPA, KCNQ and HCN channel blockers: TRPA is a family of transient receptor potential ion channels and TRPA1 is its sole member. It is expressed in the dorsal root ganglia and trigeminal ganglion. A-967079 is a potent inhibitor of TRPA1, which can delivered locally near nerves and ganglia to modulate the ANS.

Humans have over 70 potassium channel genes, but only some are linked to medical conditions. For example, mutations in the KCNQ family of voltage-gated potassium channels (KQT-like, subfamily Q) are associated with cardiac arrhythmias (long QT syndrome 1), deafness and epilepsy. XE 991 is an inhibitor of KCNQ channels, and may be injected locally near nerves or ganglia to treat ANS disorders.

Hyperpolarization-activated cyclic nucleotide-gated (HCN) channels are proteins that serve as non-selective ligand-gated cation channels in the plasma membranes of heart and brain cells. HCN channels are also called pacemaker channels because they help generate within the group of neurons and cardiomyocytes. Zatebradine is a HCN channel blocker that is under investigation for bradycardic activity. It may be delivered locally near neurons and ganglia to modulate autonomic dysfunction.

Voltage-gated channel blockers: Lamotrigine is a voltage-gated sodium channel inhibitor. Oxcarbazepine is an inhibitor of voltage gated sodium channels. Phenytoin blocks voltage gated calcium channels and may be used as an anticonvulsant. Tetrodotoxin, saxitoxin, conotoxin, dendrotoxin, iberiotoxin and heteropodatoxin are naturally occurring or synthetic and block sodium, voltage-gated sodium or potassium channels. These drugs may be used to locally neuromodulate nerves, ganglia, plexi or portion of a nerve to treat chronic medical conditions.

Na/Cl, K/Cl, Na/HCO3 co-transport inhibitors: The Na—K—Cl cotransporter (NKCC) is a protein that aids in the active transport of sodium (Na), potassium (K), and chloride (Cl) ions across the cell membrane. Two isoforms or this membrane transport protein, NKCC1 and NKCC2, are encoded. Bumetanide is an inhibitor of $Na^+/K^+/Cl^-$ cotransporter that may be used to treat ANS-mediated diseases. CLP257 is a selective K+-Cl- co-transporter and KCC2 (Potassium chloride transporter, a neuron-specific membrane protein expressed in the central nervous system) activator that can be used to restore impaired Cl- transport in neurons with reduced KCC2 activity.

Activating the KCC2 transporter is a new mechanism for the treatment of neuropathic pain. Published evidence suggests that CLP257 can modulate plasmalemmal KCC2 protein turnover post-translationally. KCC2 agonists may also be good candidates for local neuromodulation, using methods described above.

Torsemide is a loop diuretic of the pyridine-sulfonylurea class with anti-aldosteronergic properties and inhibitor of the Na+/K+/2Cl- carrier system. It functions in the thick ascending limb of the loop of Henle and enhances the excretion of sodium, chloride and water from the luminal side of the cells. Furthermore, torsemide may treat edematous conditions that are associated with diseases such as liver cirrhosis, kidney disorders and chronic congestive heart failure. Here, this drug can chemically neuromodulate the ANS by locally administering the drug near target organs and tissue (described above) and treat inflammation and sepsis.

VU0240551 is a potent, selective KCC2 inhibitor. KCC2 is a potassium-chloride exchanger expressed specifically in neurons. KCC2 functions to lower intracellular chloride concentrations below the electrochemical potential of the cells, thereby increasing the hyperexcitability of the neurons. KCC2 activity enhances GABA and other inhibitory neurotransmission and is implicated in pain processing. VU0240551 was discovered in a high-throughput screen, followed by directed medicinal chemistry. VU0240551 is selective for KCC2 over NKCC1 (Na—K—Cl cotransporter). It binds competitively to the K+ site and binds noncompetitively to the Cl- site. It is the only small molecule with specificity for a KCC family member. VU0240551 can in some embodiments be used to chemically neuromodulate the ANS locally near select locations inside the body (target organs and tissue described above) and treat inflammation, sepsis and restore immune homeostasis.

Chlorthalidone is a thiazide-like diuretic, an inhibitor of the Na+-Cl- co-transporter. It inhibits Na+ ion transport across the renal tubular epithelium increasing the delivery of Na to the distal renal tubule and indirectly increasing potassium excretion via the Na—K exchange mechanism. Chlorthalidone also promotes Ca++ reabsorption by an unknown mechanism. Recent studies show that chlorthalidone may be a better drug in preventing cardiovascular events than hydrochlorothiazide. It may also be used to modulate GABA-mediated neurotransmission, intracellular chloride concentration, and hypoexcitability or hyperexcitability. Chlorthalidone may also be used to cause neuronal edema and cytolysis by local administration near organs and neuronal tissue (described in previous sections) and treat inflammation and sepsis. S0859 is a selective high-affinity generic inhibitor of the $Na^+/HCO3^-$ sodium bicarbonate co-transporter (NBC). S0859 does not inhibit $Na^+$—$H^+$ exchange (NHE). It may be a strong mediator of ANS when delivered locally near specific neurons and ganglia and a good candidate to chemically neuromodulate target organs and tissue (described above) and treat inflammation and sepsis.

Other drugs: Concanamycin A may be used to inhibit acidification of organelles and perforin-mediated cytotoxicity. Sanguinarine is a benzophenanthridine alkaloid isolated from plants belonging to the family Palaveracea. It exhibits anti-bacterial, anti-fungal, anti-inflammatory and anti-cancer properties. It induces cell cycle arrest and sensitizes cancer cells to apoptosis by activating TNF-related apoptosis inducing ligand. It inhibits STAT3, MMP-2, MMP-9, interacts with glutathione, induces generation of ROS, disrupts the microtubule assembly and causes DNA damage resulting the death of the cancer cells. It has potential to affect nerve cells and may be a modulator of ANS when delivered locally near specific neurons and ganglia and a good candidate to chemically neuromodulate target organs and tissue (described above) and treat inflammation and sepsis.

Stevioside is a noncaloric natural sweetener, 300 times more potent than sucrose. It inhibits transepithelial transport of p-aminohippurate (PAH) by interfering with the organic anion transport system. At 0.5-1 mM, it showed no interaction with any organic anion transporters (OAT). Stevioside reportedly has genotoxic effects in cultured mammalian cells. It may be a strong mediator of ANS when delivered locally near specific neurons and ganglia and a good candidate to chemically neuromodulate target organs and tissue (described above) and treat inflammation and sepsis.

TGN-020 is an inhibitor of Aquaporin 4 (AQP4), the most abundant water channel in brain. Aquaporins (AQPs) are water channels required for maintaining fluid homeostasis and enabling water movement across barrier membranes, but may enhance pathological cellular volume changes and cause edema in injury states.

Pretreatment with the AQP4 inhibitor TGN-020 significantly reduced the volume of brain edema associated with ischemic injury in a mouse model of focal cerebral ischemia. It may be an ANS modulator when delivered locally near specific neurons and ganglia and a good candidate to treat inflammation and sepsis.

Xipamide is a sulfonamide diuretic that blocks sodium reabsorption in the distal tubules of the kidney, resulting in increased urine output. Xiopamide also blocks the cystic fibrosis transmembrane conductance regulator (CFTR) chloride channel. It may delivered locally near neurons, ganglia and nerve plexi to treat autonomic imbalance.

GPCR agonists and antagonists: G-protein coupled receptors (GPCR) comprise a large superfamily of receptors typically sharing a common structural motif of seven transmembrane helical domains. Some GPCRs instead can be single-spanning transmembrane receptors for cytokines such as erythropoietin, epidermal growth factor (EGF), insulin, insulin-like growth factors I and II, transforming growth factor (TGF), or multi-polypeptide receptors such as GPIb-V-LX or the collagen receptor that exhibit outside-in-signaling via G proteins. GPCRs play a vital role in signaling processes that control cellular metabolism, cell growth and filamentation, inflammation, neuronal signaling, and blood coagulation. GPCRs also have an important role as targets for molecules such as hormones, neurotransmitters and physiologically active substances, and act in a manner that controls, regulates or adjusts the function of said GPCRs in a particular molecular and cellular context. For instance, GPCRs include receptors for biogenic amines, e.g., dopamine, epinephrine, histamine, glutamate, acetylcholine, and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and for proteases such as thrombin, trypsin, and factor VIIa/Xa; and for sensory signal mediators, e.g., retinal photopigments and olfactory stimulatory molecules. In short, GPCRs are a major target for the modulation of ganglionic cell activity and ANS.

Unlike fast ligand-gated receptors, GPCRs are not ion channels. GPCR actions take 100 millisecond to minutes. Fast chemical synapses signal in a fraction of a millisecond. They can evoke complex pleiotropic responses typically involving G proteins, second messengers, and numerous intracellular targets. Fast chemical synaptic receptors only change the membrane potential and sometimes admit calcium ions into the cell. The GPCR coupled monoamines and peptides have longer extracellular lifetimes and thus cannot be targeted for point-to-point wiring to a single postsynaptic cell in a circuit. They work on larger groups of cells.

Common GPCR agonists that signal GPCRs located in ganglia are monoamines like, adrenaline, noradrenaline, serotonin, dopamine and histamine; small neurotransmitters like acetylcholine (mAch), gamma aminobutyric acid (GABAB), glutamate (metabotropic, mGluR), ATP (P2Y), adenosine and cannabinoids; peptide neurotransmitters and hormones like opioids, somatostatin, NPY, oxytocin, vasopressin, neurotensins, VIP, galanin, kinins, releasing hormones, and many more; and sensory modalities like light (rhodopsin), odorants, some tastetants including sweet, bitter, and umami.

For most of these GPCR agonists, there are multiple different sensitive GPCRs. In some examples, one agonist may give rise to different intracellular responses depending on the receptor subtypes and splice variants expressed on ganglionic cells. For example, there are nine genes encoding receptors for adrenaline and noradrenaline. Three of them couple to the G-protein $G_q$, often inducing intracellular calcium signaling (α1 adrenergic receptors), three of them couple to $G_i$, often inhibiting adenylyl cyclase activity, activating GIRK channels, or inhibiting calcium channel activity (α2 adrenergic receptors), and three of them couple to $G_s$, often stimulating adenylyl cyclase activity (β adrenergic receptors).

GPCR agonists are typically released at nerve terminals and varicosities, these fast chemical synapses where presynaptic ACh, glutamate, GABA, or glycine release may activate post-synaptic receptors within nanometers of the release site, triggering the opening of ion channels in one post-synaptic neuron within a fraction of a millisecond. Such agonist action stops in a few milliseconds because agonist is quickly removed from the synaptic cleft. GPCR signaling is fundamentally different because GPCR agonists typically have a half-life of 200 milliseconds to several minutes in tissue.

Importantly, agonist spread over such a time period can act on many cells. Thus, GPCR agonist spread beyond a single synapse (called spillover) can have a distal effect. Agonists may thus be used to affect the mode of operation of neural circuits in a paracrine, hormone-like manner rather than providing specific modulatory effects on a single neuronal bundle.

Accordingly, in some embodiments, the GPCR agonist drugs may be administered locally near neurons and ganglia connected to specific organs and upregulate ganglionic activity, control inflammation and restore homeostasis.

Agonist drugs that may be administered locally to target the GPCR on nerve tissue and modulate the ANS include: capsaicin; nicotine; glutamate; medroxyprogesterone acetate; genistein; acetylcholine; carbachol; cytosine; nifene; suxamethonium; epibatidine; varenicline; noradrenaline; amantadine; dextromethorphan; mecamylamine; memantine; methylcaconitine; phenylephrine; methoxamine; cirazoline; xylometazoline; midodrine; metaraminol; chloroethylclonidine; agmatine; dexmedetomidine; medetomidine; romifidine; clonidine; chloroethylclonidine; brimonidine; detomidine; lofexidine; xylazine; tizanidine; guanfacine; amitraz; dobutamine; isoprenaline; noradrenaline; salbutamol; albuterol; bitolterol mesylate; formoterol; isoprenaline; levalbuterol; metaproterenol; salmeterol; terbutaline; ritadrine; L796568; amibegron; solabegron; mirabegron; and others.

In other embodiments, GPCR antagonist drugs may be administered locally to downregulate ganglionic cell activity and affect inflammation to treat sepsis. Antagonist drugs that can be administered near neural tissue to target the GPCR are: NPB112; MAb1; MAb23 monoclonal antibody; Nb6B9 nanobody; acepromazine; alfuzosin; doxazosin; phenoxybenzamine; phentolamine; prazosin; tamsulosin; terazosin; trazodone; amitriptyline; clomipramine; doxepin; trimipramine; hydroxyzine; yohimbine; idazoxan; atipamezole; metoprolol; atenolol; bisprolol; propranolol; timolol; nebivolol; vortioxetine; butoxamine; SR59230A; fasudil; guanfacine; chlonidine; scopolamine; trimethaphan camsylate; guanethidine; galantamine; pentolinium; pancuronium; bupropion; dextromethorphan; diphenidol; ibogaine; hexamethonium; mecamylamine; trimetaphan; conotoxin; bungarotoxin; MDMA; dihydro-beta-erythroidine; and others.

Other examples of drugs that can be administered in a local fashion for the modulation of ganglionic cells via GPCR to control inflammation and treat sepsis are listed in Drug Tables 1-2.

TABLE 1

Non-limiting Examples of Drug candidates for local chemoneuromodulation

| Agonist | FFA1 pEC$_{50}$ | GPR120 pEC$_{50}$ |
|---|---|---|
| EXAMPLE FFAs | | |
| Palmitic Acid (C16:0) | 5.2-5.3 | 4.3 |
| Oleic acid (C18:1) | 4.4-5.7 | 4.5 |
| DHA (C22:6) | 5.4-6.0 | 5.4 |
| PPARγ AGONISTS | | |
| Rosiglitazone | 5.0-5.6* | N.D. |
| FFAR1 AGONISTS | | |
| MEDICA16 | 5.5-5.9* | <5.0 |
| GW9508 | 6.6-7.3 | 5.5 |
| Cpd B | 7.1 | N.D. |
| Cpd C | 6.8 | |
| TUG424 | 7.5[b] | N.D. |
| Cpd 37 | 7.1[b] | |
| TAK-875 | 7.1[c] | N.D. |

TABLE 1-continued

Non-limiting Examples of Drug candidates for local chemoneuromodulation

| Agonist | FFA1 $pEC_{50}$ | GPR120 $pEC_{50}$ |
|---|---|---|
| GPR120 AGONISTS | | |
| Grifolic acid | N.D. | N.D. |
| NCG21 (Cpd 12) | 4.7 | 5.9 |
| Isoindolin-1-one series (Cpd 2) | N.D. | 6.7 |
| Phenyl-isoxazol-3-ol series (Cpd 15) | N.D. | 7.2 |
| Metabolex (Cpd 36) | N.D | >6.0 |

Agonist $pEC_{50}$ values quoted were obtained from fluorescent indicator measurements of $Ca^{2+}$ mobilization, except *Smith et al. (2009) compared TZD agonism for FFA1 ERK activation, while Kotarsky et al. (2003) measured FFA1 $Ca^{2+}$ signaling using an aequorin reporter gene, *measurement of insulin secretion/DMR assay; *measurement of inositol phosphate accumulation.
N.D.—not determined;
$pEC_{50}$ values have not been published.

TABLE 2

Non-limiting Examples of Drug candidates for local chemoneuromodulation

| Receptor Target | Antibody | Company | Disease Indication | Status |
|---|---|---|---|---|
| CCR4 | KW-0761/AMG 761/ Mogamullzumab | Kyowa Hakko Kirin | Cancer (adult T-cell leukaemia) CTCL Peripheral T and NK-cell lymphoma | Approved in JP (Kyowa) Phase 3 Phase 2 Phase 2 |
| | AT008 | Amgen | PTCL | Phase 1/2 (Amgen) |
| | | Affitech | Allergy Cancer | Preclinical |
| CCR5 | PR0140 | CytoOyn | Human Immunodeficiency Virus | Phase 2 completed |
| | HGS 1025 | Human Genome Sciences/GSK | Ulcerative colitis | Discontinued (Phase 1 b) |
| | HGS004 | Human Genome | HIV | Phase 1 completed |
| | | | HIV | Preclinical |
| | HGS 101 | Sciences/GSK | HIV | Discovery |
| | (CCR5-2320) | Human Genome Sciences/GSK | Undisclosed | Discontinued (Discovery) |
| | Tetravalent bispecific | Crystal Bioscience | HIV | Preclinical |
| | MLN1202 | Pepscan | | |
| CCR2 | | Roche | Bone metastasis | Phase 2 completed |
| | NN-8209 | | RA and MS | Discovery |
| C5aR | NN-8210 (black-up) | Takeda-Millennium/South-West Oncology Group MRCT/Unlv Regensberg G2 Therapies/Novo Nordisk | RA SLE | Phase 2 completed Phase 1 terminated |
| CGRP-R | AMG-334 | Amgen | Migraine (prophylaxis) Hot flushes/menopause | Phase 2 Phase 1 |
| CXCR4 | MOX-1338 (BMS936564) | Medarex/Bristol-Myers Squibb | B cell cancers (AML, CML. LBCL, FL) | Phase 1 Discontinued (Phase 1) |
| | ALX-0651 (nanobody) | Ab lynx | Stem cell mobilization | Discontinued (Phase 1) |
| | LY-2624587 | Eli Lilly | Cancer | Preclinical |
| | AT009 | Affitech | Cancer | Preclinical |
| | 515H7 | Pierre Fabre | Cancer/HIV | Preclinical |
| GCG-R | CX-02 & CX-05 | Northwest Biotherapeutics | Cancer | Discontinued (Phase 1) |
| | AMG477 | Amgen | Type 2 diabetes | NORR (Discovery) |
| CXCR5 | | Pepscan | Undisclosed | Phase 1 |
| | SAR113244 | Sanofi | RA/SLE | |
| CCR9 | | Takeda-Miliennium | Inflammation (Crohn's disease) | Discontinued (preclinical) |
| VPAC-1 | | Thromhogenics | Thrombocytopenla | Discontinued (preclinical) |
| FPRL | | Yes Biotech (Anogen) | Alzheimer's Disease | NORR (preclinical) |
| BK2 | DM-204 | DiaMedica | Type 2 diabetes | Preclinical |
| CCR6 | | G2Therapies | Inflammation | Preclinical |
| S1P3 | 7H9 | Expression Drug Designs | Cancer | Preclinical |
| CXCR2 | | Crystal Bioscience | Cancer | Discovers |
| | | MorphoSys | Cancer | Discovery |
| 82AR | | Crystal Bioscience | Respirators | Discovery |
| PAR1 | | Crystal Bioscience | Cancer | Discovery |
| CXCR3 | AT0010 | Affltech | Inflammation | Discovery |
| S1P-R | | Pepscan | Undisclosed | NDRR (Discovery) |
| CCR7 | | Pepscan | Cancer, immunological disorders | Discovery |
| CXCR7 | | Pepscan | Cancer | Discovery |
| GLP-IR | | Abbott/HGS | Type 1 or 2 diabetes Neurological/metabolic | NDRR (early stage) |

TABLE 2-continued

Non-limiting Examples of Drug candidates for local chemoneuromodulation

| Receptor Target | Antibody | Company | Disease Indication | Status |
|---|---|---|---|---|
| CCR8 | | ICOS/Ell Lilly | Inflammation | Early stage (patent) |
| C3aR | | Human Genome Sciences | Asthma | Early stage (patent) |
| PAR2 | | Boehringer Ingelheim | Inflammation (1805) | Early stage (publication) |
| | | Amgen | | Early stage (patent) |
| LGR5 | | Kyowa Hakko Kirin | Cancer | Early stage (publication) |
| CRTH2 | | Sosei/Abgenix | Inflammation | NDRR |

Drug formulation dose, concentration and volume used for the local chemo neuromodulation of ganglionic cells, nerves, portions of nerves, plexi or ganglionated plexi by the antagonism of ion channels and ion pumps may vary based on drug half-life, proximity of target ganglia (and other neuronal sites of interest) from the site of administration, pharmacodynamics and pharmacokinetics. In general, the total dose of the antagonist drug administered to a patient to modulate the ganglia and other target neuronal sites is between 0.1 nanograms and 15 milligrams. In other embodiments, the more preferred total doses of the ion- and pump-antagonist drugs are in the range of 10 nanograms and 30 micrograms. If incorporated in a drug delivery system that permits sustained release, 10 micrograms to 1 gram of the agent may be loaded into the drug delivery system at a loading level of between 10 and 80%, more preferably 30 to 60%, allowing for delivery for a period of hours to months, more preferably one to two weeks.

Different drug formulations and doses may be delivered near different target nerves based on their size, morphology, structure and function. In general, higher drug doses may be delivered locally to generate prolonged ganglionic cell-block or neurotoxicity. Specifically, higher doses may be needed to achieve the desired distribution of the drug to affect cell soma and modulate the ganglia. The total dose of ion-channel or ion-pump antagonist drug delivered to a local tissue for ganglionic cytotoxicity can be between 0.001 and 15 milligram dose. A smaller volume of drug and a different or diluted concentration may be desirable to modulate individual nerve fibers. Doses used for modulation of ganglionic cells to control inflammation by agonism or antagonism of GPCRs may vary based on drug half-life, proximity of target ganglia from the site of administration (ganglia, plexus, nerve, axon, ganglionated plexus or fat pads), pharmacodynamics and pharmacokinetics. In general, the total dose of GPCR agonist drugs may be lower than the total dose of GPCR antagonist drug. Additionally, the total dose of drug targeting GPCR in a manner to induce neuronal toxicity may be higher than the total dose of GPCR-targeted drug to stimulate or downregulate neuronal activity. The total dose of GPCR drug administered to a patient to modulate the autonomic ganglia may be between 0.1 nanograms and 30 milligrams. In other embodiments, the total dose of GPCR agonist or antagonist drug administered may be between 10 nanograms and 1 microgram.

In other embodiments, higher doses may be delivered locally, to achieve prolonged ganglionic cell block or cell death in order to control inflammation. In these cases, the total dose of GPCR-targeted drug administered locally may be between 0.01 and 30 mg. Yet in other embodiments, lower doses may be delivered locally by mixing the drug with a polymer and releasing the drug over a sustained period of time ranging between a few weeks to few months or a few years, as described below.

In other embodiments, different formulations may be delivered to different organ tissue target sites inside the body. For example GPCR antagonist-based formulations may be delivered to the sympathetic ganglia regulating the SNS, and GPCR agonist-based formulations may be delivered near the vagus system. Or in other embodiments, channel blockers may be delivered to the sympathetic chain ganglia and GPCR based formulations may be delivered to the specific nerve fibers innervating the organs.

Other drug classes: Chemotherapeutic agents like doxorubicin, anthracyclines, paclitaxel, taxol and cisplatin may be injected locally near nerves and ganglia to neuromodulate and affect nerve function, organ function and treat inflammation, sepsis and related medical conditions. Injection of demyelinating agents (like lipocalin-2) and angiogenesis inhibitors (that specifically targets proliferating endothelial cells, like, vasostatin) may also be used for local neuromodulation to treat inflammation and sepsis.

Drug Combinations

The described formulations may contain one or more drugs and other constituents for specific functions beyond excipients and buffers used in pharmaceuticals to achieve the desired pH level, viscosity, and solubility. These include compounds to improve the visibility of the drug formulation during delivery to the target tissue under different imaging conditions; anesthetics to reduce local pain associated with nerve block and nerve damage during the procedure. Currently, in pain blockade, a combination of local anesthetic, epinephrine, a steroid and an opioid is often used to achieve temporary nerve block. Epinephrine constricts blood vessels to slow the diffusion rate of the anesthetic, the steroid is used to reduce inflammation surrounding the overactive ganglionic cells and the opioids block the pain. These embodiments may be included into the drug formulation as an injectable for local injection or into a polymer. Specific compounds and polymers are described in detail in the following sections.

In addition, two or more drugs may be used in combinatorial form to develop a therapeutically efficacious drug formulation for local neuromodulation using individual drug component dose levels that are safe and significantly below their individual local dose or concentration levels required for neuromodulation. This mitigates the risk for toxicity associated with potentially higher dose needed for local therapeutic neuromodulation. In one embodiment, patients may be pretreated with precursor agents, either systemically or locally, to prepare the nerve, ganglion or tissue for neuromodulation. Pretreatment of the nerve with a precursor drug formulation facilitates the local injection of a lower drug dose (volume or concentration) locally, to achieve prolonged nerve block, neuro-immune signaling, ganglionic cell block or cell death. This allows for the selective use of drugs and concentrations that are below their systemic toxicity levels, yet be efficacious to locally neuromodulate and treat inflammation, sepsis and related medical conditions. One example of such combinatorial treatment is to pretreat patients with parasympathomimetic and b-adrenolytic agents that diminish the toxicity of cardiac glycosides.

Specifically, diazepam could be administered as a precursor agent before local neuromodulation of nerves and ganglia using cardiac glycosides and other ion channel blockers.

Combination Therapies

Methods and formulations described here may be used to treat patients in combination with currently available treatments for inflammation and sepsis. These include and are not limited to administration of antibiotics, fluids, crystalloid solutions, vasopressors (e.g., vasopressin, dopamine, norepinephrine, neosynephrine, etc.), corticosteroid replacement therapy, volume resuscitation, respiratory (oxygen) support, circulatory support, metabolic and nutritional support.

Methods and formulations described here may be used to treat patients in combination with new therapies currently in development to treat inflammation and sepsis. These include and are not limited to vagus nerve stimulation (VNS), splenic nerve (or stimulation of other nerves disclosed herein) stimulation (electrical or otherwise), ultrasound energy treatment, and use of membrane filters.

Drug Formulations

One or more of the active pharmaceutical ingredient (API) or bioactive molecule(s described above is/are present in a therapeutically effective amount, e.g., an amount sufficient when administered locally to treat a disease or medical condition mediated thereby. The compositions may also include various other agents to enhance delivery, safety, efficacy, and stability of the active ingredients.

In some therapeutic strategies for sepsis, a drug having an affinity for an ion pump or ion channel or a G-protein coupled receptor (GPCR) may be administered to an organ comprising lymphoid tissue, near a point of innervation. Suitable drugs for the treatment of sepsis in a patient include: members of the cardiac glycosides, such as digoxin, digitoxin, ouabain, proscillaridin, bufalin, digitoxigenin, digoxigenin, marinobufagenin, and their derivatives; ion channel blockers, such as amlodipine, diltiazem, felodipine, isradipine, nicardipine, nifedipine, nisoldipine, verapamil, quinidine, ajmaline, procainamide, dispyramide, phenytoin, mexiletine, moricizine, propafenone, carvedilol, propranolol, esmolol, timolol, metoprolol, atenolol, bisoprolol, dronedarone, ibutilide, sotalol and their derivatives; members of the G-protein coupled receptor agonists and antagonists, such as 2-thiazoleethanamine, betahistine, demethylbetahistine, betazole, dimaprit, imetit, amthamine, impromidine, SKF91488, azelastine, cetirizine, chlorpheniramine, dimetindene, diphenhydramine, doxepin, doxylamine, ebastine, embramine, fexofenadine, levocetirizine, loratadine, meclizine, pheniramine, promethazine, quetiapine, burimamide, cimetidine, lafutidine, nizatidine, For example, the drug compositions may also include, depending on the formulation desired, pharmaceutically-acceptable, non-toxic carriers such as polyethylene glycol (PEG) or diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate-buffered saline (PBS), Ringer's solution, dextrose solution, and Hank's solution. In addition, the pharmaceutical composition or formulation may include other carriers, adjuvants, or non-toxic, nontherapeutic, non-immunogenic stabilizers, excipients and the like. The compositions may also include additional substances to approximate physiological conditions, such as pH adjusting and buffering agents, toxicity adjusting agents, wetting agents and detergents. The composition may also include any of a variety of stabilizing agents, such as an antioxidant.

The pharmaceutical compositions may be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50/o of the population). The dose ratio between toxic and therapeutic effects is the therapeutic index and it can be expressed as the ratio LD50/ED50. Compounds that exhibit large therapeutic indices can be preferred.

The data obtained from cell culture and/or animal studies may be used in formulating a range of dosages for humans. The dosage of the active ingredient typically lies within a range of circulating concentrations that include the ED50 with little or no toxicity. The dosage may vary within this range depending upon the dosage form employed and the route of administration utilized.

To achieve local drug administration, a parenteral liquid formulation may be generated by reconstituting lyophilized drug with solubilizer. Reconstituted drug and its formulation can be packaged in a vial, ampule or prefilled syringe. Said liquid can be a solution, emulsion or suspension. To generate said formulation, an effective amount of neuromodulatory drug may be formulated in the presence of solubilizer, stabilizer, buffer, tonicity modifier, bulking agent, viscosity modifier, surfactant, chelating agent and adjuvant.

In a preferred embodiment, the drug may be formulated with a hydrophobic moiety. A hydrophobic moiety is either a lipid moiety or an amino acid. Equally preferably, the hydrophobic moiety may be selected from the group comprising: phospholipids, steroids, sphingosines, ceramides, octyl-glycine, 2-cyclohexylalanine, benzolylphenylalanine, propionoyl ($C_3$); butanoyl; pentanoyl ($C_5$); caproyl ($C_6$); heptanoyl ($C_7$); capryloyl ($C_8$); nonanoyl ($C_g$); capryl ($C_{10}$); undecanoyl ($C_{11}$); lauroyl ($C_{12}$); tridecanoyl ($C_{13}$); myristoyl; pentadecanoyl ($C_{15}$); palmitoyl ($C_{16}$); phtanoyl (($CH_3$)$_4$); heptadecanoyl ($C_{17}$); stearoyl ($C_{18}$); nonadecanoyl ($C\hat{\ }$); arachidoyl ($C_{20}$); heniecosanoyl ($C_{21}$); behenoyl ($C_{22}$); tracisanoyl ($C_{23}$); lignoceroyl ($C_2$); alcohols; glycerol; polyethylene glycol; dimethylsulfoxide; mineral oil, and cholesterol; wherein said hydrophobic moiety is formulated in the presence of drug.

In another preferred embodiment, the drug may be formulated with a salt. In yet another embodiment, the drug may be formulated in the presence of an ion. For example, anions of chloride; fluoride; or bromide may be used. Additionally, cations of calcium; potassium; sodium; or zinc may be used.

In yet another embodiment, the drug composition may include a non-therapeutic compound (contrast agent) to assist with the visualization of the drug injection to the target nerve tissue under different body imaging conditions. Specific contrast agents that may be mixed into the drug formulation for visibility under x-ray, electron-beam CT, external and intravascular ultrasound and MRI and described elsewhere herein.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are preferably sterile. To the extent that a given compound must be synthesized prior to use, the resulting product is preferably substantially free of any potentially toxic agents, such as any endotoxins, which may be present during the synthesis or purification process. Compositions for parental administration are also preferably sterile, substantially isotonic and made under GMP conditions.

Sustained-Release Formulations

The above drugs and drug formulations may also be incorporated into a polymeric or lipid matrix to release the drug over a period of time, ranging between a few weeks to a few months/years, and affect the nerves and immune function. The polymers may be biostable or biodegradable and constitute biocompatible matrices for sustained or controlled drug delivery. Using different delivery methods and devices, different composite hydrogel-based drug formulations, gels, plugs, microimplants, nanorods, nanoparticles and microspheres containing the therapeutic drug molecules may be administered near the specific nerve target sites, ganglia, nerve fibers, spleen, and immune cells to treat disease by local chemical neuromodulation.

In one embodiment, the system is designed to provide on/off pulsatile release of drugs to mimic the vagal neurostimulation platforms that have shown promise in preclinical and clinical studies. In one embodiment, a solid microimplant comprised of layers of multiple alternating coatings with drug loaded and drug-free layers allow for release of the drug, for example for 10 minutes to 6 hours, more preferably one hour, followed by an 'off-period' during which no drug is delivered to the site. In this manner, a bolus or sustained release of drug can be provided intermittently. For example, 1 microgram to 60 micrograms can be delivered over 10 minutes to 6 hours, at a rate of 1 to approximately 10 micrograms per hour. The microimplant is designed as a surface eroding implant in which the advancing front of hydrolysis of the biodegradable polymer (e.g. polyanhydride-based polymers) permits diffusion of the drug from the implant. Alternatively, pulsatile release can be achieved through progressive swelling of the microimplant as a water front permits solubilization and release of the drug or with a non-swelling microimplant.

In some embodiments, the system provides sustained release of drug for a period of one day to 6 months, e.g., one week to two weeks. As sepsis is an emergent and acute condition that a patient typically either survives and recovers or rapidly deteriorates, a drug delivery system supporting the immune system could deliver drug until the patient recovers and then be cleared from the body. In this manner, continued modulation of the splenic nerve, spleen, immune cells could be avoided beyond the treatment and recovery from the condition itself. Preferably, biodegradable or bioerodible drug delivery systems should be employed to provide sustained or controlled drug delivery to the target tissue and then be cleared from the system and allow the body to return to normal or baseline physiologic neuroimmune modulation.

In some preferred embodiments, formulations than can be injected in a low-viscosity state through a higher gauge needle that then provide for sustained release of drug are desirable. Typically, this is achieved through a passive or active state change in which the viscosity of the formulation changes to permit sustained release of drugs. These drug delivery systems are known in the art and may take the form of shear-thinning polymers, such as hyaluronic acid, in situ crosslinking or polymerizing systems, such as those with polyethylene backbones or other configurations (e.g. star-shaped). To the inventors' knowledge, these systems have not been developed before to deliver immunomodulatory agents to the spleen or neuromodulatory agents to the splenic nerve(s). In some embodiments, the therapeutic agents could be as described or modified for use with those described in U.S. Pub. No. 2016/0317621 A1 to Bright, which is hereby incorporated by reference in its entirety.

The bioactive agent or therapeutic drug molecule can be trapped in a polymeric network of hydrophobic regions which prevent the loss of the drug. In some cases, the composite material has two phases, where both phases are absorbable, but are not miscible. The continuous phase may be a hydrophilic network (such as a hydrogel, which may or may not be crosslinked) and the dispersed phase be hydrophobic (such as an oil, fat, fatty acid, wax or fluorocarbon, or other synthetic or water immiscible phase). In some cases, especially water soluble drugs, a release rate modifying agent may also be used to incorporate the drug and control its release profile. Examples of macromers, polymers, cross-linkable groups, hydrophilic components and hydrophobic components and rate-releasing modifying agents are described below.

In a preferred embodiment, biodegradable macromers are provided in an acceptable carrier and crosslinking, covalently or non-covalently, to form hydrogels which are thermoresponsive. The drug formulations described above (biologically active drugs) may be incorporated in the macromer solution or in the resulting hydrogel after crosslinking. The hydrogel formulations can be optimized are optimized for volume and drug release rate, which are temperature dependent. The hydrogels may be formed in situ, for example, at a tissue site, and may be used for controlled release of drugs near nerve tissue. The macromers used to form the hydrogels may also be optimized for selective properties including hydrophobicity, hydrophilicity, thermosensitivity or biodegradability, and combinations thereof. The gels permit controlled drug delivery and release the drug or biologically active agent in a predictable and controlled manner locally at the targeted nerve site.

The macromers preferably include cross-linkable groups which form covalent bonds with other compounds, while in aqueous solution. This allows crosslinking of the macromers to form a gel, either after, or independently from thermally dependent gellation of the macromer. Chemically or ionically crosslinkable groups known in the art may be provided in the macromers. Polymerization chemistries may include, for example, reaction of amines or alcohols with isocyanate or isothiocyanate, or of amines or thiols with aldehydes, epoxides, oxiranes, or cyclic imines; where either the amine or thiol, or the other reactant, or both, may be covalently attached to a macromer. Mixtures of covalent polymerization system, sulfonic acid or carboxylic acid groups may be used.

The macromers may include hydrophobic domains and the hydrophobicity of the gel may be tailored to achieve the desired drug-release profile. The cell membrane is composed of a lipid bilayer with the inner region being hydrophobic. A hydrophobic tail may be incorporated into the macromer so that the biologically active drug molecule can diffuse into the lipid bilayer. Examples of tail groups are fatty acids, diacylglycerols; molecules from membranes such as phosphatidylserine, and polycyclic hydrocarbons and derivatives, such as cholesterol, cholic acid, steroids and the like. In addition, more than one hydrophobic group can be incorporated into the macromer to improve adherence of the hydrogel to the target tissue, the neuron. Examples of hydrophobic groups include oligomers of hydroxy acids such as lactic acid or glycolic acid, or oligomers of caprolactone, amino acids, anhydrides, orthoesters, phosphazenes, phosphates, polyhydroxy acids or copolymers of these subunits. Also, the hydrophobic regions may be formed of poly(propylene oxide), poly (butylene oxide), or a hydrophobic non-block mixed poly (alkylene oxide) or copolymers thereof. Poly L-lactide, or poly D,L-lactide or polyester, which is a copolymer of poly(lactic-co glycolic) acid (PLGA), may also be used.

The biodegradable macromers may also include hydrophilic regions by incorporating water-soluble hydrophilic oligomers available in the art. They may include polymer blocks of poly(ethylene glycol), poly(ethylene oxide), poly (vinyl alcohol), poly(vinylpyrrolidone), poly(ethyloxaZoline), or polysaccharides or carbohydrates such as hyaluronic acid, dextran, heparan sulfate, chondroitin sulfate, heparin, or alginate, or proteins such as gelatin, collagen, albumin, ovalbumin, or polyamino acids.

The biodegradable polymers incorporated into the formulation are preferably hydrolyzable under in vivo conditions. Hydrolyzable groups of interest include polymers and oligomers of glycolide, lactide, epsilon-caprolactone, and other hydroxy acids. Preferred poly(alpha-hydroxy acids) are poly (glycolic acid), poly(DL-lactic acid) and poly(L-lactic acid). Other materials include poly (amino acids), polycarbonates, poly(anhydrides), poly (orthoesters), poly(phosphazines) and poly(phosphoesters). Polylactones such as poly(epsilon-caprolactone), poly(delta caprolactone), poly(delta-valero-lactone) and poly(gamma butyrolactone). Monomeric, dimeric, trimeric, oligomeric, and polymeric regions may be used to yield a target polymer-drug formulation that is substantially water soluble.

Release rate modifying agents may also be incorporated into the drug-polymer formulations to control drug release. Hydrophobic agents are able to form a relatively stable dispersed phase within the continuous hydrogel matrix and may be used as a secondary container for substantially water soluble therapeutic drugs. Degradation times and drug release profiles may be tailored by selecting appropriate polymers or monomers using linkages susceptible to biodegradation, such as ester, peptide, anhydride, orthoester, phosphazine, and phosphoester bonds. Crystallinity and molecular weight can also significantly alter degradation rates.

Release Rate.

The release of the drug may be diffusion controlled, chemically or biodegradably controlled, solubility controlled (of the drug), solvent controlled (swelling, osmosis, rupture), or externally activated/modulated (e.g. magnetic system in which micromovement of magnetic beads within a hydrogel causes movement and thus drug release, low frequency ultrasound, electroporation), controlled by the extent of crosslinking and crystallinity, the size, thickness or volume of the drug delivery system, the porosity, and the solubility of the system (e.g. plasticizers or the additional of hydrophilic agents (e.g. glucose, mannitol)) that are rapidly dissolved and create a network or pathway for dissolution of the drug out of the system, or controlled by the degradation of the hydrogel scaffold. The release rate of the drug may also be controlled by the pH, ionic strength, temperature, magnetic field, ultrasound, or electrical stimulation. Preferably, the release of the agent is not controlled by the degradation of the polymer. The release rate may be monomodal, bimodal or polymodal. The release rate may include a burst phase and then a linear continuous sustained release phase. The solubility of the drug in the aqueous phase drives the rate of drug release with poorly water soluble drugs providing longer release than the higher solubility drugs.

The hydrogel matrix preferably also includes a biologically active agent, either singly or in combination with different agents. Examples of therapeutic or bioactive agents are described in previous sections.

Expanding or Filling the Potential Space.

In some embodiments, it can be desirable to deliver an agent, such as a hydrogel, to fill the entire space within the folds or outer layers of a ligament associated with the spleen, for example. Delivering the solution in a suitably viscous formulation, such as a hydrogel, slurry, an injectable foam, a glue or an in situ forming injectable scaffold, including a hydrogel, slurry or other gel that can fill the majority of, or substantially the entire location to be treated. Some examples of slurries that can be used with embodiments disclosed herein can be found, for example, in U.S. Pat. No. 7,057,019 to Pathak, which is hereby incorporated by reference in its entirety. In one embodiment, the therapy is a viscous solution or gel that can be injected with a minimally invasive technique to fill an anatomical space and adheres to the edges of the tissue.

Porosity.

Controlling the pore size of the gel provides another mechanism to control the release of drugs, particularly low molecular weight drugs, as well as to prevent cellular infiltration or axonal regeneration within or across the hydrogel. In some embodiments, the gels can have a pore size of less than 50 µm, 20 µm, 10 µm, or even less. These gels can be non-porous or minimally porous for a period of time (e.g., 2-3 months) until the polymer beings to degrade. In some embodiments, the pores are too small for Schwann or immune cell ingrowth (e.g., less than 8 µm), and the density of pores is not such that a network is formed between the pores. In one embodiment, the use of low MW polymer chains between crosslinks reduces the chain flexibility, reduces mesh size/pore size, and convers an advantage to delay the release of drugs out of the gel. In one embodiment, small pores (<8 µm) assist with the echogenicity of the hydrogel but are smaller than infiltrative cells such as Schwann cells, other supporting cells, immune cells and axons. In still another embodiment, the pores are microporous (e.g., from about 100-500 Angstroms). Some examples of hydrogels with pores can be found, for example, in U.S. Pat. No. 8,399,443 to Seward, which is hereby incorporated by reference in its entirety.

In one embodiment, polymers with small pore or mesh sizes act as the rate-limiting factor in diffusion of drug out of the hydrogel. By controlling the pore size to less than 5 microns, or more preferably less than 1 micron, for example, a small molecule may diffuse out of the scaffold but cells such as axons, glia and inflammatory cells cannot enter the scaffold. Pore size can be varied with the degree of crosslinking and the molecular weight of the crosslinks of the gel.

In another embodiment, the pore size of the hydrogel can be controlled to pores less than about 50 microns, 20 microns, or 10 microns.

Bioadhesive.

The hydrogel can be designed, in some cases, to covalently or noncovalently, ionically or nonionically, adhere to the adjacent tissue. In one embodiment, it adheres directly to the nerves that it is surrounding through crosslinking with neural tissue. In one embodiment, cationic interactions improve the adhesion of a hydrogel to the tissue. Systems that maintain a stable position and adhere to the site at which they were delivered for several months and do run the risk of migrating or compressing adjacent structures such as the lung or spinal cord can be desirable.

Echogenicity.

In one embodiment, the hydrogel is naturally echogenic, such that its injection and spread is visible under ultrasound guidance. In another embodiment, an agent or microbubbles or some either echogenic component is added to the hydrogel to improve its echogenicity. In some embodiments, the combination of the neuromodulatory agent and the hydrogel improves the echogenicity and/or allows the hydrogel to be visualized under color Doppler.

Flexibility.

In some embodiments, the gel can be flexible and compliant given its close approximation to the appropriate anatomy.

Swelling.

In some embodiments, the drug delivery systems undergo less than about 10%, 5%, or substantially no swelling at all when placed in situ for safety reasons.

A bioerodible drug delivery system that can control the spread of a low-molecular weight neuromodulatory drug over a period of days or months, that has the appropriate rheological and mechanical characteristics to permit the hydrogel spread within the target location and reduce the off-target spread, provide a non-permissive substrate and/or functions as a tissue sealant can be desirable in some embodiments.

In Situ Forming Gels.

Of interest in some cases are in situ crosslinking synthetic polymers. In situ forming materials can be advantageous because they can be injected through a fine gauge needle as a liquid to the target zone and then form a solid scaffold in viva that matches the contours of the potential space. In situ forming gels may transition from a solution to a gel as a result of pH, temperature, salt, light, biomolecules, solvent-exchange, UV-irradiation, ionic crosslinking, covalent crosslinking, electromagnetic field. Different types of crosslinking are described in U.S. Pub. No. 2014/0363382 A1 to Campbell et al., which is hereby incorporated by reference in its entirety.

Cross-Linked.

For cross-linked gels, in which two precursor solutions are typically mixed containing functional groups that react with each other to form a crosslinked gel, by varying the ratio of the precursor solutions, the concentration of an accelerator or crosslinking agent, the rate at which the two solutions form a solid hydrogel can be varied. Upon mixing the two precursors (low viscosity solutions approximating that of water), but before the formation of the solidified hydrogel, an 'intermediate' state of the gel in which the viscosity is between that of the precursor solution and the solidified hydrogel forms and can be injected into the desired anatomical location.

Crosslinked PEG.

In one embodiment, a hydrogel such as one from the group of in situ polymerizing poly(ethylene glycol)-based hydrogels is selected for the delivery of drugs. Crosslinked PEG-based polymers are biocompatible, have controlled crosslinking, degradation, flexibility, and relatively high adhesion strength. In particular the use of multi-arm PEGs, such as 4-armed PEG that are functionalized to cross-link with one another can be of interest. Additional spacers can be added between the 4-armed PEGs to vary the mechanical and drug delivery properties (if desired) of the polymer. The molecular weights of the PEG arms, on average, may be between about 200 Da to 20 kDa, preferably between about 1 kDa and 8 kDa, more preferably between about 2 kDa and 5 KDa in some embodiments. The molecular weight of the PEG precursor can be, in some embodiments, between about 4 KDa and 100 kDa, more preferably between about 8 kDa and 10 kDa or 20 kDa and 35 kDa. Generally, about 4 to 30% w/w concentration of precursors are used to prepare gels in some embodiments.

The precursors may be a combination of an ester group on one PEG (precursor A) and a trilysine amine (precursor B). In some embodiments, the precursor A is a 20 kDa N-hydroxysuccinimide end capped PEG which is resuspended at the time of delivery in sodium phosphate buffer, the accelerator. The precursor B can be, in some cases, a trilysine acetate in a 0.075 M sodium borate decahydrate buffer (pH 10.2). A preservative may be added, for example butylated hydroxytoluene (BHT). In another embodiment, the PEG precursor is a higher molecular weight 31.5 kDa N-hydroxysuccinimide end capped PEG, with the same buffer and trilysine acetate buffer, which together form a gel in about 10 seconds. In this embodiment, the PEG precursor (lyophilized) is mixed with a diluent (e.g., the trilysine acetate buffer) in a dedicated syringe. The accelerator, the sodium phosphate buffer remains in a separate syringe.

These hydrogels can remain at the desired anatomical location for, e.g., between 2 to 3 months and then erode through hydrolysis, are resorbed, and fully cleared through renal filtration within, e.g., approximately 4 to 6 months. These in situ, polymerizing hydrogels have been commercially developed as an absorbable perirectal spacer (SpaceOAR), and as a dural sealant (DuraSeal, Covidien). In addition to these technologies, other types of major hemostats, sealants and adhesives described by Mehdizadeh and Yang, Macromol. Biosci. (March 2013) are incorporated by reference in its entirety. By varying the ratio of the precursors, the in situ gelation time can be varied. Newer PEG hydrogel formulations have less swelling, which can be an advantageous characteristic in a formulation delivered to certain anatomical locations.

In one embodiment, a 4 arm PEG amine (—NH2) and a 4 arm PEG NHS ester are mixed in the presence of HCl. The molecular weights and ratios of the two PEGs can be varied to control the properties of the polymer. In one embodiment, after the precursors are mixed, the sol to gel transition can be quick (2-13 seconds) or prolonged (1-2 minutes), to allow the gel time to migrate before removing the delivery system. In some embodiments, the liquid forms a gel in about 2 seconds, 10 seconds, 20 seconds, 120 seconds, or 240 seconds.

In another embodiment, hyaluronic acid is added to the precursor formulation to increase the viscosity of the solution in order that it can travel within, for example, a splenic ligament, and then gelling after that. For example, the PEG/HA mixture can be delivered at a first location and the agent flows out of the needle/catheter both rostrally and caudally. The ultrasound probe is advanced rostrally with the flow of the agent and when it reaches the lower border of the desired location, the flow of material is halted. In another embodiment, when the materials reach the middle of the border of the desired location, the flow of material is halted. In some cases, when the material reaches the superior or most rostral border of the desired location, the flow is halted and the caudal spread of the agent is noted prior to removal of the needle. In one embodiment, HA is crosslinked with bifunctionalized maleimide-PEG-maleimide polymer using enzymatic crosslinking and then crosslinked with a DA click chemistry reaction to have outstanding shape memory and anti-fatigue properties.

In yet another embodiment, the crosslinked PEGs can be mixed with low molecular weight PEG, such as PEGs with a molecular weight less than 3.35 kDa, including 200 Da, 400 Da, 1 kDa, or 2 kDa linear PEGs. These PEGs can assist in modulating the release of drugs from the polymer.

These crosslinked PEGs can be delivered through needles, such as for example 17G or 18 G needles or with needles as high as 33G, or about 27G, giving them flexibility in terms of routes of administration (catheter-based or needle-based).

Other technologies that may be adapted for use with systems and methods as disclosed herein include the Focal Seal product, which forms in situ through photochemical/chemical polymerization of acrylate-capped PEG-PLL and poly(trimethylene carbonate), or CoSeal, is a covalently crosslinked PEG product comprised of two 4-arm PEGs with glutaryl-succinimidyl ester and thiol terminal groups.

PEG Generally.

PEG-based hydrogels are biocompatible, have controlled degradation, flexibility, and relatively high adhesion strength, particularly when crosslinked. Through careful selection of the molecular weight, the number of arms, and the reaction conditions, other in situ forming PEG hydrogels can be synthesized. The drug delivery systems may be comprised of functionalized linear PEG or multi-arm PEG derivatives (with reactive groups) such as those available from JenKem Technology or Nanocs. These functionalized systems may be crosslinked with one another through a covalent interaction. PEG may be functionalized with an amine group (or other acid reactive chemical group) that binds to a carboxylic group (or other amine reactive group). These include 3 arm PEG amine (—NH2), 4 arm PEG amine (—NH2), 4 arm PEG carboxyl(—COOH), 4 arm PEG SCM (4 arm PEG NHS ester), 4 arm PEG Succinimidyl glutaramide (-SGA) with a longer half-life than the —SCM) 4 arm PEG Nitrophenyl carbonate (—NPC) with a carbonate linker between the PEG and NHS ester in which the release of p-nitrophenol can be traced by UV spectroscopy, 4 arm PEG succinimidyl carbonate (—SC) with a carbonate linker and a longer half-life than —SCM, 4 arm PEG Maleimide (-MAL) which is selective for thiol groups and reacts at pH 5-6.5, 4 arm PEG Acrylate (-ACLT) for use in vinyl polymerization or co-polymerization, 4 arm PEG Thiol (—SH), 4 arm PEG Vinylsulfone (—VS) which binds to free thiol groups in aqueous buffer between 6.5 and 8.5 pH at room temperature, 4 arm PEG Succinimidyl Succinate (—SS) with a cleavable ester linker to make it a biodegradable hydrogel, 4 arm PEG Succinimidyl Glutarate (—SG) with a ester linker, 4 arm PEG Isocianate, 4 arm PEG Azide, 4 arm PEG norbornene. Similar reactive groups described above can be used with other multi-arm PEGs such as 6-arm and 8-arm PEGSs. The molecular weight of these polymers may vary from 1 KDa to 500 KDa. In a preferred embodiment, the polymer includes 4 arms although PEG-arms may increase to 16 arms. Similarly, any of the aforementioned polymers can be combined to form co-polymers, e.g. PEG-co-alginate, PEG-co-hyaluronic acid, etc. Alternatively, heterobifunctional PEGs, methoxy PEGs (-acrylate, -aldehyde, -amine, -biotin, -carbonate, -carboxyl, -hydrazide, -maleimide, —NHS, -oligopeptide, -phospholipid) can be used, and the like. In addition to these, Lipid-PEG derivates are also available.

Thermosensitive.

In another embodiment, the gel may be an in situ thermosetting/thermosensitive gel, which requires a change in temperature to form a physical gel, typically at or below body temperature but it can be administered through a single lumen or channel without a need for mixing. The concentration of polymer can be such that it is in a low viscosity state at room temperature (for example, 23-25° C.) and a higher viscosity state at body temperature, or just below body temperature at 35° C.

Biodegradable PEG-based copolymers have been fabricated to degrade through hydrolytic, enzyme-catalyzed or mixed mechanisms. The majority of these ABA triblock, BAB and AB diblock copolymers are thermosensitive polymers that gel below body temperature, although some transition from in the opposite direction (gel at and above body temperature). These are not covalent bonds but the gel is formed through ionic or nonionic interactions, such as through chain alignment between their hydrophobic-hydrophobic regions. By controlling the molecular weight of these blocks, the gel transition temperature can occur between, e.g., 25-37° C., more preferably 30-35° C., more preferably 30-33° C. The % w/v of these gels is typically between 5 and 50% concentration, preferably between 5 and 40/o concentration, more preferably between 10 and 20% concentration. Examples of amphiphilic ABA/BAB triblock and AB diblock copolymers follow: The hydrophilic A segment in this case is the PEG or PEO and the hydrophobic B segment is most a PPs/polyester/POE/PHB or a PEO penetrating the inner cavity of cyclodextrins. PEG di-block and tri-block copolymers can be formed with polyesters including PEG-PLA, PEG-PGA, PEG-PCL, MPEG-PCL, PEG-PLGA, PEG-LA-PEG, PLGA-PEG-PLGA, PEG-PLGA-PEG, PEG-PCL-PEG, PEG-PGA-PEG, PCL-PEG-PCL or with trimethylene carbonate (PEG-TMC), PEG-chitosan, PEG-dextrose, PEG-gelatin, and other suitable combinations of polymers may be selected. In another embodiment poly (ethylene oxide-co-glycidol)-CHO is formed by mixing aqueous glycol chitosan and poly(EO-co-Gly)-CHO to form a cross-linked hydrogels in situ. Alternatively, an α-cyclodextrin/PEG-b-PCL-dodecanedioic acid-PCL-PEG hydrogel (MPEG-PCL-MPEG) showed promise for cardiac applications delivering cells and may be suitable for use in locations as described herein. Alternatively, a four-arm PPO-PEO block copolymer (Tetonic) can be modified with acrylates for crosslinking and NHS-group added for reaction with tissue amines. Alternatively, the PEO-CMC hydrogel (Oxiplex, MediShield, Dynavisc, Aril, FzioMed) has many of the characteristics to make it an excellent polymer to deliver drugs to desired locations. Still other polymers include, PEO-PHB-PEO hydrogels. PEG-PCL-PEG or PCL-PEG-PCL (PCEP) which transition from a solution at room temperature to a gel at body temperature are described. For example, in one embodiment, a PEG-PCL-PEG hydrogel (2K-2K-2K) forms a thermosensitive hydrogel that can be injected as a solution and forms a gel in situ. Neuroprotective drugs can be safety mixed into the hydrogel solution prior to injection in situ. Also, pH-block copolymer hydrogels may be well suited for this application and may include diblock copolymers such as PEG-PCL, PEG-PLA or triblock copolymers such as PEG-PLGA-PEG.

Pre-Formed PEG Hydrogels.

In another embodiment, PEG can be crosslinked ex vivo, dehydrated and then crushed. These particles can then be resuspended in an aqueous buffer with or without drug and stored in a preloaded syringe for injection. The advantage for this type of delivery system is the ability to provide clinician with the drug delivery system ready for use. One example of this technology is the TraceIT hydrogel (Augmentix), which is an injectable hydrogel that is visible under ultrasound, CT, and MR that can be injected with a 25G needle and remains in place for approximately three months and gradually degrades through hydrolysis and is bioresorbed over 7 months. The iodinated PEG confers the visibility under CT and MR. In one embodiment, a PEG (non-iodinated) slurry is injected with a wt % of between 2.5% and 20%. The neuromodulatory agents described may be incorporated into the hydrogel. Drugs with low solubility may be incorporated as crystals, particulates, or in a suspension. Higher water solubility drugs, incorporated in a hydrogel, typically only release for hours to days. If they are additionally incorporated into microspheres, liposomes, or nanoparticles, their release rate can be delayed and they can provide more sustained release. Further examples can be found, for example, in U.S. Pub. No. 2014/0363382 to Campbell et al., which is hereby incorporated by reference in its entirety.

Hyaluronic Acid.

The hyaluronic acid (HA) can be formulated with a range of viscosities and modulus of elasticities. Since it is shear-thinning or thixotropic, it can easily be injected through higher gauge needles and after it is injected the gel returns to its intramolecular and intramolecular ionic links are restored. As the shear force is increased, such as during injection, the hydrogel becomes thinner (shear-thinning) allowing the delivery of some hydrogels through a standard syringe needle or catheter such as a 27 G or 29 G thin walled needle or a 30 G needle, as necessary.

By varying the molecular weight of HA, the degree of crosslinking and the concentration of reactive HA precursors, hydrogels of varying pore size and viscosity and degradation rate can be produced. HA is negatively charged and so it can absorb a lot of water and expand forming a loose hydrated network. The HA may be in the form of randomly crosslinked HA chains and neuromodulatory agents can be encapsulated in the network without any covalent linkage. HA can be reacted with an excess of glycidyl methacrylate (GMA) to form crosslinked HAHA can be crosslinked with bisepoxide, divinyl sulfone derivatives under alkaline conditions, glutaraldehyde, biscarbodiimide and hydrazides under acidic conditions.

HA-based hydrogel particles (HGPs) also known as microgels or nanogels can be synthesized from water in oil emulsion crosslinking to form aqueous droplets of HA. These microscopic gels provide a convenient method to deliver drugs in the aqueous phase inside these gels.

Considerable work has gone into developing HA-based gels to solve the various needs of dermal fillers based on if tissue plumping or filling versus small wrinkle filling are needed. As a result, these gels have a wide variety of viscosity after injection. The complex viscosity (n*) relates to how the hydrogel flows from the needle and then later how much it spreads. Generally, Restylane SubQ>Perlane>Restylane, in that order, are more viscous hyaluronic acid fillers than Juvederm, Voluma>Juvederm Ultra Plus>Juvederm Ultra which have low viscosity. In these embodiments, it is preferably to have a hyaluronic acid based delivery system with a higher viscosity filler so that the agent will remain in place.

The following hyaluronic acid/hyaluronan based products include, for example, Perlane, Juvederm (Ultra, Ultra XC, Volume XC), Restylane and Hyalform, and collagen-based products such as Evolence. Perlane is more viscous than Restylane containing particles between 750 and 1000 microns, similarly Juvederm's line contains hyaluronic acids with different viscosities/thicknesses.

Another advantage to hyaluronic acid based products beyond their extensive clinical evaluation is that it is possible to dissolve excess filler with hyaluronidase. In one embodiment, the glycosidic bonds of hyaluronic acid can be cleaved with Vitrase (ovine hyaluronic acid, 200 USP/ml) which can be injected by itself or with saline into the site containing the hyaluronic acid to assist in the diffusion of fluid and clearance of the hyaluronic acid. For example, in one embodiment 20 mg/ml of crosslinked hyaluronic acid (cross-linked with BDDE) is suspended in PBS at neutral pH. Lidocaine (0.3%) can also be incorporated the gels to reduce the pain associated with injection Hyaluronidase is also delivered locally to increase nerve permeability and is sometimes used in conjunction with 10% hypertonic saline as a neurolytic agent and to break up adhesions in the spine (1500 U/10 ml). Conventional hyaluronic acid hydrogel crosslinking can be employed, as disclosed, for example, in U.S. Pat. No. 4,582,865 to Balazs et al., which is hereby incorporated by reference in its entirety.

Ethanol Based Systems.

With hydrophobic drugs and hydrogel monomers or hydrogels are soluble in ethanol, a high drug-loaded hydrogel can be created. Since ethanol can act as either a solvent for the polymer as well as a neurolytic agent and the alcohol is rapidly absorbed once placed in the body, novel hydrogels using alcohol may be possible. In one embodiment the neurolytic agent is coadministered with the hydrogel in an aqueous/ethanol solution. The ethanol, between, for example, 10 and 50 wt %, more preferably 30%, can be incorporated in a HA- or PEG-based hydrogel. With regard to the in situ forming crosslinked hydrogels, the ethanol can either be incorporated in the precursor solution prior to mixing the agents and formation of the gel. This may be reflected in the kit in which the alcohol is an additional vial.

In another embodiment, the active agent is added to the polymer solution where it is either dissolved (soluble) or dispersed (insoluble—suspension/dispersion) in the polymer solution. After the solution is injected into the target site, the solvent (ethanol) diffuses away from the polymer-drug mixture while water diffuses in, causing the polymer to turn into a solid drug delivery implant. The drug is subsequently released by diffusion or dissolution. In one embodiment the drug is dissolved in ethanol and the monomers PEG methyl ether (MPEG)-PLA, acrylol chloride macromonomer, itraconic acid, and MPEG methacrylate to form poly (LA-IA-MEG). In one embodiment, ethanol is added to the aqueous phase of the polymer and modifies the gelation time. Addition of ethanol, for example 25% ethanol, improves the mechanical properties of the gel.

Poloxamers.

The Pluronic class of polymers are nonionic triblock copolymers of poly(ethylene oxide)-poly(propylene oxide)-poly(ethylene oxide) (PEO-PPO-PEO) that are thermoreversible polymers that are thought to form as micelles aggregate together above the critical micellular concentration (CMC) to form a gel. Poloxamers form hydrogels as homopolymers or as uncomplexed multi-block copolymers. Poloxamer properties can further be controlled through crosslinking to improve the release of drug and modify the sol-gel transition behavior and critical gelation temperature and concentration. Poloxamers, such as P407, can be injected into the potential space and used to protect tissues encapsulated in the semi-solid gel from thermal damage such as RF, ultrasound, and radiation. Poloxamers form at between 10 and 60% wt/volume, more preferably between 20 and 50%, more preferably 25-35% wt/vol. The P407 is thermoreversible (15.4% in water) and transitions to a semi-solid at body temperature. Pluronic F-127 is a nonionic surfactant polyol (MW 12.5 KDa) with 7% PPO that at low concentrations forms micelles and at high concentrations packs to form high modulus gels. HPMC can be added to Poloxamers to prolong the gelation time. In another example, a polaxamer-heparin hydrogel if formed from poloxamer (PEG-propylene glycol-PEG). In another example, 20% ethanol is added to the Poloxamer solution without affecting the concentration for gelation. At 30% ethanol and 35 wt % F-127 can form at 20 degrees Celsius. As another example, two Pluronic block copolymers can be mixed to vary the properties of the gel. In one embodiment, Pluronic F127 can be loaded with the therapeutic agent and then F-127 can be mixed with F-68 to assist in reducing the gelation temperature.

Other Polymers.

The aforementioned not limiting, there is an unmet need for an injectable gel, that includes a glue, slurry, scaffold, or hydrogel- or a more simple emulsion or other viscous solution formulation that can deliver a neuromodulatory agent or combination of neuromodulatory agents. In some embodiments, the therapy can include neuromodulatory agent(s) delivered in a gel. In some embodiments the neuromodulatory agent is co-delivered with an anesthetic and/or contrast agent. In some embodiments, the anesthetic, if delivered, is administered immediately prior to the injection of the therapy.

Formulations include gels, and more particularly hydrogels that can form either through physical crosslinking (ionic interactions, hydrogen bonding, hydrophobic-hydrophobic interactions) or chemical crosslinking (Schiff base crosslinking, Diels-Alder crosslinking, Michael addition, CuAAC, SPAAC, Thiol-ene, Oxime, and Radical polymerization. The polymerization of hydrogels can be induced by physical mixing, temperature, pH, UV light exposure, and/or ionic concentration. Polymeric gels may be homopolymers, copolymers, or multi-polymer interpenetrating polymeric hydrogels. The gels may be nonionic (neutral), anionic, cationic, amphoteric electrolytes (ampholytic, acid and base groups), or zwitterionic (anionic and cationic groups in each structural repeating unit).

Echogenicity

In some embodiments, the gel can be sufficiently echogenic to allow the clinician administering the therapy to confirm its appropriate delivery within the desired anatomical location. In some embodiments, the gel has low to no internal pores, decreasing the rate water permeation through the gel, decreasing the rate of drug release.

After the gel has formed at the site or has been delivered to the site, the gel may provide for sustained or controlled release of the agent. This can provide more effective means to deliver therapeutic concentrations locally to the target tissue.

Polymers.

The drug delivery system may be comprised of a nondegradable polymer such as silicone, cellulose or ethylene vinyl acetate copolymer (EVAc), polystyrene, acrylamide, or cyanoacrylate glues. However, in some embodiments, the drug delivery system is comprised of biodegradable or bioerodible polymers. The drug delivery systems may be comprised of natural polymers including, but not limited to glycosaminoglycans and polysaccharides including but not limited to collagen, alginate, chitosan, pullulan, hyaluronic acid, hyaluronan, gelatin, carboxymethylcellulose (CMC) silk fibroin, dermatan sulfate, chitin, and chondroitin sulfate and derivatives thereof. Synthetic biodegradable polymers such as polylactic acid (D-, L-, D/L, PLA), polyglycolic acid (PGA), polylactic-co-glycolic acid (PLGA), polyaminoacids, polyorthoesters (POE), polycaprolactone (PCL), polyphosphoesters (PPE), poly(urethanes), polyanhydrides, polyimide, propylene glycol, poly(ethylene oxide), olyethylene glycol (PEG), poly(2-hydroxyethyl methacrylate) (PHEMA), and poly N-(2-hydroxypropyl)-methacrylamide (PHPMA), poly(methylmethacrylate) (PMMA) (Artecoll or Artefill—microspheres in a collagen gel), polyacrylamide (Aquamid) poly(ester urethane), cyclodextrin, poly(alkene oxide), poly (hydroxyalkanoate), poly(R-3-hydroxybutyrate) (PHB) and co-hetero-polymers thereof. Other components include glycerol, poly(glycerol-co-sebacic acid), and poly(ethylene oxide) (PEO) These polymers can be further modified to create hydrogels with cholesterol methacrylate or 2-ethoxyethyl methacrylate (EOEMA). The polymers can include linear backbones or star or branched polymers with molecular weights ranging from 1 kDa to 500 kDa, more preferably 2 kDa to 300 kDa. Some examples include but are not limited to poly(epsilon-caprolactone-co-ethyl ethylene phosphate, a copolymer of caprolactone and ethyl ethylene phosphate (PCLEEP), polilactofate-PLA (PPE-PLA) copolymer (Paclimer Microspheres), polyanhydride-co-imide, poly(TMA-Tyr-:SA:CPP 20:50:30) polymer (Chiba et al), poly(vinyl alcohol) based cryogels. For these purposes, polyscaccharides, N-isopropylacrylamide (NIPAAm) copolymers (thermosensi), poloxamer and its copolymers, pEO-P(D,L)LGA copolymers and liposome based systems. In one embodiment, copolymerization of NIPAAm, acrylic acid and hydroxymethacrylate and TMC (HE-MAPTMC) may be suitable for injection.

Additional biodegradable polymers, solvents, aqueous carriers, are described in, for example, U.S. Pat. No. 6,545,067 to Buchner et al. and U.S. Pub. No. 2014/0363498 to Sawhney et al., both of which are incorporated by reference in their entireties).

Natural Gels Based Gels:

Chitosan-β-glycerophosphate/hydroxyl-ethyl cellulose (chitosan/β-GP/HEC) hydrogels, chitosan-polylysine hydrogels, alginate hydrogels, and collagen hydrogels can also be utilized in some embodiments, as can rapid gelling hydrogels composed of mixtures of chitosan-thiol modified and polylysine-maleimide give gelation times of between, e.g., about 15 and 215 seconds. These hydrogels have excellent hemostatic properties. In another embodiment gelatin methacrylate can be utilized.

Fibrin-Based Gels.

Chondroitin sulfate proteoglycan gel (CSPGs), such as Aggregan, Neurocan, Brevican, Versican, and NG2 exert inhibitor influences on axon growth as can urinary bladder matrix (UBM). Fibrin and fibrinogen, whether mammalian or non-mammalian, may be used as an injectable gel but may be less desirable because of its ability to support neurite extension. Matrigel and other fibrin gels in some cases do not stay around for long enough to prevent regeneration. However, fibrin may be conjugated with PEG to improve its characteristics. In one embodiment, the drug is delivered in a crosslinked fibrin matrix, sealant glue or slurry, such as the FDA approved Tisseel. By varying the concentration of thrombin used to induce polymerization, the solution to gel transition can be controlled.

Other commercial formulations that may be suitable include collagen based gels such as Evolence (with Glymatrix technology), calcium hydroxyapatite microspheres (CaHA, Radiesse), and pro-fibrotic PLLA microspheres (Sculptra), and/or the fibrin matrix or glue (Tisseel) made of fibrin and thrombin.

Biodegradable alginate or collagen, or agarose-chitosan hydrogels. In one example a chitosan hydrogel is prepared by mixing chitosan (2% w/v) with dibasic sodium phosphate (DSP) to for a gel that at body temperature. In one embodiment, the BST-Gel platform (Biosyntech, Canada) is utilized, that includes chitosan neutralized with beta-glycerophosphate (GP) which forms a gel at room temperature.

Mechanism of drug release. Sustained release gels may additionally incorporate complexes, microspheres, nanospheres, nanocrystals, micelles, liposomes, nanoliposomes, or nanocomplexes, as known in the art. Alternatively, a viscous formulation such as a suspension, emulsion or a slurry can be delivered to the tissue, such as a slurry of hydrogel particles, in which the release rate is primarily controlled by the environment into which it is injected. Drug diffusion through gels can also be controlled by the polymer concentration, the degree of swelling (hydration factor).

Microspheres.

In order to provide more controlled release and reduce the burst, the drugs may be loaded into microspheres. These microspheres can be delivered in a slurry or incorporated into a hydrogel. In one embodiment, the microspheres are incorporated into an in situ forming hydrogel. In another embodiment they are incorporated into a lyophilized phase of the in situ polymerizing hydrogel in which they will only get resuspended when they are ready for use. The microspheres may release the neuromodulatory agent with or without neuromodulatory agent also loaded in the hydrogel phase. Alternatively, the microspheres may release one agent and the aqueous phase of the hydrogel may release a different agent. In this embodiment, the release rates of the drug from the microsphere and gel phase may differ. Typically the release of drug from the microspheres will be slower than that from the hydrogel. In some embodiments, the microspheres are biodegradable so that they are eventually cleared from the site of injection.

Microspheres can be formed by single or double-emulsion. In one embodiment, a poly(ethylene glycol) based microsphere system if formed with a water-in-water emulsion process. A single (W/O) or double W/O/W emulsion process can be used to prepare the drug. By adjusting the number of sites of hydrolysis, emulsion conditions and varying the PEG molecular weight the degradation and erosion can be controlled. In one embodiment, PEG-diacrylate (PEGDA) chains are reacted with dithiol molecules to form hydrolytically labile ester linkages proximal to thio-ether bonds, PEG-dithiol (PEG-DTT). A water-in-water emulsion process is then used to synthesize the PEG microspheres. Alternatively, the PEG-DTT polymer solution can be dispersed in a 40 kDa dextran-rich aqueous phase and the acrylate groups in the droplets can be crosslinked with UV light to form microspheres. The microspheres are removed from the emulsion by dilution of the dextran-rich phase and centrifugation.

Nanoparticles

If intracellular delivery of these agents is desired, the neuromodulatory agent can be encapsulated within nanoparticles which are more readily endocytosed into the cells. Alternatively, the gold nanoparticles can be conjugated directly to the neuromodulatory agents as these readily accumulate within neurons.

Nanocrystals.

For example, a drug may be formulated in nanocrystals and dispersed in a drug delivery system. The crystals can be sieved to achieve a particular range of particle size in order to better control the release of drug. Alternatively, the drug may be micronized to reduce the size of the drug particles.

In some embodiments, the drug release occurs through diffusion of the drug from the drug delivery system. In one embodiment, the drug crystals are loaded into the hydrogel, and the release of the drug occurs as the hydrogel absorbs water after implantation causing solubilization of the hydrophobic drug crystal and subsequent sustained diffusion into the surrounding tissues, thus the polymer hydrogel itself is imparting Coprecipitates.

Instead of microspheres, the poorly water soluble drugs may be complexed with one or more pharmacological carriers. In one embodiment an inert water-soluble carbohydrate is selected to form a coprecipitate with a neuromodulatory agent in order to better control the release profile of the drug. For example, the drug can be coprecipitated with fructose, polydextrose or xylose at a ratio of drug: carrier of between 1:5 to 1:20.

Embedded drug delivery systems to facilitate controlled release of drugs from the hydrogels include The drug is loaded into microspheres in a hydrogel that provide the rate-limiting release of the drug. The polymers may degrade by bulk or surface erosion over a period of days to weeks to months, as needed for a given application. For example, in one embodiment, a thermoresponsive Poloxamer gel is combined with pH sensitive chitosan nanocomplexes containing the active agent.

Polymer Conjugation.

The polymer may be conjugated to the drug with an enzymatic or hydrolytic linkage. In one embodiment, the linkage is a hydrolytic linkage off of the backbone of is the polymer and upon delivery into an aqueous environment, hydrolysis causes release of the drug.

Lipophilic for Depots.

Highly lipophilic agents may be particularly desirable agents to deliver to nerves and are efficient in forming depots in the fascia and adipose tissue through which these nerves run.

Differential Sensitivity.

In another embodiment, a chemical agent is delivered that is preferentially more sensitive to one type of neural fiber than another. For example, sympathetic efferent fibers are recognized to be more sensitive to anesthetic than sensory afferent fibers. In another embodiment, the soma themselves are targeted such as the sympathetic ganglia or the dorsal root ganglia.

A further embodiment includes adding proteolytically degradable sites in the PEG system, enabling both proteolytic and hydrolytic or mixed-mode degradation.

Free Base.

Alternatively, the drug can be converted to its free base, where applicable, and injected or delivered as a viscous paste directly or incorporated within a drug delivery system.

Drug Loading Levels.

The drug loading level can be in some embodiments about 1% to 80%, about 5 to 50%, or about 5 to 20% in some cases Volumes of Agent or Formulation Administered.

Although the physician will have the discretion to deliver the appropriate volume of therapy, in some embodiments, volumes from about 1 ml to 30 ml are delivered in and around various neural targets. In some embodiments, volumes between about 1 ml and 20 ml are delivered to treat the target vessels or organs, such as between about 2.5 and 10 ml, or 1 and 5 ml.

The drug and/or drug-polymer formulations may also incorporate contrast agents to visualize the target site for delivery during the clinical procedure. Ionic contrast agents for visibility under x-ray fluoroscopy and CT include diatrizoate (Hypapaque) and metrizoate (Isopaque 370) monomers and ioxaglate (Hexbrix) dimer; non-ionic kind include iopamidol (Isovue 370), iohexol (Omnipaque 350), iopromide (Oxilan 350), iopromide (Ultravist 370), iodixanol (Visipaque 320) monomers and ioversol dimer. Contrast agents for visibility under ultrasound include microbubbles of suphur hexafluoride (Sonovue, Bracco) and albumin shell with octofluoropropane gas (Optison, GE Healthcare) or lipid microspheres (Perflexane, Alliance Pharmaceutical; Perflutren). Barium sulphate may also be mixed into the formulation to improve the visibility of the drug formulation during injection to the target nerve site. For treatment procedures under MRI, contrast agents based on gadolinium like gadoterate (Dotarem), gadodiamide (Omniscan), gadobenate (MultiHance), gadopentetate (Magnevist), gadoteridol (ProHance), gadoversetamide (OptiMARK), gadobutrol (Gadavist), and gadopentetic acid dimeglumine (Magnetol) may be incorporated into the polymer and/or drug formulation. Many other gadolinium, iron-oxide, iron-platinum, manganese and protein-based contrast agents may also be incorporated into the drug or drug-polymer formulations to improve the visibility of drug injection under MRI.

The drug and/or polymer formulations may also incorporate anesthetic agents to reduce pain during the clinical procedure. Examples of ester-based anesthetic agents that may be incorporated into the formulation include, procaine, amethocaine, cocaine, benzocaine, tetracaine. Examples of amide-based are lidocaine, prilocaine, bupivicaine, levobupivacaine, ropivacaine, mepivacaine, dibucaine and etidocaine. They may be included in the injectable (non-polymer) or polymer-based drug formulations.

The polymer-based drug formulations may be prepared outside the body in solid or gel form and delivered using different delivery systems to the target nerve locations. Ingredients or precursors of the formulations may be pre-packaged and sterilized, in dry or liquid forms, at a manufacturing facility. The dry or aqueous precursors may be premixed by medical personnel in the clinical setting and injected at the target nerve site. Water in the aqueous environment surrounding the target nerve or ganglion initiates transformation and the formation of the drug-releasing hydrogel implant. Alternatively, the finished product may be mixed, sterilized and packaged at a manufacturing facility or mixed by medical personnel.

Dry powder formulations can comprise a mixture of two or more individual dehydrated precursors and the drug formulation. The precursors activate upon exposure to water in bodily tissue, dissolve and simultaneously cross link to form the hydrogel implant containing the drug formulation. In one embodiment, the precursors may comprise a lyophilized, or freeze-dried forms that are compounded together with the drug. As an example, a two-part dehydrated hydrogel precursor mixture may comprise of an electrophilic, multifunctional poly(ethylene glycol) ("PEG") precursor and a multifunctional, nucleophilic PEG precursor. These two components may be compounded together with the drug, when dry. Upon exposure to an aqueous environment, rapid chemical crosslinking occurs and forms a drug-releasing hydrogel implant. Another embodiment comprises a fully-synthetic, solid PEG particulate hydrogel composition. A degradable PEG hydrogel is fabricated, then dried or lyophilized, pulverized and mixed with the drug (biologically active ingredient) powder to form the hydrogel implant near the target nerve site using specific delivery systems.

Other polymer-based drug formulations may also be prepared or cross-linked inside the body to form the drug formulation described using different delivery systems. Two or more ingredient formulations may be prepared, packaged and sterilized at a manufacturing facility (separate packages or a combined package with multiple chambers). They can be mixed using mixers, injecting guns and delivery systems to that the polymers cross-link at the target nerves site location and release the drug over time.

In another embodiment the hydrogel-based drug formulation product may be fabricated in the anhydrous form and delivered to the target site in solid form. In situ swelling after the plug comes into contact with water in the tissue initiates drug release to the target tissue.

Other Diseases, Targets and Pathways

Other inflammatory diseases, disorders and medical conditions may also be treated methods and drug formulations described above by administering the drug locally near other organs and tissue, such as the liver, kidneys, thymus, gut, pancreas, adrenal gland, and the hypothalamus. For example, efferent vagus nerve signaling has been implicated in facilitating lymphocyte release from the thymus via a nicotinic acetylcholine receptor response. Studies have shown that nicotine may be effective in treating some cases of inflammatory bowel disease (IBD). FIGS. 2, 3, 7, 8, 9 and 10 illustrate some of the targets and pathways to control inflammation.

Efferent vagal innervation from the DMV innervates the gut myenteric plexus and muscularis externa where macrophage-like cells are in present near vagal nerve endings. The proximal colon is densely innervated by the vagus compared to the distal segments that are innervated by sympathetic nerves. The vagus nerve controls anti-inflammatory activities through ChAT-expressing T cells or B cells in the spleen and requires an intact splenic nerve. ChAT-expressing T cells and B cells are also found in gut-associated lymphoid tissue (GALT) such as Peyers patches. They interact with macrophages via secretion of ACh and downregulate the production of proinflammatory cytokines and regulate mucosal immune cells. Sympathetic innervation also exists for lymphoid organs in the gut (GALT) and mesenteric lymph node (MLN). Vagus nerve fibers in the gut, proximal colon, distal colon and the mesenteric plexus may be upregulated through local chemo neuromodulation to attenuate the release of inflammatory cytokines. Alternatively, the sympathetic nerve fibers involved with these organs and their tissue structures may be also downregulated through the local administration of drug formulations.

Potential nerve sites and target ganglia to attenuate inflammation through local chemo neuromodulation and treat the medical conditions associated with inflammation and sepsis include the cranial nerve III, cranial nerve VII, cranial nerve IX, sphenopalantine ganglion, ciliary ganglion, submandibular ganglion, otic ganglion, sympathetic ganglia, sympathetic ganglia, cervical sympathetic ganglia, coccygeal ganglia, celiac ganglion, inferior mesenteric ganglion, inferior mesenteric ganglion, cardiac and pulmonary plexus, hypogastric plexus, celiac plexus, spinal nerves, post-ganglionic fibers to the spinal nerves, sympathetic nerves, pelvic nerves, greater splanchnic nerve, lumbar splanchnic nerves and the lesser splanchnic nerves.

These medical conditions may be treated through local chemo neuromodulation by a single administration of a small volume of drug formulation, using methods described above. The formulations may be injected using a needle or a catheter. Specific nerve target sites, ganglia, plexi, nerve fibers and portions of a nerve may be accessed by introducing the device through the femoral vein or artery and advanced to reach the cranial and cerebral arteries and veins, submandibular arteries and veins, otic artery and veins, intercostal arteries and veins, celiac arteries and veins, inferior mesenteric arteries and veins, cardiac arteries and veins, pulmonary arteries and veins, hypogastric arteries and veins, pelvic arteries and veins, hepatic arteries and portal veins, renal arteries and veins, the adrenal arteries and veins, the adrenal medulla and other arteries and veins supplying the thymus, hypothalamus, pituitary glands, etc.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "accessing the splenorenal ligament" includes "instructing the accessing of the splenorenal ligament." The ranges disclosed herein also encompass any and all overlap, subranges, and combinations thereof. Language such as "up to," "at least" "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Furthermore, various theories and possible mechanisms of actions are discussed herein but are not intended to be limiting.

What is claimed is:

1. A method of modulating inflammation in a patient, comprising:
   providing a therapeutic agent delivery system comprising at least one therapeutic agent, wherein the at least one therapeutic agent is configured to provide an anti-inflammatory effect;
   accessing between one or more folds of one or more ligaments directly connected to a splenic hilum of the patient, accessing between the one or more folds of the one or more ligaments comprising:
      inserting a catheter into a first blood vessel;
      advancing the catheter into a second blood vessel; and
      penetrating a wall of the second blood vessel with a portion of the catheter to a position between the one or more folds of the one or more ligaments,
      wherein the one or more ligaments comprises at least one of a splenorenal ligament or a gastrosplenic ligament of the patient; and
   delivering the therapeutic agent delivery system between the one or more folds of the one or more ligaments, the therapeutic agent delivery system comprising a hydrogel comprising the at least one therapeutic agent,
   wherein the hydrogel comprises an injectable in situ forming hydrogel slurry being configured to limit a spread of the hydrogel beyond the one or more folds of the one or more ligaments.

2. The method of claim 1, wherein the one or more ligaments comprises the splenorenal ligament.

3. The method of claim 1, wherein the one or more ligaments comprises the gastrosplenic ligament.

4. The method of claim 1, wherein the one or more ligaments comprises both the gastrosplenic ligament and the splenorenal ligament.

5. The method of claim 1, wherein the second blood vessel is selected from the group consisting of: a splenic artery and a splenic vein.

6. The method of claim 1, wherein delivering the therapeutic agent delivery system comprises delivering an implant comprising a therapeutic agent into the one or more ligaments.

7. The method of claim 6, wherein the implant after delivery coils around a blood vessel between the one or more folds of the one or more ligaments.

8. The method of claim 1, wherein delivering the therapeutic agent delivery system comprises delivering a plurality of microspheres into the one or more ligaments.

9. The method of claim 1, wherein the therapeutic agent comprises nicotine.

10. A method of modulating inflammation of a patient, comprising:
    accessing between one or more folds of one or more ligaments directly connected to a splenic hilum of the patient, wherein the one or more ligaments comprises at least one of a splenorenal ligament or a gastrosplenic ligament of the patient; and
    flowing a gel comprising a therapeutic agent between the one or more folds of the one or more ligaments such that the one or more folds of the one or more ligaments serves as a boundary and limits a spread of the gel to between the one or more folds of the one or more ligaments,
    wherein the therapeutic agent is configured to provide an anti-inflammatory effect, and wherein the gel comprises an injectable in situ forming hydrogel slurry being configured to limit the spread of the gel beyond the one or more folds of the one or more ligaments.

11. The method of claim 10, wherein the one or more ligaments comprises the splenorenal ligament.

12. The method of claim 10, wherein the one or more ligaments comprises the gastrosplenic ligament.

13. The method of claim 10, wherein the one or more ligaments comprises both the gastrosplenic ligament and the splenorenal ligament.

14. A method of modulating inflammation in a patient, comprising:

providing a therapeutic agent delivery system comprising at least one therapeutic agent, wherein the at least one therapeutic agent is configured to provide an anti-inflammatory effect;

accessing between one or more folds of one or more ligaments directly connected to a splenic hilum of the patient, accessing between the one or more folds of the one or more ligaments comprising:

inserting a catheter percutaneously; and positioning the catheter between the one or more folds of the one or more ligaments with a portion of the catheter, wherein the one or more ligaments comprises at least one of a splenorenal ligament or a gastrosplenic ligament of the patient; and delivering the therapeutic agent delivery system between the one or more folds of the one or more ligaments, the therapeutic agent delivery system comprising a hydrogel comprising the at least one therapeutic agent, wherein the hydrogel comprises an injectable in situ forming hydrogel slurry being configured to limit a spread of the hydrogel beyond the one or more folds of the one or more ligaments.

15. The method of claim 14, wherein the one or more ligaments comprises the splenorenal ligament.

16. The method of claim 14, wherein the one or more ligaments comprises the gastrosplenic ligament.

17. The method of claim 14, wherein the one or more ligaments comprises both the gastrosplenic ligament and the splenorenal ligament.

* * * * *